US006762283B1

(12) United States Patent
Wallach et al.

(10) Patent No.: US 6,762,283 B1
(45) Date of Patent: Jul. 13, 2004

(54) CASPASE-8 INTERACTING PROTEINS

(75) Inventors: David Wallach, Rehovot (IL); Marcus Schuchmann, Mainz (DE); Tanya Goncharov, Ashkelon (IL)

(73) Assignee: Yeda Research and Development Co. Ltd., Rehovot (IL)

(*) Notice: Subject to any disclaimer, the term of this patent is extended or adjusted under 35 U.S.C. 154(b) by 80 days.

(21) Appl. No.: 09/644,827

(22) Filed: Aug. 24, 2000

Related U.S. Application Data

(63) Continuation-in-part of application No. PCT/IL99/00698, filed on Dec. 23, 1999.

(30) Foreign Application Priority Data

Dec. 24, 1998 (IL) ................................................ 127721
Sep. 28, 1999 (IL) ................................................ 132105

(51) Int. Cl.$^7$ ............................................. C09K 14/00
(52) U.S. Cl. ..................................... 530/350; 536/23.5
(58) Field of Search .............................. 536/23.1, 23.5, 536/24.31; 530/300, 350, 402; 514/2, 12

(56) References Cited

U.S. PATENT DOCUMENTS 6,326,354 B1 * 12/2001 Gross et al. ................. 435/375

FOREIGN PATENT DOCUMENTS

| WO | WO 93/17178 | 8/1993 |
|---|---|---|
| WO | 97 48797 | 12/1997 |
| WO | 98 33883 | 8/1998 |
| WO | 99 61626 | 12/1999 |
| WO | WO 00/29674 | 5/2000 |

OTHER PUBLICATIONS

Bertin, J, et al, Proc Natl Acad Sci USA 1997 Feb.; 94: 1172–1176.*
Scaffidi, C, et al, J Biol Chem 1997 Oct. 24; 272 (43): 26953–26958.*
Hu, S, et al, J Biol Chem 1997 Apr. 11; 272 (15): 9621–9624.*
Frank, AW, CRC Crit Rev Biochem 1984; 16 (1): 51–101.*
Scanlan, MJ, et al, Int J Cancer 1998; 76: 652–658.
Medema, JP, et al, EMBO J 1997; 16 (10): 2794–2804.
Takahashi, A, et al, Oncogene 1997; 14: 2741–2752.
Chou, KC, et al, FEBS Lett 1997 Dec. 8; 419 (1): 49–54.
Muzio, M, et al, J Biol Chem 1997 Jan. 31; 272 (5): 2952–2956.
Bowie, et al, Science 1990; 257: 1306–1310.
Burgess, et al, J Cell Biol 1990; 111: 2129–2138.
Lazar, et al, Mol Cell Biol 1988; 8: 1247–1252.
USPTO Search Report US–09–644–827–6.rsp (result 4), Swiss Protein Database Accession No. Q9UQL6; O60528; O60340.*

Gibson et al, "Homology between two EBV early genes and HSV ribonucleotide reductase and 38K genes", *Nucleic Acids Res* ; 12(12):5087–5099 (1984).
Ishikawa et al, "Prediction of the coding sequences of unidentified human genes. VIII. 78 new cDNA clones from brain which code for large proteins in vitro", *DNA Res* 4(5):307–313 (1997).
Ishikawa et al, "Prediction of the coding sequences of unidentified human genes. X. The complete sequences of 100 new cDNA clones from brain which can code for large proteins in vitro", *DNA Res* 5(3): 169–176 (1998).
Iizuka et al, "Enhanced expression of nucleobindin in lymphatic organs of lupus–prone mice", *Lupus.* 6(4):365–370 (1997).
Kamada et al, "A cloning method for caspase substrates that uses the yeast two–hybrid system: cloning of the antiapoptotic gene gelsolin", Proc Natl Acad Sci USA 95(15):8532–8537 (1998).
Kamine et al, "Identification of a cellular protein that specifically interacts with the essential cysteine region of the HIV–1 Tat transactivator", *Virology* 216(2):357–366 (1996).
Medina et al, "Induction of caspase–3 protease activity and apoptosis by butyrate and trichostatin A (inhibitors of histone deacetylase): dependence on protein synthesis and synergy with a mitochondrial/cytochrome c–dependent pathway", *Cancer Res* 57(17):3697–3707 (1997).
Miura et al, "Molecular cloning of nucleobindin, a novel DNA–binding protein that contains both a signal peptide and a leucine zipper structure", *Biochem Biophys Res Commun* 187(1);375–380 (1992).
Miura et al, JP 06 025292, "Protein and its Gene" (Feb. 1, 1994) Abstract Only (Database WPI: Section Ch, Week 199410 (Derwent Publications)).
Wright et al, "A ribonucleotide reductase inhibitor, MDL 101,731, induces apoptosis and elevates TRPM–2 mRNA levels in human prostate tumor xenografts", *Exp Cell Res* 222(1):54–60 (1996).
Accession M96824, Miura et al, "Human nucleobindin precursor" (Nov. 19, 1992) (GENEMBL 'Online!).
Accession V01555, Farrell P, "Epstein–Barr virus (EBV) genome, strain 895–8" (Dec. 6, 1983) (GENEMBL 'Online!).
Accession H23509, Hillier et al, "ym53a01.r1 Soares infant brain 1NIB *Homo sapiens* cDNA clone IMAGE:51785 3' similar to ti gb:M64992 proteasome component C2 (human), mRNA sequence" (Jul. 8, 1995) (GENEMBL 'Online!), (List continued on next page.)

*Primary Examiner*—Anthony C. Caputa
*Assistant Examiner*—Stephen L. Rawlings
(74) *Attorney, Agent, or Firm*—Browdy and Neimark, P.L.L.C.

(57) ABSTRACT

There are provided proteins which interact with caspase-8. Production and use of such proteins is also provided.

7 Claims, 19 Drawing Sheets

OTHER PUBLICATIONS

Accession U49973, Robertson HM, "ORF2 associated to human trigger 1 transposable element" (Mar. 14, 1996) (GENEMBL 'Online!).

Accession C18037, Fujiwara T, "Human placenta cDNA 5'-end GEN–556E08" (Oct. 4, 1996) (GENEMBL 'Online!).

Accession AA608733, Hillier et al, "ae56f06.s1 Stratagene lung carcinoma 937218 *homo sapiens* cDNA clone IMAGE:950915 3' similar to TR:61224066 ORF2: Function unknown" (Oct. 1, 1997) (GENEMBL 'Online!).

Accession AB006626, O'Hara et al, "*Homo sapiens* mRNA for KIAA0288 protein, partial cds" (Oct. 31, 1997) (GENEMBL 'Online!).

Accession AB007870, O'Hara O, "*Homo sapiens* KIAA0419 mRNA complete cds" (Dec. 5, 1997) (GENEMBL 'Online!).

Accession U67734, Sheridan et al, "Human cPLA2 interacting protein mRNA, complete cds" (Jan. 6, 1999) (GENEMBL 'Online!).

Accession AB014515, O'Hara et al, "*Homo sapiens* mRNA for KIAA0615 protein, complete cds" (Jul. 15, 1998) (GENEMBL 'Online!).

GenBank AC004466: *Homo sapiens* 12q13.1 PAC RPCI5–1057120 (Roswell Park Cancer Institute Human PAC library), Version AC004466.1; GI:3617739; Sep. 17, 1998.

Abstract, XP–002137400, Jan. 19, 1998, AA746639.

Han et al., "MRIT, a novel death–effector domain–containing protein, interacts with caspases and BelX$_L$ and initiates cell death", *Proc. Natl. Acad. Sci.,* (1997), vol. 94, pp. 11333–11338.

Koseki et al., "ARC, an inhibitor of apoptosis expressed in skeletal muscle and heart that interacts selectively with caspases", *Proc. Natl. Acad. Sci,* (1998), vol. 95, pp. 5156–5160.

* cited by examiner

```
1/1                                                                                                   31/11
CGG CAC GAG GGC CTG GGC AAC GGC CGG CAC ACG CTG GGA CAG CAG GAA GTG GAA GTG GAC
 R   H   E   G   L   G   N   G   R   H   T   L   G   Q   Q   E   V   E   V   D
61/21                                                                                                 91/31
GGT CTG ACG GCC TAC GTG GCA GGT GAG CGC GAG CCT GAC CCA CTG GGT CCC AGG TCC CAG CCC
 G   L   T   A   Y   V   A   G   E   R   P   D   P   L   G   P   R   S   Q   P
121/41                                                                                                151/51
GCA TGC CAG GTG GCC CAC GAC CCC CCC AGA GCC TGC CCT CTC TGC TCT CAA GGC ACC AAG
 A   C   Q   V   A   H   D   P   P   R   A   C   P   L   C   S   Q   G   T   K
181/61                                                                                                211/71
ACG CTG AGT GGC AGC ATA GCC CCA ATG AAC GTC TGT GTC CGG GCA CTT CCT GCA GGC CAC
 T   L   S   G   S   I   A   P   M   N   V   C   V   R   A   L   P   A   G   H
241/81                                                                                                271/91
AGG TTC AGC ATG AAG TCG GCC TTG AAG GCT GCA TCC TTG CAC CCC GCC CAG TTG CTG GCG
 R   F   S   M   K   S   A   L   K   A   A   S   L   H   P   A   Q   L   L   G
301/101                                                                                               331/111
CTG gAG AAG AGT AAG GGG ACC TTG ACT GTG CTG ACG CAG ACT TCG TGG TGC TCG ACG
 L   E   K   S   K   G   T   L   T   V   L   T   Q   T   S   W   C   S   T
361/121                                                                                               391/131
ACT CCC TTC ACG TCC AGG CCA CCT ACA TCT CGG GTG AGC TGG TGT GGC AGG CGG ACG CAG
 T   P   F   T   S   R   P   P   T   S   R   V   S   W   C   G   R   R   T   Q
421/141
CTA GGC AGT GAC AAG GAC CTC GGC TGA
 L   G   S   D   K   D   L   G   *
```

Fig. 2

```
1/1                                     31/11
ggc gcg gct ccg ctc tcg gct ggg gtt cgt cac tgg gcg cgg gat ttg gcc gcc gcg ggg
 G   A   A   P   L   S   A   G   V   R   H   W   A   R   D   L   A   A   A   G
61/21                                   91/31
ctc cgg agc cgc tcg ctc ccg aca cgg ctc acg atg cgc ggc gac agg gcc ggc ggg ggc
 L   R   S   R   S   L   P   T   R   L   T   M   R   G   D   R   A   G   G   G
121/41                                  151/51
ccc gtg ctc cag ttc act aac tgc cgg atc ctg cgc gga ggg aaa ctg ctc agg gag gat
 P   V   L   Q   F   T   N   C   R   I   L   R   G   G   K   L   L   R   E   D
181/61                                  211/71
ctg tgg gtg cgc gga ggc cgc atc ttg gac cca gag aag ctg ttc ttt gag gag cgg cgc
 L   W   V   R   G   G   R   I   L   D   P   E   K   L   F   F   E   E   R   R
241/81                                  271/91
gtg gcc gac gag cgg cgg gac tgc ggg ggc cgc atc ttg gct ccc gga ttc atc gac gtg
 V   A   D   E   R   R   D   C   G   G   R   I   L   A   P   G   F   I   D   V
301/101                                 331/111
cag atc aac cgt gga TTT GGT GTT GAC TTC TCT CAA GCC ACG GAG GAC GTG GGT TCG GGG
 Q   I   N   R   G   F   G   V   D   F   S   Q   A   T   E   D   V   G   S   G
361/121                                 391/131
GTT GCC CTC GTG GCC CGG AGG ATC CTG TCG CAC GGC GTC ACC TCC TTC TGC CCC ACC CTG
 V   A   L   V   A   R   R   I   L   S   H   G   V   T   S   F   C   P   T   L
421/141                                 451/151
GTC ACT TCC CCA CCG GAG GCT TAT CAC AAG GTT GTT CCT CAG ATC CCT GTG AAG AGT GGT
 V   T   S   P   P   E   A   Y   H   K   V   V   P   Q   I   P   V   K   S   G
481/161                                 511/171
GGT CCC CAT GGG GCA GGG GTC CTC GGG CTG CAC CTG GAG GGC CCC TTC ATC AGC CGG GAG
 G   P   H   G   A   G   V   L   G   L   H   L   E   G   P   F   I   S   R   E
541/181                                 571/191
AAG CGG GGC GCG CAC CCC GAG GCC CAC CTC CGC TCC TTC GAG GCC GAT GCC TTC CAG GAC
 K   R   G   A   H   P   E   A   H   L   R   S   F   E   A   D   A   F   Q   D
601/201                                 631/211
TTG CTG GCC ACC TAC GGG CCC CTG GAC AAT GTC CGC ATC GTG ACG CTG GCC CCA GAG TTG
 L   L   A   T   Y   G   P   L   D   N   V   R   I   V   T   L   A   P   E   L
661/221                                 691/231
GGC CGT AGC CAC GAA GTG ATC CGG GCG CTG ACG GCC CGT GGC ATC TGC GTG TCC CTA GGG
 G   R   S   H   E   V   I   R   A   L   T   A   R   G   I   C   V   S   L   G
721/241                                 751/251
CAC TCA GTG GCT GAC CTG CGG GCG GCA GAG GAT GCT GTG TGG AGC GGA GCC ACC TTC ATC
 H   S   V   A   D   L   R   A   A   E   D   A   V   W   S   G   A   T   F   I
781/261                                 811/271
ACC CAC CTC TTC AAC GCC ATG CTG CCT TTC CAC CAC CGC GAC CCA GGC ATC GTG GGG CTC
 T   H   L   F   N   A   M   L   P   F   H   H   R   D   P   G   I   V   G   L
```

Fig. 3

```
841/281                                 871/291
CTG ACC AGC GAC CGG CTG CCC GCA GGC CGC TGC ATC TTC TAT GGG ATG ATT GCA GAT GGC
 L   T   S   D   R   L   P   A   G   R  C   I   F   Y   G   M   I   A   D   G
901/301                                 931/311
ACG CAC ACC AAC CCC GCC GCC CTG CGG ATC GCC CAC CGT GCC CAT CCC CAG GGG CTG GTG
 T   H   T   N   P   A   A   L   R   I  A   H   R   A   H   P   Q   G   L   V
961/321                                 991/331
CTG GTC ACC GAT GCC ATC CCT GCC TTG GGC CTG GGC AAC GGC CGG CAC ACG CTG GGA CAG
 L   V   T   D   A   I   P   A   L   G  L   G   N   G   R   H   T   L   G   Q
1021/341                                1051/351
CAG GAA GTG GAA GTG GAC GGT CTG ACG GCC TAC GTG GCA GGT GAG CGC CCT GAC CCA CTG
 Q   E   V   E   V   D   G   L   T   A  Y   V   A   G   E   R   P   D   P   L
1081/361                                1111/371
GGT CCC AGG TCC CAG CCC GCA TGC CAG GTG GCC CAC GAC CCC CCC AGA GCC TGC CCT CTC
 G   P   R   S   Q   P   A   C   Q   V  A   H   D   P   P   R   A   C   P   L
1141/381                                1171/391
TGC TCT CAA GGC ACC AAG ACG CTG AGT GGC AGC ATA GCC CCA ATG AAC GTC TGT GTC CGG
 C   S   Q   G   T   K   T   L   S   G  S   I   A   P   M   N   V   C   V   R
1201/401                                1231/411
CAC TTC CTG CAG GCC ACA GGC TGC AGC ATG GAG TCG GCC CTG GAG GCT GCA TCC CTG CAC
 H   F   L   Q   A   T   G   C   S   M  E   S   A   L   E   A   A   S   L   H
1261/421                                1291/431
CCC GCC CAG TTG CTG GGG CTG GAG AAG AGT AAG GGG ACC CTG GAC TTT GGT GCT GAC GCA
 P   A   Q   L   L   G   L   E   K   S  K   G   T   L   D   F   G   A   D   A
1321/441                                1351/451
GAC TTC GTG GTG CTC GAC GAC TCC CTT CAC GTC CAG GCC ACC TAC ATC TCG GGT GAG CTG
 D   F   V   V   L   D   D   S   L   H  V   Q   A   T   Y   I   S   G   E   L
1381/461                                1411/471
GTG TGG CAG GCG GAC GCA GCT AGG CAG TGA CAA GGA CCT CGG CTG AGA GGA CAC CTG GCC
 V   W   Q   A   D   A   A   R   Q   *  Q   G   P   R   L   R   G   H   L   A
1441/481                                1471/491
GCA GCG GGA TGC CAT CAG GGC CGG GTG GTT GGG GAG CTG GTC TCC AGG GAG TGA GTC GGG
 A   A   G   C   H   Q   G   R   V   V  G   E   L   V   S   R   E   *   V   G
1501/501
AGC CCT GCT GGA T
 S   P   A   G
```

Fig. 3 (a)

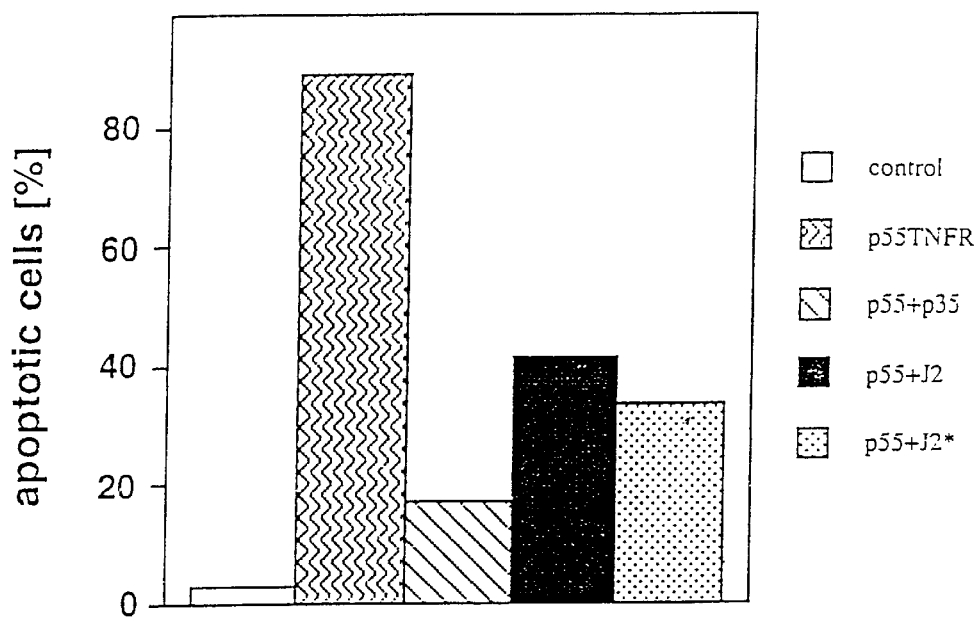
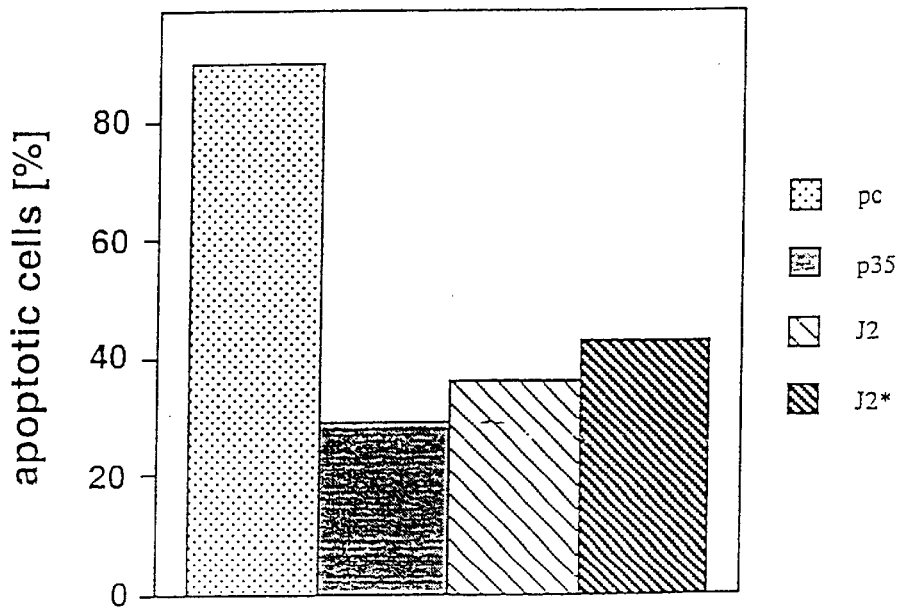
Fig. 4

```
         1           10          20          30          40          50          60          70          80          90         100
    1 GAGCAGCTCA AAACTCACGT CCAGGTGATC AAGAGGTCAG CCAAGCCGAG TGAGAAGCCC CGGCTGCGGC AGATACCCTC GGCTGAAGAC CTGGAGACAG  100
  101 ATGGCGGGGG ACCGGGCCAG GTGGTGGACG ATGGCCTGGA GCACAGGGAG CTGGGCCATG GGCCAGAGCC CCCGCTCCTC TCCAGCAGCA  200
  201 CCCTCAGGTG TTGCTCTGGG AACAGCAGCG ACTGGCTGGG CGGCTCCCCC CGGGACACAC CGGGACACT GTGCTGCTTC CTCTGGCCCA GGGTGGGCAC  300
  301 CGGCCTCTGT CCCGGGCTCA GTCTTCCCCA GCCGCACCTG CCTCACTGTC AGCCCCAGAG CCTGCCAGCC AGGCCCGAGT CCTCTCCAGC TCAGAGACCC  400
  401 CTGCCAGGAC CCTGCCCTTC ACCACAGGGC TGATCTATGA CTCGGTCATG CTGAAGCACC AGTGCTCCTG CGGTGACAAC AGCAGGCACC CGGAGCACGC  500
  501 CGGCCGCATC CAGAGCATCT GGTCCCGGCT GCAGGAGCGG GGGCTCCGGA GCCAGTGTGA GTGTCTCCGA GGCCGGAAGG CCTCCCTGGA AGAGCTGCAG  600
  601 TCGGTCCACT CTGAGCGGCA CGTGCTCCTC TACGGCACCA ACCCGCTCAG CCGCCTCAAA CTGGACAACG GAAGCTGGC AGGGCTCCTG GCACAGCGGA  700
  701 TGTTTGTGAT GCTGCCCTGT GGTGGGGTTG GGGTGGACAC TGAGCTAAAG AATGGTTTCG TTCATTCCTC GCCCCAGGA TTCATTCAGC CGCTGGGCCG CTGGCAGTGT  800
  801 CACTGACCTC GCCTTCAAAG TGGCTTCTCG TGCCGGCAGC TGCAACACGA CTGTGTGCC AGCAAGGCC TCATTGTAGA CAACTTCTTC CACCATGGCA AGCCATGGGC  900
  901 TTCTGCTTCT TCAACTCAGT GGCCATCGCC TACCAAGACC TGCCGGCAGC CTGCATCGCC GAGCAAGCC ATGACGACGG CAACTTCTTC CAGGGAGTG GGGCTGTGGA CACCATGGCA 1000
 1001 ACGGCACCCA GCAAACCTTC TACCAAGACC CCAGTGTGCT CTACATCTCC CTGCATCGCC ATGACGACGG GGACCCCCCC CTGAGTACCT GGCTGCTTTC 1100
 1101 TGAGGTAGGG GCTGGCAGCG GTGAGGGCTT CAATGTCAAT TTCTCTCCAG GTGGCCTGGG CTGGAGGTCT GGACCCCCCC GGATTTGATG CTGAGTACCT GGCTGCTTTC 1200
 1201 AGGATAGTCG TGATGCCCAT CGCCCGAGAG TGTTTTTGGAT ACATGACGCA ACCTAGTCCT GGTGTCTGCT GGATTTGATG CTGAGGGG TCACCCGGCC CCACTGGGTG 1300
 1301 GCTACCATGT TTCTGCCAAA TGTTTTTGGAT ACATGACGCA GCAACTGATG AACCTGGCAG GAGGCCAGT GGTGCTGGCC TTGGAGGGTG GCCATGACCT 1400
 1401 CACAGCCATC TGTGACGCCT CTGAGGCCTG TGTGGCTGCT CTTCTGGGTA ACAGGGTGGA TCCCCTTTCA GAAGAAGGCT GGAAACAGAA ACCCAACCTC 1500
 1501 AATTCCATCC GCTCTCTGGA GCCGTGATC CGGGTGCACA GTAAATACTG GGGCTGCATG CAGCCCCTGG CCTCCTGTCC AGACTCCTGG GTGCCTAGAG 1600
 1601 TGCCAGGGGC TGACAAGNA GAAGTGGAGG CAGTAACCGC ACTGGCGTCC CTCTCTGTGG GCATCCTGCC TGAAGATAGG CCCTCGGAGC AGCTGGTGGA 1700
 1701 GGAGGAAGAA CCTATGAATC TCTRA                                                                                    1725
```

Fig. 5A

```
        10         20         30         40         50         60         70         80         90        100
        |          |          |          |          |          |          |          |          |          |
  1  EQLKTHVQVI KRSAKPSEKP RLRQIPSAED LETDGGGPGQ VVDDGLEHRE LGHGQPEARG PAPLQQHPQV LLWEQQRLAG RLPRGSTGDT VLLPLAQGGH 100
101  RPLSRAQSSP AAPASLSAPE PASQARVLSS SETPARTLPF TTGLIYDSVM LKHQCSCGDN SRHPEHAGRI QSIWSRLQER GLRSQCECLR GRKASLEELQ 200
201  SVHSERHVLL YGTNPLSRLK LDNGKLAGLL AQRMFVMLPC GGVGVDTDTI WNELHSSNAA RWAAGSVTDL AFKVASRELK NGFAVVRPPG HHADHSTAMG 300
301  FCFFNSVAIA CRQLQQQSKA SKILIVDWDV HHGNGTQQTF YQDPSVLYIS LHRHDDGNFF PGSGAVDEVG AGSGEGFNVN VAWAGGLDPP MGDPEYLAAF 400
401  RIVVMPIARE FSPDLVLVSA GFDAAEGHPA PLGGYHVSAK CFGYMTQQLM NLAGGAVVLA LEGGHDLTAI CDASEACVAA LLGNRVDPLS EEGWKQKPNL 500
501  NSIRSLEAVI RVHSKYWGCM QRLASCPDSW VPRVPGADKE EVEAVTALAS LSVGILAEDR PSEQLVEEEE PMNL                            574
        |          |          |          |          |          |          |          |          |          |
        10         20         30         40         50         60         70         80         90        100
```

Fig. 5B

```
         |    10      |    20      |    30      |    40      |    50      |    60      |    70      |    80      |    90      |   100
   1  MFARSAGLCF  PWVPGVSHGG  DAEEVLAQHP  TPTGRGAERR  PRPPDSSAEG  DPGMLKPCGC  VPSPQKVALK  VGAPFCTCGC  FQRFHLPKAC  PGQQGSPESA  100
 101  RPRNRQPYAT  QNGPAPRPQV  LPGSSSRCCH  GYICFLFDSS  QTAEVEVGWG  GDTGSQLRPL  LRGAVYNSRM  WDSQKEDSKP  DILRLQNTQL  FHSVSLSTDG  200
 201  TQVSPGAHYC  SPTGAGCPRP  CADTPGPQPQ  PMDLRVGQRP  PVEPPPEPTL  LALQRPQRLH  HILFLAGLQQ  QRSVEPMRVK  MELPACGATL  SLVPSLPAFS  300
 301  IPRHQSQSST  PCPFLGCRPC  PQLSMDTPMP  ELQVGPQEQE  LRQLLHKDKS  KRSKEVATPA  QPSPTSQVPA  AACVACAVAS  SVVKQKLAEV  ILKKQQAALE  400
 401  RTVHPNSPGI  PYRSQGPCSG  QCPCSVPTPL  KQPWHSFCRT  LEPLETEGAT  RSMLSSFLPP  VPSLPSDPPE  HFPLRKTVSE  PNLKLRYKPK  KSLERRKNPL  500
 501  LRKESAPPSL  RRRPAETLGD  SSPSSSSTPA  SGCSSPNDSE  HGPNPILGSE  ALLGQRLRLQ  ETSVAPFALP  TVSLLPAITL  GLPAPARADS  DRRTHPTLGP  600
 601  RGPILGSPHT  PLFLPHGLEP  EAGGTLPSRL  QPILLLDPSG  SHAPLLTVPG  LGPLPFHFAQ  SLMTTERLSG  SGLHWPLSRT  RSEPLPPSAT  APPPGPMQP   700
 701  RLEQLKTHVQ  VIKRSAKPSE  KPRLRQIPSA  EDLETDGGGP  GQVDDGLEH   RELGHGQPEA  RGPAPLQQHP  QVLLWEQQRL  AGRLPRGSTG  DTVLLPLAQG  800
 801  GHRPLSRAQS  SPAAPASLSA  PEPASQARVL  SSSETPARTL  PFTTGLIYDS  VMLKHQCSCG  DNSRHPEHAG  RIQSIWSRLQ  ERGLRSQCEC  LRGRKASLEE  900
 901  LQSVHSERHV  LLYGTNPLSR  LKLDNGKLAG  LLAQRMFVML  PCGGVGPLAT  LSAFLASLAP  TVPQGLSRVS  WGLKPPPGPN  PKSRPAPCPW  GPGRGVGTTP 1000
1001  LGPGSCVKPW  MRRALTLAPQ  VDTDTIWNEL  HSSNAARWAA  GSVTDLAFKV  ASRELKNGFA  VVRPPGHHAD  HSTAMGFCFF  NSVAIACRQL  QQQSKASKIL 1100
1101  IVDMDVHHGN  GTQQTFYQDP  SVLYISLHRH  DDGNFFPGSG  AVDEVGAGSG  EGFNVNVAWA  GGLDPPMGDP  EYLAAFRIVV  MPIAREFSPD  LVLVSAGFDA 1200
1201  AEGHPAPLGG  YHVSAKCFGY  MTQQLMNLAG  GAVVLALEGG  HDLTAICDAS  EACVAALLGN  RVDPLSEEGW  KQKPNLNAIR  SLEAVIRVHS  KCGDGTLAEL 1300
1301  RLKDLGGTLP  HRGQILGFRC  QPGDLLLVWS  KIPVSDPGSN  GEHPVRGYP   LSPPDGASRA  YQTVAPQGKY  WGCMQRLASC  PDSWVPRVPG  ADKEEVEAVT 1400
1401  ALASLSVGIL  AEDRPSEQLV  EEEEPMNL                                                                                     1428
         |    10      |    20      |    30      |    40      |    50      |    60      |    70      |    80      |    90      |   100
```

Fig. 6

```
cloned     1   . . . . . . . . . . . . . . . . . . . . . . . . . . . . . . . .
deduced    1   M F A R S A G L C F P W V P G V S H G G D A E E V L A Q H P T P T cloned     1   . . . . . . . . . . . . . . . . . . . . . . . . . . . . . . . .
deduced   34   G R G A E R R P R P P D S S A E G D P G M L K P C G C V P S P Q K cloned     1   . . . . . . . . . . . . . . . . . . . . . . . . . . . . . . . .
deduced   67   V A L K V G A P F C T C G C F Q R F H L P K A C P G Q Q G S P E S cloned     1   . . . . . . . . . . . . . . . . . . . . . . . . . . . . . . . .
deduced  100   A R P R N R Q P Y A T Q N G P A P R P Q V L P G S S S R C C H G Y cloned     1   . . . . . . . . . . . . . . . . . . . . . . . . . . . . . . . .
deduced  133   I C F L F D S S Q T A E V E V G W G G D T G S Q L R P L L R G A V cloned     1   . . . . . . . . . . . . . . . . . . . . . . . . . . . . . . . .
deduced  166   Y N S R M W D S Q K E D S K P D I L R L Q N T Q L F H S V S L S T cloned     1   . . . . . . . . . . . . . . . . . . . . . . . . . . . . . . . .
deduced  199   D G T Q V S P G A H Y C S P T G A G C P R P C A D T P G P Q P Q P cloned     1   . . . . . . . . . . . . . . . . . . . . . . . . . . . . . . . .
deduced  232   M D L R V G Q R P P V E P P P E P T L L A L Q R P Q R L H H H L F cloned     1   . . . . . . . . . . . . . . . . . . . . . . . . . . . . . . . .
deduced  265   L A G L Q Q Q R S V E P M R V K M E L P A C G A T L S L V P S L P cloned     1   . . . . . . . . . . . . . . . . . . . . . . . . . . . . . . . .
deduced  298   A F S I P R H Q S Q S S T P C P F L G C R P C P Q L S M D T P M P
```

Fig. 7

```
cloned     1    ------------------------------------
deduced  331    ELQVGPQEQELRQLLHKDKSKRSKEVATPAQPS cloned     1    ------------------------------------
deduced  364    PTSQVPAAACVACAVASSVVKQKLAEVILKKQQ cloned     1    ------------------------------------
deduced  397    AALERTVHPNSPGIPYRSQGPCSGQCPCSVPTP cloned     1    ------------------------------------
deduced  430    LKQPWHSFCRTLEPLETEGATRSMLSSFLPPVP cloned     1    ------------------------------------
deduced  463    SLPSDPPEHFPLRKTVSEPNLKLRYKPKKSLER cloned     1    ------------------------------------
deduced  496    RKNPLLRKESAPPSLRRRPAETLGDSSPSSSST cloned     1    ------------------------------------
deduced  529    PASGCSSPNDSEHGPNPILGSEALLGQRLRLQE cloned     1    ------------------------------------
deduced  562    TSVAPFALPTVSLLPAITLGLPAPARADSDRRT cloned     1    ------------------------------------
deduced  595    HPTLGPRGPILGSPHTPLFLPHGLEPEAGGTLP cloned     1    ------------------------------------
deduced  628    SRLQPILLLDPSGSHAPLLTVPGLGPLPFHFAQ
```

Fig. 7 (a)

```
cloned     1   . . . . . . . . . . . . . . . . . . . . . . . . . . . . .
deduced  661   S L M T T E R L S G S G L H W P L S R T R S E P L P P S A T A P P cloned     1   . . . . . . . . . E Q L K T H V Q V I K R S A K P S E K P R L R Q
deduced  694   P P G P M Q P R L E Q L K T H V Q V I K R S A K P S E K P R L R Q cloned    25   I P S A E D L E T D G G G P G Q V Y D D G L E H R E L G H G Q P E
deduced  727   I P S A E D L E T D G G G P G Q V Y D D G L E H R E L G H G Q P E cloned    58   A R G P A P L Q Q H P Q Y L L W E Q Q R L A G R L P R G S T G D T
deduced  760   A R G P A P L Q Q H P Q Y L L W E Q Q R L A G R L P R G S T G D T cloned    91   Y L L P L A Q G G H R P L S R A Q S S P A A P A S L S A P E P A S
deduced  793   Y L L P L A Q G G H R P L S R A Q S S P A A P A S L S A P E P A S cloned   124   Q A R V L S S S E T P A R T L P F T T G L I Y D S V M L K H Q C S
deduced  826   Q A R V L S S S E T P A R T L P F T T G L I Y D S V M L K H Q C S cloned   157   C G D N S R H P E H A G R I Q S I W S R L Q E R G L R S Q C E C L
deduced  859   C G D N S R H P E H A G R I Q S I W S R L Q E R G L R S Q C E C L cloned   190   R G R K A S L E E L Q S V H S E R H V L L Y G T N P L S R L K L D
deduced  892   R G R K A S L E E L Q S V H S E R H V L L Y G T N P L S R L K L D
```

Fig. 7 (b)

```
cloned    223   NGKLAGLLAQRMFYMLPCGGYG
deduced   925   NGKLAGLLAQRMFYMLPCGGYG PLATLSAFLAS cloned    245   . . . . . . . . . . . . . . . . . . . . . . .
deduced   958   LAPTYPQGLSRYSWGLKPPPGNPKSRPAPCPW cloned    245   . . . . . . . . . . . . . . . . . . . . . . . . . VDT
deduced   991   GPGRGVGTTPLGPGSCVKPWMMRALTLAPQ VDT cloned    248   DTIWNELHSSNAARWAAGSYTDLAFKVASRELK
deduced   1024  DTIWNELHSSNAARWAAGSYTDLAFKVASRELK cloned    281   NGFAVVRPPGHHADHSTAMGFCFFNSYAIACRQ
deduced   1057  NGFAVVRPPGHHADHSTAMGFCFFNSYAIACRQ cloned    314   LQQQSKASKILIYDWDVHHGNGTQQTFYQDPSV
deduced   1090  LQQQSKASKILIYDWDVHHGNGTQQTFYQDPSV cloned    347   LYISLHRHDDGNFFPGSGAVDEVGAGSGEGFNV
deduced   1123  LYISLHRHDDGNFFPGSGAVDEVGAGSGEGFNV cloned    380   NVAWAGGLDPPMGDPEYLAAFRIVVMPIAREFS
deduced   1156  NVAWAGGLDPPMGDPEYLAAFRIVVMPIAREFS
```

Fig. 7 (c)

```
cloned   413   PDLYLVSAGFDAAEGHPAPLGGYHVSAKCFGYM
deduced  1189  PDLYLVSAGFDAAEGHPAPLGGYHVSAKCFGYM cloned   446   TQQLMNLAGGAVVLALEGGHDLTAICDASEACV
deduced  1222  TQQLMNLAGGAVVLALEGGHDLTAICDASEACV cloned   479   AALLGNRVDPLSEEGWKQKPNLNSIRSLEAVIR
deduced  1255  AALLGNRVDPLSEEGWKQKPNLNAIRSLEAVIR cloned   512   VHS..............................
deduced  1288  VHSKCGDGTLAELRLKDLGGTLPHRGQILGFRC cloned   515   ..................................
deduced  1321  QPGDLLLVWSKIPVSDPGSNGEHPPVRGYPLSP cloned   515   ..............-KYWGCMQRLASCPDSWYP
deduced  1354  PDGASRAYQTVAPQGKYWGCMQRLASCPDSWYP cloned   533   RVPGADKEEVEAVTALASLSVGILAEDRPSEQL
deduced  1387  RVPGADKEEVEAVTALASLSVGILAEDRPSEQL cloned   566   VEEEEPMNL
deduced  1420  VEEEEPMNL
```

Fig. 7 (d)

```
227 PQPQPMDLRVGQR...PPVEP.....PPEPTLLALQRPQRLHHHLFLAGL 268
    |:  |||||: ::   |:||      :  |||||:: |:::::::::| :
 44 PSAVPMDLRLDHQFSLPVAEPALREQQLQQELLALKQKQQIQRQILIAEF 93

269 QQQRSV.........EPMRVKMELPACGATLSLVPSLPAFSIPRHQSQS 308
    |:|::            |  :: ::|: |    :|:     :: ||::::
 94 QRQHEQLSRQHEAQLHEHIKQQQEMLAMKHQQELLEH..QRKLERHRQEQ 141

309 STPCPFLGCRPCPQLSMDTPMPELQVGPQEQELRQLLHKDKSKRSKEVAT 358
                                ||:  :||:|:|| :|:|:|:|
142 ....................ELEKQHREQKLQQLKNKEKGKES..... 164

359 PAQPSPTSQVPAAACVACAVASSVVKQKLAEVILKKQQAALERTVHPNSP 408
                        ||||:  ||:||  |  :|:|::|   :|::
165 ...................AVASTEVKMKLQEFVLNKKKALAHRNL.... 191

409 GIPYRSQGPCSGQCPCSVPTPLKQPWHSFCRTLEPLETEGATR.SMLSSF 457
                                 : |  :|   || : |  |:::
192 .........................NHCISSDPRYWYGKTQHSSLDQS 214

458 LPPVPSLPS..........DPPEHFPLRKTVSEPNLKLRYKPK.KSLERR 496
    ||  :: :            |  : ||||||:|||||||| : | | |||
215 SPPQSGVSTSYNHPVLGMYDAKDDFPLRKTASEPNLKLRSRLKQVAERR 264

497 KNPLLRKESAP..PSLRRRPAETLGDSSPSSSSTPASGCSSPNDS..... 539
    ::||||:::::|    :|::|| ::    :: :  ||:|:|| ||||:|
265 SSPLLRRKDGPVVTALKKRPLDV...TDSACSSAPGSGPSSPNNSSGSVS 311

540 .EHGPNPILGS...EALLGQRLRLQETSVAPFALPTVSLLPAITLGLPA. 584
    |:|  |  :|   |: |:::||   :| |:::| | |     || ||||||
312 AENGIAPAVPSIPAETSLAHRLVAREGSAAPLPLYTSPSLPNITLGLPAT 361

585 ......PARADSDRRTHPTLGPRGPILGSPH.TPLFLPHGLEPEAGGTLP 627
          :: |::| | | |:|    |   | |: ||    || |:::
362 GPSAGTAGQQDTERLTLPALQQRLSLFPGTHLTPYLSTSPLERDGGAAHS 411

628 SRLQPILLLDPSGSHAPLLTVPGLGPLPFHFAQSLMTTERLSGS....GL 673
    ||  ::||:   ::|||:|   |||  ||:|  ||||   ::|:|  |
412 PLLQHMVLLEQPPAQAPLVT..GLGALPLH.AQSLVGADRVSPSIHKLRQ 458

674 HWPLSRTRSEPLPPSATAPPPPGPMQPRLEQLKTH........VQVIKRS 715
    |  ||:||  |||  :| |       :|:::|: |         :|: |
459 HRPLGRTQSAPLPQNAQALQHLVIQQQHQQFLEKHKQQFQQQQLQMNKII 508

716 AKPSE.................KPRLRQIPSAEDLETDGGGPG 741
    ||||                    :|  | ::|: ::  ::::|
509 PKPSEPARQPESHPEETEEELREHQALLDEPYLDRLPGQKEAHAQAG..V 556

742 QVVDDGLEHRELGHGQPEARGP...APLQQHP.........QVLLWEQQR 779
    ||  :: :| |     ||: |    | |::|         |:|| ||||
557 QVKQEPIESDE.....EEAEPPREVEPGQRQPSEQELLFRQQALLLEQQR 601

780 LAGRLPRGSTGDTVLLPLAQGGHRPLSRAQSSPA.APASLSAPEPASQAR 828
    :      :: ::: :|::   ||||||||||||||||  |   :|   ||   |
602 IHQLRNYQASMEAAGIPVSFGGHRPLSRAQSSPASATFPVSVQEPPTKPR 651

829 VLSSSETPARTLPFTTGLIYDSVMLKHQCSCGDNSRHPEHAGRIQSIWSR 878
                    |||||:||:||||||:|:::||||:| ||||||||||||||||||
652 .............FTTGLVYDTLMLKHQCTCGSSSSHPEHAGRIQSIWSR 688
```

Fig. 8

```
 879 LQERGLRSQCECLRGRKASLEELQSVHSERHVLLYGTNPLSRLKLDNGKL  928
     ||| |||::|||:|||||:|||||:|||| |:|||||||||:| |||: ||
 689 LQETGLRGKCECIRGRKATLEELQTVHSEAHTLLYGTNPLNRQKLDSKKL  738

929 AGLLAQRMFVMLPCGGVGPLATLSAFLASLAPTVPQGLSRVSWGLKPPPG  978
     | |||: :|| |||||||
 739 LGSLAS.VFVRLPCGGVG.............................   755

979 PNPKSRPAPCPWGPGRGVGTTPLGPGSCVKPWMMRALTLAPQVDTDTIWN 1028
                                                ||:|||||
 756 .........................................VDSDTIWN  763

1029 ELHSSNAARWAAGSVTDLAFKVASRELKNGFAVVRPPGHHADHSTAMGFC 1078
     |:||::||| |:| |::|:||||: ||||||||||||||||::|| ||||
 764 EVHSAGAARLAVGCVVELVFKVATGELKNGFAVVRPPGHHAEESTPMGFC  813

1079 FFNSVAIACRQLQQQSKASKILIVDWDVHHGNTQQTFYDPSVLYISLH  1128
     :|||||:|:: |||  ::|||||||||||||||||||:|:|||||||:|||
 814 YFNSVAVAAKLLQQRLSVSKILIVDWDVHHGNTQQAFYSDPSVLYMSLH  863

1129 RHDDGNFFPGSGAVDEVGAGSGEGFNVNVAWAGGLDPPMGDPEYLAAFRI 1178
     |:||||||||||| ||||:| | ||||:|::||||||||| |||||||
 864 RYDDGNFFPGSGAPDEVGTGPGVGFNVNMAFTGGLDPPMGDAEYLAAFRT  913

1179 VVMPIAREFSPDLVLVSAGFDAAEGHPAPLGGYHVSAKCFGYMTQQLMNL 1228
     |||||| ||:||:||||:||||:||||:||::||||||:|||||:|||:|
 914 VVMPIASEFAPDVVLVSSGFDAVEGHPTPLGGYNLSARCFGYLTKQLMGL  963

1229 AGGAVVLALEGGHDLTAICDASEACVAALLGNRVDPLSEEGWKQKPNLNA 1278
     ||| :|||||||||||||||||||||:|||||:||| |: :|:|| ||
 964 AGGRIVLALEGGHDLTAICDASEACVSALLGNELDPLPEKVLQQRPNANA 1013

1279 IRSLEAVIRVHSKCGDGTLAELRLKDLGGTLPHRGQILGFRCQPGDLLLV 1328
     :||:| |:::||
1014 VRSMEKVMEIHS.....................................  1025

1329 WSKIPVSDPGSNGEHPPVRGYPLSPPDGASRAYQTVAPQGKYWGCMQRLA 1378
                                              ||| |:||  :
1026 ...........................................KYWRCLQRTT 1035

1379 SCPDSWVPRVPGADKEEVEAVTALASLSVGIL.AEDRPSEQLVEEEEPM  1426
     |    : :: :::||:|:|||:||||||: || ||:|: :||| |:
1036 STAGRSLIEAQTCENEEAETVTAMASLSVGVKPAEKRPDEEPMEEEPPL  1084
```

Fig. 8 (a)

A
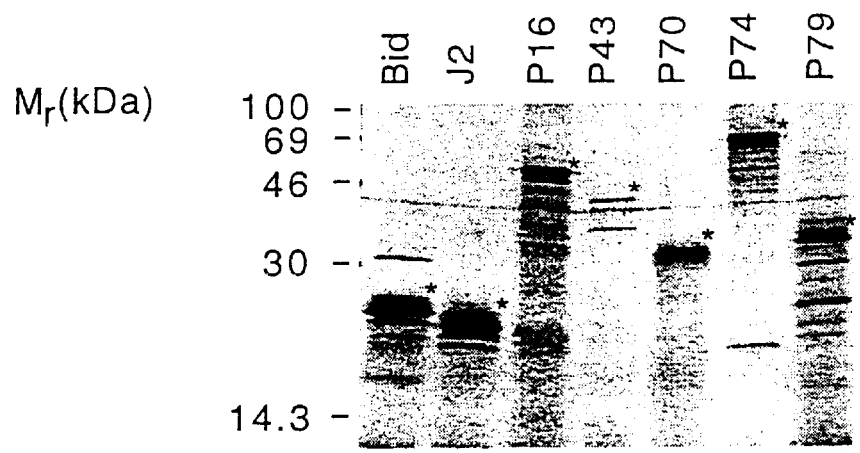
B
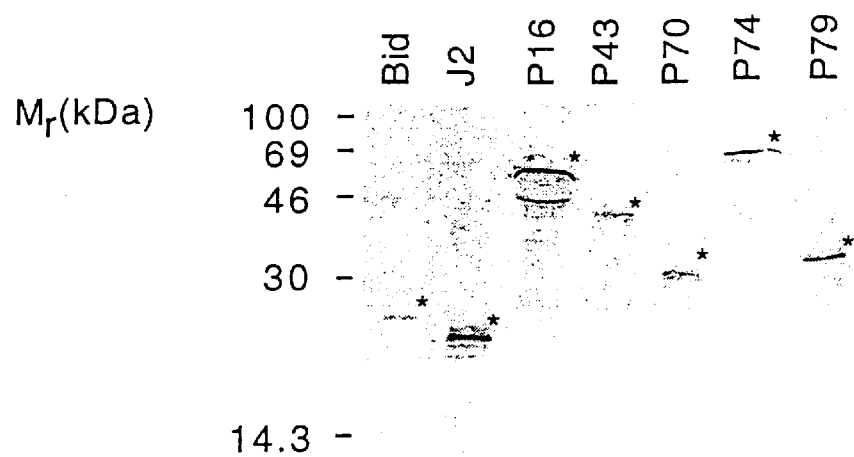
Fig. 9

SEQUENCE LISTING

<160> NUMBER OF SEQ ID NOS: 10

<210> SEQ ID NO 1
<211> LENGTH: 447
<212> TYPE: DNA
<213> ORGANISM: Homo sapiens -continued

```
<400> SEQUENCE: 1
cggcacgagg gcctgggcaa cggccggcac acgctgggac agcaggaagt ggaagtggac      60
ggtctgacgg cctacgtggc aggtgagcgc cctgacccac tgggtcccag gtcccagccc     120
gcatgccagg tggcccacga cccccccaga gcctgccctc tctgctctca aggcaccaag     180
acgctgagtg gcagcatagc cccaatgaac gtctgtgtcc gggcacttcc tgcaggccac     240
aggttcagca tgaagtcggc cttgaaggct gcatccttgc accccgccca gttgctgggg     300
ctggagaaga gtaaggggac cttgactttg gtgctgacgc agacttcgtg gtgctcgacg     360
actcccttca cgtccaggcc acctacatct cgggtgagct ggtgtggcag gcggacgcag     420
ctaggcagtg acaaggacct cggctga                                         447

<210> SEQ ID NO 2
<211> LENGTH: 148
<212> TYPE: PRT
<213> ORGANISM: Homo sapiens

<400> SEQUENCE: 2

Arg His Glu Gly Leu Gly Asn Gly Arg His Thr Leu Gly Gln Gln Glu
  1               5                  10                  15

Val Glu Val Asp Gly Leu Thr Ala Tyr Val Ala Gly Glu Arg Pro Asp
             20                  25                  30

Pro Leu Gly Pro Arg Ser Gln Pro Ala Cys Gln Val Ala His Asp Pro
         35                  40                  45

Pro Arg Ala Cys Pro Leu Cys Ser Gln Gly Thr Lys Thr Leu Ser Gly
     50                  55                  60

Ser Ile Ala Pro Met Asn Val Cys Val Arg Ala Leu Pro Ala Gly His
 65                  70                  75                  80

Arg Phe Ser Met Lys Ser Ala Leu Lys Ala Ala Ser Leu His Pro Ala
                 85                  90                  95

Gln Leu Leu Gly Leu Glu Lys Ser Lys Gly Thr Leu Thr Leu Val Leu
            100                 105                 110

Thr Gln Thr Ser Trp Cys Ser Thr Thr Pro Phe Thr Ser Arg Pro Pro
        115                 120                 125

Thr Ser Arg Val Ser Trp Cys Gly Arg Arg Thr Gln Leu Gly Ser Asp
    130                 135                 140

Lys Asp Leu Gly
145

<210> SEQ ID NO 3
<211> LENGTH: 1513
<212> TYPE: DNA
<213> ORGANISM: Homo sapiens

<400> SEQUENCE: 3
ggcgcggctc cgctctcggc tggggttcgt cactgggcgc gggatttggc cgccgcgggg      60
ctccggagcc gctcgctccc gacacggctc acgatgcgcg cgacagggc cggcgggggc      120 cccgtgctcc agttcactaa ctgccggatc ctgcgcggag ggaaactgct cagggaggat     180
ctgtgggtgc gcggaggccg catcttggac ccagagaagc tgttctttga ggagcggcgc     240
gtggccgacg agcggcggga ctgcggggc cgcatcttgg ctcccggatt catcgacgtg     300
cagatcaacc gtggatttgg tgttgacttc tctcaagcca cggaggacgt gggttcgggg     360
gttgccctcg tgcccggag gatcctgtcg cacggcgtca cctccttctg ccccacccctg     420 gtcacttccc caccggaggc ttatcacaag gttgttcctc agatccctgt gaagagtggt     480
```

```
ggtccccatg gggcagggt cctcgggctg cacctggagg gccccttcat cagccgggag    540
aagcggggcg cgcaccccga ggcccacctc cgctccttcg aggccgatgc cttccaggac    600
ttgctggcca cctacgggcc cctggacaat gtccgcatcg tgacgctggc cccagagttg    660
ggccgtagcc acgaagtgat ccgggcgctg acggcccgtg gcatctgcgt gtccctaggg    720
cactcagtgg ctgacctgcg ggcggcagag gatgctgtgt ggagcggagc caccttcatc    780
acccacctct tcaacgccat gctgcctttc caccaccgcg acccaggcat cgtggggctc    840
ctgaccagcg accggctgcc cgcaggccgc tgcatcttct atgggatgat gcagatggc    900 acgcacacca ccccgccgc cctgcggatc gcccaccgtg cccatcccca ggggctggtg    960
ctggtcaccg atgccatccc tgccttgggc ctgggcaacg ccggcacac gctgggacag   1020 caggaagtgg aagtggacgg tctgacggcc tacgtggcag gtgagcgccc tgacccactg   1080
ggtcccaggt cccagcccgc atgccaggtg gcccacgacc ccccagagc ctgccctctc   1140 tgctctcaag gcaccaagac gctgagtggc agcatagccc caatgaacgt ctgtgtccgg   1200
cacttcctgc aggccacagg ctgcagcatg gagtcggccc tggaggctgc atccctgcac   1260
cccgcccagt gctgggggct ggagaagagt aaggggaccc tggactttgg tgctgacgca   1320
gacttcgtgg tgctcgacga ctcccttcac gtccaggcca cctacatctc gggtgagctg   1380
gtgtggcagg cggacgcagc taggcagtga caaggacctc ggctgagagg cacctggcc   1440 gcagcgggat gccatcaggg ccgggtggtt ggggagctgg tctccaggga gtgagtcggg   1500
agccctgctg gat                                                      1513
```

<210> SEQ ID NO 4
<211> LENGTH: 502
<212> TYPE: PRT
<213> ORGANISM: Homo sapiens

<400> SEQUENCE: 4

```
Gly Ala Ala Pro Leu Ser Ala Gly Val Arg His Trp Ala Arg Asp Leu
 1               5                  10                  15

Ala Ala Ala Gly Leu Arg Ser Arg Ser Leu Pro Thr Arg Leu Thr Met
            20                  25                  30

Arg Gly Asp Arg Ala Gly Gly Pro Val Leu Gln Phe Thr Asn Cys
        35                  40                  45

Arg Ile Leu Arg Gly Gly Lys Leu Leu Arg Glu Asp Leu Trp Val Arg
    50                  55                  60

Gly Gly Arg Ile Leu Asp Pro Glu Lys Leu Phe Phe Glu Glu Arg Arg
65                  70                  75                  80

Val Ala Asp Glu Arg Arg Asp Cys Gly Gly Arg Ile Leu Ala Pro Gly
                85                  90                  95

Phe Ile Asp Val Gln Ile Asn Arg Gly Phe Gly Val Asp Phe Ser Gln
            100                 105                 110

Ala Thr Glu Asp Val Gly Ser Gly Val Ala Leu Val Ala Arg Arg Ile
        115                 120                 125

Leu Ser His Gly Val Thr Ser Phe Cys Pro Thr Leu Val Thr Ser Pro
    130                 135                 140

Pro Glu Ala Tyr His Lys Val Val Pro Gln Ile Pro Val Lys Ser Gly
145                 150                 155                 160

Gly Pro His Gly Ala Gly Val Leu Gly Leu His Leu Glu Gly Pro Phe
                165                 170                 175

Ile Ser Arg Glu Lys Arg Gly Ala His Pro Glu Ala His Leu Arg Ser
            180                 185                 190
```

```
Phe Glu Ala Asp Ala Phe Gln Asp Leu Leu Ala Thr Tyr Gly Pro Leu
        195                 200                 205
Asp Asn Val Arg Ile Val Thr Leu Ala Pro Glu Leu Gly Arg Ser His
    210                 215                 220
Glu Val Ile Arg Ala Leu Thr Ala Arg Gly Ile Cys Val Ser Leu Gly
225                 230                 235                 240
His Ser Val Ala Asp Leu Arg Ala Ala Glu Asp Ala Val Trp Ser Gly
                245                 250                 255
Ala Thr Phe Ile Thr His Leu Phe Asn Ala Met Leu Pro Phe His His
            260                 265                 270
Arg Asp Pro Gly Ile Val Gly Leu Leu Thr Ser Asp Arg Leu Pro Ala
        275                 280                 285
Gly Arg Cys Ile Phe Tyr Gly Met Ile Ala Asp Gly Thr His Thr Asn
    290                 295                 300
Pro Ala Ala Leu Arg Ile Ala His Arg Ala His Pro Gln Gly Leu Val
305                 310                 315                 320
Leu Val Thr Asp Ala Ile Pro Ala Leu Gly Leu Gly Asn Gly Arg His
                325                 330                 335
Thr Leu Gly Gln Gln Glu Val Glu Val Asp Gly Leu Thr Ala Tyr Val
            340                 345                 350
Ala Gly Glu Arg Pro Asp Pro Leu Gly Pro Arg Ser Gln Pro Ala Cys
        355                 360                 365
Gln Val Ala His Asp Pro Pro Arg Ala Cys Pro Leu Cys Ser Gln Gly
    370                 375                 380
Thr Lys Thr Leu Ser Gly Ser Ile Ala Pro Met Asn Val Cys Val Arg
385                 390                 395                 400
His Phe Leu Gln Ala Thr Gly Cys Ser Met Glu Ser Ala Leu Glu Ala
                405                 410                 415
Ala Ser Leu His Pro Ala Gln Leu Leu Gly Leu Glu Lys Ser Lys Gly
            420                 425                 430
Thr Leu Asp Phe Gly Ala Asp Ala Asp Phe Val Val Leu Asp Asp Ser
        435                 440                 445
Leu His Val Gln Ala Thr Tyr Ile Ser Gly Glu Leu Val Trp Gln Ala
    450                 455                 460
Asp Ala Ala Arg Gln Gln Gly Pro Arg Leu Arg Gly His Leu Ala Ala
465                 470                 475                 480
Ala Gly Cys His Gln Gly Arg Val Val Gly Glu Leu Val Ser Arg Glu
                485                 490                 495
Val Gly Ser Pro Ala Gly
            500

<210> SEQ ID NO 5
<211> LENGTH: 1725
<212> TYPE: DNA
<213> ORGANISM: Homo sapiens

<400> SEQUENCE: 5
gagcagctca aaactcacgt ccaggtgatc aagaggtcag ccaagccgag tgagaagccc      60
cggctgcggc agatacccctc ggctgaagac ctggagacag atggcggggg accgggccag    120
gtggtggacg atggcctgga gcacaggag ctgggccatg gcagcctga ggccagaggc       180 cccgctcctc tccagcagca ccctcaggtg ttgctctggg aacagcagcg actggctggg    240
cggctccccc gggcagcac cggggacact gtgctgcttc ctctggccca gggtgggcac     300
cggcctctgt cccgggctca gtcttcccca gccgcacctg cctcactgtc agccccagag    360
```

-continued

```
cctgccagcc aggcccgagt cctctccagc tcagagaccc ctgccaggac cctgcccttc      420
accacagggc tgatctatga ctcggtcatg ctgaagcacc agtgctcctg cggtgacaac      480
agcaggcacc cggagcacgc cggccgcatc cagagcatct ggtcccggct gcaggagcgg      540
gggctccgga gccagtgtga gtgtctccga ggccggaagg cctccctgga agagctgcag      600
tcggtccact ctgagcggca cgtgctcctc tacggcacca acccgctcag ccgcctcaaa      660
ctggacaacg ggaagctggc agggctcctg gcacagcgga tgtttgtgat gctgccctgt      720
ggtggggttg ggtggacac tgacaccatc tggaatgagc ttcattcctc caatgcagcc      780
cgctgggccg ctggcagtgt cactgacctc gccttcaaag tggcttctcg tgagctaaag      840
aatggtttcg ctgtggtgcg gcccccagga caccatgcag atcattcaac agccatgggc      900
ttctgcttct tcaactcagt ggccatcgcc tgccggcagc tgcaacagca gagcaaggcc      960
agcaagatcc tcattgtaga ctgggacgtg caccatggca acggcaccca gcaaaccttc     1020
taccaagacc ccagtgtgct ctacatctcc ctgcatcgcc atgacgacgg caacttcttc     1080
ccagggagtg gggctgtgga tgaggtaggg gctggcagcg tgagggcttc aatgtcaat     1140 gtggcctggg ctggaggtct ggacccccc atggggatc ctgagtacct ggctgctttc      1200
aggatagtcg tgatgcccat cgcccgagag ttctctccag acctagtcct ggtgtctgct     1260
ggatttgatg ctgctgaggg tcacccggcc ccactgggtg ctaccatgt ttctgccaaa      1320 tgttttggat acatgacgca gcaactgatg aacctggcag gaggcgcagt ggtgctggcc     1380
ttggagggtg gccatgacct cacagccatc tgtgacgcct ctgaggcctg tgtggctgct     1440
cttctgggta acaggggtgga tcccctttca gaagaaggct ggaaacagaa acccaacctc     1500
aattccatcc gctctctgga ggccgtgatc cgggtgcaca gtaaatactg gggctgcatg     1560
cagcgcctgg cctcctgtcc agactcctgg gtgcctagag tgccagggc tgacaaagaa      1620 gaagtggagg cagtaaccgc actggcgtcc ctctctgtgg gcatcctggc tgaagatagg     1680
ccctcggagc agctggtgga ggaggaagaa cctatgaatc tctaa                     1725
```

<210> SEQ ID NO 6
<211> LENGTH: 574
<212> TYPE: PRT
<213> ORGANISM: Homo sapiens

<400> SEQUENCE: 6

Glu Gln Leu Lys Thr His Val Gln Val Ile Lys Arg Ser Ala Lys Pro
 1               5                  10                  15

Ser Glu Lys Pro Arg Leu Arg Gln Ile Pro Ser Ala Glu Asp Leu Glu
                20                  25                  30

Thr Asp Gly Gly Gly Pro Gly Gln Val Val Asp Asp Gly Leu Glu His
            35                  40                  45

Arg Glu Leu Gly His Gly Gln Pro Glu Ala Arg Gly Pro Ala Pro Leu
        50                  55                  60

Gln Gln His Pro Gln Val Leu Leu Trp Glu Gln Gln Arg Leu Ala Gly
    65                  70                  75                  80

Arg Leu Pro Arg Gly Ser Thr Gly Asp Thr Val Leu Leu Pro Leu Ala
                85                  90                  95

Gln Gly Gly His Arg Pro Leu Ser Arg Ala Gln Ser Ser Pro Ala Ala
            100                 105                 110

Pro Ala Ser Leu Ser Ala Pro Glu Pro Ala Ser Gln Ala Arg Val Leu
        115                 120                 125

-continued

```
Ser Ser Ser Glu Thr Pro Ala Arg Thr Leu Pro Phe Thr Thr Gly Leu
130                 135                 140

Ile Tyr Asp Ser Val Met Leu Lys His Gln Cys Ser Cys Gly Asp Asn
145                 150                 155                 160

Ser Arg His Pro Glu His Ala Gly Arg Ile Gln Ser Ile Trp Ser Arg
                165                 170                 175

Leu Gln Glu Arg Gly Leu Arg Ser Gln Cys Glu Cys Leu Arg Gly Arg
            180                 185                 190

Lys Ala Ser Leu Glu Glu Leu Gln Ser Val His Ser Glu Arg His Val
        195                 200                 205

Leu Leu Tyr Gly Thr Asn Pro Leu Ser Arg Leu Lys Leu Asp Asn Gly
    210                 215                 220

Lys Leu Ala Gly Leu Leu Ala Gln Arg Met Phe Val Met Leu Pro Cys
225                 230                 235                 240

Gly Gly Val Gly Val Asp Thr Asp Thr Ile Trp Asn Glu Leu His Ser
                245                 250                 255

Ser Asn Ala Ala Arg Trp Ala Ala Gly Ser Val Thr Asp Leu Ala Phe
                260                 265                 270

Lys Val Ala Ser Arg Glu Leu Lys Asn Gly Phe Ala Val Val Arg Pro
            275                 280                 285

Pro Gly His His Ala Asp His Ser Thr Ala Met Gly Phe Cys Phe Phe
        290                 295                 300

Asn Ser Val Ala Ile Ala Cys Arg Gln Leu Gln Gln Gln Ser Lys Ala
305                 310                 315                 320

Ser Lys Ile Leu Ile Val Asp Trp Asp Val His His Gly Asn Gly Thr
                325                 330                 335

Gln Gln Thr Phe Tyr Gln Asp Pro Ser Val Leu Tyr Ile Ser Leu His
                340                 345                 350

Arg His Asp Asp Gly Asn Phe Phe Pro Gly Ser Gly Ala Val Asp Glu
            355                 360                 365

Val Gly Ala Gly Ser Gly Glu Gly Phe Asn Val Asn Val Ala Trp Ala
        370                 375                 380

Gly Gly Leu Asp Pro Pro Met Gly Asp Pro Glu Tyr Leu Ala Ala Phe
385                 390                 395                 400

Arg Ile Val Val Met Pro Ile Ala Arg Glu Phe Ser Pro Asp Leu Val
                405                 410                 415

Leu Val Ser Ala Gly Phe Asp Ala Ala Glu Gly His Pro Ala Pro Leu
                420                 425                 430

Gly Gly Tyr His Val Ser Ala Lys Cys Phe Gly Tyr Met Thr Gln Gln
            435                 440                 445

Leu Met Asn Leu Ala Gly Gly Ala Val Val Leu Ala Leu Glu Gly Gly
        450                 455                 460

His Asp Leu Thr Ala Ile Cys Asp Ala Ser Glu Ala Cys Val Ala Ala
465                 470                 475                 480

Leu Leu Gly Asn Arg Val Asp Pro Leu Ser Glu Glu Gly Trp Lys Gln
                485                 490                 495

Lys Pro Asn Leu Asn Ser Ile Arg Ser Leu Glu Ala Val Ile Arg Val
                500                 505                 510

His Ser Lys Tyr Trp Gly Cys Met Gln Arg Leu Ala Ser Cys Pro Asp
            515                 520                 525

Ser Trp Val Pro Arg Val Pro Gly Ala Asp Lys Glu Glu Val Glu Ala
        530                 535                 540
```

```
Val Thr Ala Leu Ala Ser Leu Ser Val Gly Ile Leu Ala Glu Asp Arg
545                 550                 555                 560

Pro Ser Glu Gln Leu Val Glu Glu Glu Pro Met Asn Leu
                565                 570
```

<210> SEQ ID NO 7
<211> LENGTH: 1428
<212> TYPE: PRT
<213> ORGANISM: Homo sapiens

<400> SEQUENCE: 7

```
Met Phe Ala Arg Ser Ala Gly Leu Cys Phe Pro Trp Val Pro Gly Val
  1               5                  10                  15

Ser His Gly Gly Asp Ala Glu Glu Val Leu Ala Gln His Pro Thr Pro
                 20                  25                  30

Thr Gly Arg Gly Ala Glu Arg Pro Arg Pro Pro Asp Ser Ser Ala
             35                  40                  45

Glu Gly Asp Pro Gly Met Leu Lys Pro Cys Gly Cys Val Pro Ser Pro
 50                  55                  60

Gln Lys Val Ala Leu Lys Val Gly Ala Pro Phe Cys Thr Cys Gly Cys
 65                  70                  75                  80

Phe Gln Arg Phe His Leu Pro Lys Ala Cys Pro Gly Gln Gln Gly Ser
                 85                  90                  95

Pro Glu Ser Ala Arg Pro Arg Asn Arg Gln Pro Tyr Ala Thr Gln Asn
            100                 105                 110

Gly Pro Ala Pro Arg Pro Gln Val Leu Pro Gly Ser Ser Arg Cys
        115                 120                 125

Cys His Gly Tyr Ile Cys Phe Leu Phe Asp Ser Ser Gln Thr Ala Glu
    130                 135                 140

Val Glu Val Gly Trp Gly Gly Asp Thr Gly Ser Gln Leu Arg Pro Leu
145                 150                 155                 160

Leu Arg Gly Ala Val Tyr Asn Ser Arg Met Trp Asp Ser Gln Lys Glu
                165                 170                 175

Asp Ser Lys Pro Asp Ile Leu Arg Leu Gln Asn Thr Gln Leu Phe His
            180                 185                 190

Ser Val Ser Leu Ser Thr Asp Gly Thr Gln Val Ser Pro Gly Ala His
        195                 200                 205

Tyr Cys Ser Pro Thr Gly Ala Gly Cys Pro Arg Pro Cys Ala Asp Thr
    210                 215                 220

Pro Gly Pro Gln Pro Gln Pro Met Asp Leu Arg Val Gly Gln Arg Pro
225                 230                 235                 240

Pro Val Glu Pro Pro Glu Pro Thr Leu Leu Ala Leu Gln Arg Pro
                245                 250                 255

Gln Arg Leu His His His Leu Phe Leu Ala Gly Leu Gln Gln Arg
            260                 265                 270

Ser Val Glu Pro Met Arg Val Lys Met Glu Leu Pro Ala Cys Gly Ala
        275                 280                 285

Thr Leu Ser Leu Val Pro Ser Leu Pro Ala Phe Ser Ile Pro Arg His
    290                 295                 300

Gln Ser Gln Ser Ser Thr Pro Cys Pro Phe Leu Gly Cys Arg Pro Cys
305                 310                 315                 320

Pro Gln Leu Ser Met Asp Thr Pro Met Pro Glu Leu Gln Val Gly Pro
                325                 330                 335

Gln Glu Gln Glu Leu Arg Gln Leu Leu His Lys Asp Lys Ser Lys Arg
            340                 345                 350
```

```
Ser Lys Glu Val Ala Thr Pro Ala Gln Pro Ser Pro Thr Ser Gln Val
        355                 360                 365

Pro Ala Ala Ala Cys Val Ala Cys Ala Val Ala Ser Ser Val Val Lys
370                 375                 380

Gln Lys Leu Ala Glu Val Ile Leu Lys Lys Gln Gln Ala Ala Leu Glu
385                 390                 395                 400

Arg Thr Val His Pro Asn Ser Pro Gly Ile Pro Tyr Arg Ser Gln Gly
                405                 410                 415

Pro Cys Ser Gly Gln Cys Pro Cys Ser Val Pro Thr Pro Leu Lys Gln
                420                 425                 430

Pro Trp His Ser Phe Cys Arg Thr Leu Glu Pro Leu Thr Glu Gly
        435                 440                 445

Ala Thr Arg Ser Met Leu Ser Ser Phe Leu Pro Val Pro Ser Leu
450                 455                 460

Pro Ser Asp Pro Pro Glu His Phe Pro Leu Arg Lys Thr Val Ser Glu
465                 470                 475                 480

Pro Asn Leu Lys Leu Arg Tyr Lys Pro Lys Lys Ser Leu Glu Arg Arg
                485                 490                 495

Lys Asn Pro Leu Leu Arg Lys Glu Ser Ala Pro Pro Ser Leu Arg Arg
                500                 505                 510

Arg Pro Ala Glu Thr Leu Gly Asp Ser Ser Pro Ser Ser Ser Ser Thr
                515                 520                 525

Pro Ala Ser Gly Cys Ser Ser Pro Asn Asp Ser Glu His Gly Pro Asn
530                 535                 540

Pro Ile Leu Gly Ser Glu Ala Leu Leu Gly Gln Arg Leu Arg Leu Gln
545                 550                 555                 560

Glu Thr Ser Val Ala Pro Phe Ala Leu Pro Thr Val Ser Leu Leu Pro
                565                 570                 575

Ala Ile Thr Leu Gly Leu Pro Ala Pro Ala Arg Ala Asp Ser Asp Arg
                580                 585                 590

Arg Thr His Pro Thr Leu Gly Pro Arg Gly Pro Ile Leu Gly Ser Pro
                595                 600                 605

His Thr Pro Leu Phe Leu Pro His Gly Leu Glu Pro Glu Ala Gly Gly
                610                 615                 620

Thr Leu Pro Ser Arg Leu Gln Pro Ile Leu Leu Asp Pro Ser Gly
625                 630                 635                 640

Ser His Ala Pro Leu Leu Thr Val Pro Gly Leu Gly Pro Leu Pro Phe
                645                 650                 655

His Phe Ala Gln Ser Leu Met Thr Thr Glu Arg Leu Ser Gly Ser Gly
                660                 665                 670

Leu His Trp Pro Leu Ser Arg Thr Arg Ser Glu Pro Leu Pro Pro Ser
                675                 680                 685

Ala Thr Ala Pro Pro Pro Gly Pro Met Gln Pro Arg Leu Glu Gln
                690                 695                 700

Leu Lys Thr His Val Gln Val Ile Lys Arg Ser Ala Lys Pro Ser Glu
705                 710                 715                 720

Lys Pro Arg Leu Arg Gln Ile Pro Ser Ala Glu Asp Leu Glu Thr Asp
                725                 730                 735

Gly Gly Gly Pro Gly Gln Val Val Asp Asp Gly Leu Glu His Arg Glu
                740                 745                 750

Leu Gly His Gly Gln Pro Glu Ala Arg Gly Pro Ala Pro Leu Gln Gln
                755                 760                 765
```

-continued

```
His Pro Gln Val Leu Leu Trp Glu Gln Gln Arg Leu Ala Gly Arg Leu
770                 775                 780

Pro Arg Gly Ser Thr Gly Asp Thr Val Leu Leu Pro Leu Ala Gln Gly
785                 790                 795                 800

Gly His Arg Pro Leu Ser Arg Ala Gln Ser Ser Pro Ala Ala Pro Ala
                805                 810                 815

Ser Leu Ser Ala Pro Glu Pro Ala Ser Gln Ala Arg Val Leu Ser Ser
            820                 825                 830

Ser Glu Thr Pro Ala Arg Thr Leu Pro Phe Thr Thr Gly Leu Ile Tyr
        835                 840                 845

Asp Ser Val Met Leu Lys His Gln Cys Ser Cys Gly Asp Asn Ser Arg
    850                 855                 860

His Pro Glu His Ala Gly Arg Ile Gln Ser Ile Trp Ser Arg Leu Gln
865                 870                 875                 880

Glu Arg Gly Leu Arg Ser Gln Cys Glu Cys Leu Arg Gly Arg Lys Ala
                885                 890                 895

Ser Leu Glu Glu Leu Gln Ser Val His Ser Glu Arg His Val Leu Leu
            900                 905                 910

Tyr Gly Thr Asn Pro Leu Ser Arg Leu Lys Leu Asp Asn Gly Lys Leu
        915                 920                 925

Ala Gly Leu Leu Ala Gln Arg Met Phe Val Met Leu Pro Cys Gly Gly
    930                 935                 940

Val Gly Pro Leu Ala Thr Leu Ser Ala Phe Leu Ala Ser Leu Ala Pro
945                 950                 955                 960

Thr Val Pro Gln Gly Leu Ser Arg Val Ser Trp Gly Leu Lys Pro Pro
                965                 970                 975

Pro Gly Pro Asn Pro Lys Ser Arg Pro Ala Pro Cys Pro Trp Gly Pro
            980                 985                 990

Gly Arg Gly Val Gly Thr Thr Pro Leu Gly Pro Gly Ser Cys Val Lys
        995                 1000                1005

Pro Trp Met Met Arg Ala Leu Thr Leu Ala Pro Gln Val Asp Thr Asp
    1010                1015                1020

Thr Ile Trp Asn Glu Leu His Ser Ser Asn Ala Ala Arg Trp Ala Ala
1025                1030                1035                1040

Gly Ser Val Thr Asp Leu Ala Phe Lys Val Ala Ser Arg Glu Leu Lys
                1045                1050                1055

Asn Gly Phe Ala Val Val Arg Pro Pro Gly His His Ala Asp His Ser
            1060                1065                1070

Thr Ala Met Gly Phe Cys Phe Phe Asn Ser Val Ala Ile Ala Cys Arg
        1075                1080                1085

Gln Leu Gln Gln Gln Ser Lys Ala Ser Lys Ile Leu Ile Val Asp Trp
    1090                1095                1100

Asp Val His His Gly Asn Gly Thr Gln Gln Thr Phe Tyr Gln Asp Pro
1105                1110                1115                1120

Ser Val Leu Tyr Ile Ser Leu His Arg His Asp Asp Gly Asn Phe Phe
                1125                1130                1135

Pro Gly Ser Gly Ala Val Asp Glu Val Gly Ala Gly Ser Gly Glu Gly
            1140                1145                1150

Phe Asn Val Asn Val Ala Trp Ala Gly Gly Leu Asp Pro Pro Met Gly
        1155                1160                1165

Asp Pro Glu Tyr Leu Ala Ala Phe Arg Ile Val Val Met Pro Ile Ala
    1170                1175                1180
```

-continued

```
Arg Glu Phe Ser Pro Asp Leu Val Leu Val Ser Ala Gly Phe Asp Ala
1185                1190                1195                1200

Ala Glu Gly His Pro Ala Pro Leu Gly Gly Tyr His Val Ser Ala Lys
            1205                1210                1215

Cys Phe Gly Tyr Met Thr Gln Gln Leu Met Asn Leu Ala Gly Gly Ala
        1220                1225                1230

Val Val Leu Ala Leu Glu Gly Gly His Asp Leu Thr Ala Ile Cys Asp
1235                1240                1245

Ala Ser Glu Ala Cys Val Ala Ala Leu Leu Gly Asn Arg Val Asp Pro
    1250                1255                1260

Leu Ser Glu Glu Gly Trp Lys Gln Lys Pro Asn Leu Asn Ala Ile Arg
1265                1270                1275                1280

Ser Leu Glu Ala Val Ile Arg Val His Ser Lys Cys Gly Asp Gly Thr
            1285                1290                1295

Leu Ala Glu Leu Arg Leu Lys Asp Leu Gly Gly Thr Leu Pro His Arg
        1300                1305                1310

Gly Gln Ile Leu Gly Phe Arg Cys Gln Pro Gly Asp Leu Leu Leu Val
    1315                1320                1325

Trp Ser Lys Ile Pro Val Ser Asp Pro Gly Ser Asn Gly Glu His Pro
1330                1335                1340

Pro Val Arg Gly Tyr Pro Leu Ser Pro Pro Asp Gly Ala Ser Arg Ala
1345                1350                1355                1360

Tyr Gln Thr Val Ala Pro Gln Gly Lys Tyr Trp Gly Cys Met Gln Arg
            1365                1370                1375

Leu Ala Ser Cys Pro Asp Ser Trp Val Pro Arg Val Pro Gly Ala Asp
        1380                1385                1390

Lys Glu Glu Val Glu Ala Val Thr Ala Leu Ala Ser Leu Ser Val Gly
            1395                1400                1405

Ile Leu Ala Glu Asp Arg Pro Ser Glu Gln Leu Val Glu Glu Glu Glu
    1410                1415                1420

Pro Met Asn Leu
1425

<210> SEQ ID NO 8
<211> LENGTH: 1200
<212> TYPE: PRT
<213> ORGANISM: Homo sapiens

<400> SEQUENCE: 8

Pro Gln Pro Gln Pro Met Asp Leu Arg Val Gly Gln Arg Pro Pro Val
1               5                   10                  15

Glu Pro Pro Pro Glu Pro Thr Leu Leu Ala Leu Gln Arg Pro Gln Arg
            20                  25                  30

Leu His His His Leu Phe Leu Ala Gly Leu Gln Gln Gln Arg Ser Val
        35                  40                  45

Glu Pro Met Arg Val Lys Met Glu Leu Pro Ala Cys Gly Ala Thr Leu
    50                  55                  60

Ser Leu Val Pro Ser Leu Pro Ala Phe Ser Ile Pro Arg His Gln Ser
65                  70                  75                  80

Gln Ser Ser Thr Pro Cys Pro Phe Leu Gly Cys Arg Pro Cys Pro Gln
                85                  90                  95

Leu Ser Met Asp Thr Pro Met Pro Glu Leu Gln Val Gly Pro Gln Glu
            100                 105                 110

Gln Glu Leu Arg Gln Leu Leu His Lys Asp Lys Ser Lys Arg Ser Lys
        115                 120                 125
```

-continued

```
Glu Val Ala Thr Pro Ala Gln Pro Ser Pro Thr Ser Gln Val Pro Ala
130                 135                 140

Ala Ala Cys Val Ala Cys Ala Val Ala Ser Ser Val Val Lys Gln Lys
145                 150                 155                 160

Leu Ala Glu Val Ile Leu Lys Lys Gln Gln Ala Ala Leu Glu Arg Thr
                165                 170                 175

Val His Pro Asn Ser Pro Gly Ile Pro Tyr Arg Ser Gln Gly Pro Cys
            180                 185                 190

Ser Gly Gln Cys Pro Cys Ser Val Pro Thr Pro Leu Lys Gln Pro Trp
        195                 200                 205

His Ser Phe Cys Arg Thr Leu Glu Pro Leu Glu Thr Glu Gly Ala Thr
    210                 215                 220

Arg Ser Met Leu Ser Ser Phe Leu Pro Pro Val Pro Ser Leu Pro Ser
225                 230                 235                 240

Asp Pro Pro Glu His Phe Pro Leu Arg Lys Thr Val Ser Glu Pro Asn
                245                 250                 255

Leu Lys Leu Arg Tyr Lys Pro Lys Lys Ser Leu Glu Arg Arg Lys Asn
                260                 265                 270

Pro Leu Leu Arg Lys Glu Ser Ala Pro Pro Ser Leu Arg Arg Arg Pro
            275                 280                 285

Ala Glu Thr Leu Gly Asp Ser Ser Pro Ser Ser Ser Ser Thr Pro Ala
290                 295                 300

Ser Gly Cys Ser Ser Pro Asn Asp Ser Glu His Gly Pro Asn Pro Ile
305                 310                 315                 320

Leu Gly Ser Glu Ala Leu Leu Gly Gln Arg Leu Arg Leu Gln Glu Thr
                325                 330                 335

Ser Val Ala Pro Phe Ala Leu Pro Thr Val Ser Leu Leu Pro Ala Ile
            340                 345                 350

Thr Leu Gly Leu Pro Ala Pro Ala Arg Ala Asp Ser Asp Arg Arg Thr
        355                 360                 365

His Pro Thr Leu Gly Pro Arg Gly Pro Ile Leu Gly Ser Pro His Thr
    370                 375                 380

Pro Leu Phe Leu Pro His Gly Leu Glu Pro Glu Ala Gly Gly Thr Leu
385                 390                 395                 400

Pro Ser Arg Leu Gln Pro Ile Leu Leu Leu Asp Pro Ser Gly Ser His
                405                 410                 415

Ala Pro Leu Leu Thr Val Pro Gly Leu Gly Pro Leu Pro Phe His Phe
                420                 425                 430

Ala Gln Ser Leu Met Thr Thr Glu Arg Leu Ser Gly Ser Gly Leu His
            435                 440                 445

Trp Pro Leu Ser Arg Thr Arg Ser Glu Pro Leu Pro Pro Ser Ala Thr
        450                 455                 460

Ala Pro Pro Pro Gly Pro Met Gln Pro Arg Leu Glu Gln Leu Lys
465                 470                 475                 480

Thr His Val Gln Val Ile Lys Arg Ser Ala Lys Pro Ser Glu Lys Pro
                485                 490                 495

Arg Leu Arg Gln Ile Pro Ser Ala Glu Asp Leu Glu Thr Asp Gly Gly
            500                 505                 510

Gly Pro Gly Gln Val Val Asp Asp Gly Leu Glu His Arg Glu Leu Gly
        515                 520                 525

His Gly Gln Pro Glu Ala Arg Gly Pro Ala Pro Leu Gln Gln His Pro
    530                 535                 540
```

-continued

```
Gln Val Leu Leu Trp Glu Gln Arg Leu Ala Gly Arg Leu Pro Arg
545                 550                 555                 560

Gly Ser Thr Gly Asp Thr Val Leu Leu Pro Leu Ala Gln Gly Gly His
                565                 570                 575

Arg Pro Leu Ser Arg Ala Gln Ser Ser Pro Ala Pro Ala Ser Leu
            580                 585                 590

Ser Ala Pro Glu Pro Ala Ser Gln Ala Arg Val Leu Ser Ser Ser Glu
        595                 600                 605

Thr Pro Ala Arg Thr Leu Pro Phe Thr Thr Gly Leu Ile Tyr Asp Ser
    610                 615                 620

Val Met Leu Lys His Gln Cys Ser Cys Gly Asp Asn Ser Arg His Pro
625                 630                 635                 640

Glu His Ala Gly Arg Ile Gln Ser Ile Trp Ser Arg Leu Gln Glu Arg
                645                 650                 655

Gly Leu Arg Ser Gln Cys Glu Cys Leu Arg Gly Arg Lys Ala Ser Leu
            660                 665                 670

Glu Glu Leu Gln Ser Val His Ser Glu Arg His Val Leu Leu Tyr Gly
        675                 680                 685

Thr Asn Pro Leu Ser Arg Leu Lys Leu Asp Asn Gly Lys Leu Ala Gly
    690                 695                 700

Leu Leu Ala Gln Arg Met Phe Val Met Leu Pro Cys Gly Gly Val Gly
705                 710                 715                 720

Pro Leu Ala Thr Leu Ser Ala Phe Leu Ala Ser Leu Ala Pro Thr Val
                725                 730                 735

Pro Gln Gly Leu Ser Arg Val Ser Trp Gly Leu Lys Pro Pro Pro Gly
            740                 745                 750

Pro Asn Pro Lys Ser Arg Pro Ala Pro Cys Pro Trp Gly Pro Gly Arg
        755                 760                 765

Gly Val Gly Thr Thr Pro Leu Gly Pro Gly Ser Cys Val Lys Pro Trp
    770                 775                 780

Met Met Arg Ala Leu Thr Leu Ala Pro Gln Val Asp Thr Asp Thr Ile
785                 790                 795                 800

Trp Asn Glu Leu His Ser Ser Asn Ala Ala Arg Trp Ala Ala Gly Ser
                805                 810                 815

Val Thr Asp Leu Ala Phe Lys Val Ala Ser Arg Glu Leu Lys Asn Gly
            820                 825                 830

Phe Ala Val Val Arg Pro Pro Gly His His Ala Asp His Ser Thr Ala
        835                 840                 845

Met Gly Phe Cys Phe Phe Asn Ser Val Ala Ile Ala Cys Arg Gln Leu
    850                 855                 860

Gln Gln Gln Ser Lys Ala Ser Lys Ile Leu Ile Val Asp Trp Asp Val
865                 870                 875                 880

His His Gly Asn Gly Thr Gln Gln Thr Phe Tyr Gln Asp Pro Ser Val
                885                 890                 895

Leu Tyr Ile Ser Leu His Arg His Asp Asp Gly Asn Phe Phe Pro Gly
            900                 905                 910

Ser Gly Ala Val Asp Glu Val Gly Ala Gly Ser Gly Glu Gly Phe Asn
        915                 920                 925

Val Asn Val Ala Trp Ala Gly Gly Leu Asp Pro Pro Met Gly Asp Pro
    930                 935                 940

Glu Tyr Leu Ala Ala Phe Arg Ile Val Val Met Pro Ile Ala Arg Glu
945                 950                 955                 960
```

```
Phe Ser Pro Asp Leu Val Leu Val Ser Ala Gly Phe Asp Ala Ala Glu
                965                 970                 975

Gly His Pro Ala Pro Leu Gly Gly Tyr His Val Ser Ala Lys Cys Phe
            980                 985                 990

Gly Tyr Met Thr Gln Gln Leu Met Asn Leu Ala Gly Gly Ala Val Val
        995                1000                1005

Leu Ala Leu Glu Gly Gly His Asp Leu Thr Ala Ile Cys Asp Ala Ser
    1010                1015                1020

Glu Ala Cys Val Ala Ala Leu Leu Gly Asn Arg Val Asp Pro Leu Ser
1025                1030                1035                1040

Glu Glu Gly Trp Lys Gln Lys Pro Asn Leu Asn Ala Ile Arg Ser Leu
                1045                1050                1055

Glu Ala Val Ile Arg Val His Ser Lys Cys Gly Asp Gly Thr Leu Ala
            1060                1065                1070

Glu Leu Arg Leu Lys Asp Leu Gly Gly Thr Leu Pro His Arg Gly Gln
        1075                1080                1085

Ile Leu Gly Phe Arg Cys Gln Pro Gly Asp Leu Leu Leu Val Trp Ser
    1090                1095                1100

Lys Ile Pro Val Ser Asp Pro Gly Ser Asn Gly Glu His Pro Pro Val
1105                1110                1115                1120

Arg Gly Tyr Pro Leu Ser Pro Pro Asp Gly Ala Ser Arg Ala Tyr Gln
                1125                1130                1135

Thr Val Ala Pro Gln Gly Lys Tyr Trp Gly Cys Met Gln Arg Leu Ala
            1140                1145                1150

Ser Cys Pro Asp Ser Trp Val Pro Arg Val Pro Gly Ala Asp Lys Glu
        1155                1160                1165

Glu Val Glu Ala Val Thr Ala Leu Ala Ser Leu Ser Val Gly Ile Leu
    1170                1175                1180

Ala Glu Asp Arg Pro Ser Glu Gln Leu Val Glu Glu Glu Pro Met
1185                1190                1195                1200

<210> SEQ ID NO 9
<211> LENGTH: 1041
<212> TYPE: PRT
<213> ORGANISM: Homo sapiens

<400> SEQUENCE: 9

Pro Ser Ala Val Pro Met Asp Leu Arg Leu Asp His Gln Phe Ser Leu
 1               5                  10                  15

Pro Val Ala Glu Pro Ala Leu Arg Glu Gln Gln Leu Gln Gln Glu Leu
            20                  25                  30

Leu Ala Leu Lys Gln Lys Gln Gln Ile Gln Arg Gln Ile Leu Ile Ala
        35                  40                  45

Glu Phe Gln Arg Gln His Glu Gln Leu Ser Arg Gln His Glu Ala Gln
    50                  55                  60

Leu His Glu His Ile Lys Gln Gln Gln Glu Met Leu Ala Met Lys His
65                  70                  75                  80

Gln Gln Glu Leu Leu Glu His Gln Arg Lys Leu Glu Arg His Arg Gln
                85                  90                  95

Glu Gln Glu Leu Glu Lys Gln His Arg Glu Gln Lys Leu Gln Gln Leu
            100                 105                 110

Lys Asn Lys Glu Lys Gly Lys Glu Ser Ala Val Ala Ser Thr Glu Val
        115                 120                 125

Lys Met Lys Leu Gln Glu Phe Val Leu Asn Lys Lys Ala Leu Ala
    130                 135                 140
```

-continued

```
His Arg Asn Leu Asn His Cys Ile Ser Ser Asp Pro Arg Tyr Trp Tyr
145                 150                 155                 160

Gly Lys Thr Gln His Ser Ser Leu Asp Gln Ser Ser Pro Pro Gln Ser
                165                 170                 175

Gly Val Ser Thr Ser Tyr Asn His Pro Val Leu Gly Met Tyr Asp Ala
            180                 185                 190

Lys Asp Asp Phe Pro Leu Arg Lys Thr Ala Ser Glu Pro Asn Leu Lys
        195                 200                 205

Leu Arg Ser Arg Leu Lys Gln Lys Val Ala Glu Arg Ser Ser Pro
    210                 215                 220

Leu Leu Arg Arg Lys Asp Gly Pro Val Val Thr Ala Leu Lys Lys Arg
225                 230                 235                 240

Pro Leu Asp Val Thr Asp Ser Ala Cys Ser Ser Ala Pro Gly Ser Gly
                245                 250                 255

Pro Ser Ser Pro Asn Asn Ser Ser Gly Ser Val Ser Ala Glu Asn Gly
                260                 265                 270

Ile Ala Pro Ala Val Pro Ser Ile Pro Ala Glu Thr Ser Leu Ala His
            275                 280                 285

Arg Leu Val Ala Arg Glu Gly Ser Ala Ala Pro Leu Pro Leu Tyr Thr
        290                 295                 300

Ser Pro Ser Leu Pro Asn Ile Thr Leu Gly Leu Pro Ala Thr Gly Pro
305                 310                 315                 320

Ser Ala Gly Thr Ala Gly Gln Gln Asp Thr Glu Arg Leu Thr Leu Pro
                325                 330                 335

Ala Leu Gln Gln Arg Leu Ser Leu Phe Pro Gly Thr His Leu Thr Pro
                340                 345                 350

Tyr Leu Ser Thr Ser Pro Leu Glu Arg Asp Gly Gly Ala Ala His Ser
            355                 360                 365

Pro Leu Leu Gln His Met Val Leu Leu Glu Gln Pro Pro Ala Gln Ala
        370                 375                 380

Pro Leu Val Thr Gly Leu Gly Ala Leu Pro Leu His Ala Gln Ser Leu
385                 390                 395                 400

Val Gly Ala Asp Arg Val Ser Pro Ser Ile His Lys Leu Arg Gln His
                405                 410                 415

Arg Pro Leu Gly Arg Thr Gln Ser Ala Pro Leu Pro Gln Asn Ala Gln
                420                 425                 430

Ala Leu Gln His Leu Val Ile Gln Gln Gln His Gln Phe Leu Glu
            435                 440                 445

Lys His Lys Gln Gln Phe Gln Gln Gln Leu Gln Met Asn Lys Ile
    450                 455                 460

Ile Pro Lys Pro Ser Glu Pro Ala Arg Gln Pro Glu Ser His Pro Glu
465                 470                 475                 480

Glu Thr Glu Glu Glu Leu Arg Glu His Gln Ala Leu Leu Asp Glu Pro
                485                 490                 495

Tyr Leu Asp Arg Leu Pro Gly Gln Lys Glu Ala His Ala Gln Ala Gly
            500                 505                 510

Val Gln Val Lys Gln Glu Pro Ile Glu Ser Asp Glu Glu Ala Glu
        515                 520                 525

Pro Pro Arg Glu Val Glu Pro Gly Gln Arg Gln Pro Ser Glu Gln Glu
        530                 535                 540

Leu Leu Phe Arg Gln Gln Ala Leu Leu Leu Glu Gln Gln Arg Ile His
545                 550                 555                 560
```

```
-continued

Gln Leu Arg Asn Tyr Gln Ala Ser Met Glu Ala Ala Gly Ile Pro Val
                565                 570                 575

Ser Phe Gly Gly His Arg Pro Leu Ser Arg Ala Gln Ser Ser Pro Ala
            580                 585                 590

Ser Ala Thr Phe Pro Val Ser Val Gln Glu Pro Pro Thr Lys Pro Arg
        595                 600                 605

Phe Thr Thr Gly Leu Val Tyr Asp Thr Leu Met Leu Lys His Gln Cys
    610                 615                 620

Thr Cys Gly Ser Ser Ser His Pro Glu His Ala Gly Arg Ile Gln
625                 630                 635                 640

Ser Ile Trp Ser Arg Leu Gln Glu Thr Gly Leu Arg Gly Lys Cys Glu
            645                 650                 655

Cys Ile Arg Gly Arg Lys Ala Thr Leu Glu Glu Leu Gln Thr Val His
                660                 665                 670

Ser Glu Ala His Thr Leu Leu Tyr Gly Thr Asn Pro Leu Asn Arg Gln
            675                 680                 685

Lys Leu Asp Ser Lys Lys Leu Leu Gly Ser Leu Ala Ser Val Phe Val
690                 695                 700

Arg Leu Pro Cys Gly Val Gly Val Asp Ser Asp Thr Ile Trp Asn
705                 710                 715                 720

Glu Val His Ser Ala Gly Ala Ala Arg Leu Ala Val Gly Cys Val Val
                725                 730                 735

Glu Leu Val Phe Lys Val Ala Thr Gly Glu Leu Lys Asn Gly Phe Ala
            740                 745                 750

Val Val Arg Pro Pro Gly His His Ala Glu Glu Ser Thr Pro Met Gly
            755                 760                 765

Phe Cys Tyr Phe Asn Ser Val Ala Val Ala Ala Lys Leu Leu Gln Gln
    770                 775                 780

Arg Leu Ser Val Ser Lys Ile Leu Ile Val Asp Trp Asp Val His His
785                 790                 795                 800

Gly Asn Gly Thr Gln Gln Ala Phe Tyr Ser Asp Pro Ser Val Leu Tyr
                805                 810                 815

Met Ser Leu His Arg Tyr Asp Asp Gly Asn Phe Phe Pro Gly Ser Gly
            820                 825                 830

Ala Pro Asp Glu Val Gly Thr Gly Pro Gly Val Gly Phe Asn Val Asn
            835                 840                 845

Met Ala Phe Thr Gly Gly Leu Asp Pro Pro Met Gly Asp Ala Glu Tyr
    850                 855                 860

Leu Ala Ala Phe Arg Thr Val Val Met Pro Ile Ala Ser Glu Phe Ala
865                 870                 875                 880

Pro Asp Val Val Leu Val Ser Ser Gly Phe Asp Ala Val Glu Gly His
                885                 890                 895

Pro Thr Pro Leu Gly Gly Tyr Asn Leu Ser Ala Arg Cys Phe Gly Tyr
            900                 905                 910

Leu Thr Lys Gln Leu Met Gly Leu Ala Gly Gly Arg Ile Val Leu Ala
        915                 920                 925

Leu Glu Gly Gly His Asp Leu Thr Ala Ile Cys Asp Ala Ser Glu Ala
    930                 935                 940

Cys Val Ser Ala Leu Leu Gly Asn Glu Leu Asp Pro Leu Pro Glu Lys
945                 950                 955                 960

Val Leu Gln Gln Arg Pro Asn Ala Asn Ala Val Arg Ser Met Glu Lys
                965                 970                 975
```

```
-continued

Val Met Glu Ile His Ser Lys Tyr Trp Arg Cys Leu Gln Arg Thr Thr
            980             985             990

Ser Thr Ala Gly Arg Ser Leu Ile Glu Ala Gln Thr Cys Glu Asn Glu
        995             1000            1005

Glu Ala Glu Thr Val Thr Ala Met Ala Ser Leu Ser Val Gly Val Lys
    1010            1015            1020

Pro Ala Glu Lys Arg Pro Asp Glu Glu Pro Met Glu Glu Glu Pro Pro
1025            1030            1035            1040

Leu

<210> SEQ ID NO 10
<211> LENGTH: 16
<212> TYPE: DNA
<213> ORGANISM: Artificial
<220> FEATURE:
<223> OTHER INFORMATION: synthetic

<400> SEQUENCE: 10
ggggsggggs ggggsg                                                      16
```

US 6,762,283 B1

CASPASE-8 INTERACTING PROTEINS

CROSS-REFERENCE TO RELATED APPLICATIONS

This application is a continuation-in-part of copending parent application No. PCT/IL99/00698, filed Dec. 23, 1999, the entire contents of which are hereby incorporated herein by reference.

FIELD OF THE INVENTION

The present invention is generally in the field of cysteine proteases. More specifically, the invention concerns proteins which interact with caspase-8 (MACH) and/or modulate its function in the cell death (or apoptotic) pathways mediated by CD95 (Fas/Apo-1) or by CD120a (p55-TNF receptor).

In particular, the present invention concerns proteins which interact with caspase-8/MACH directly or indirectly. The invention also relates to the preparation and use of the caspase-8/MACH interacting proteins.

BACKGROUND OF THE INVENTION

Tumor Necrosis Factor (TNF-alpha) and Lymphotoxin (TNF-beta) (hereinafter, TNF, refers to both TNF-alpha and TNF-beta) are multifunctional pro-inflammatory cytokines formed mainly by mononuclear phagocytes, which have many effects on cells (Wallach, D. (1986) In: *Interferon 7* (Ion Gresser, ed.), pp. 83–122, Academic Press, London; and Beutler and Cerami (1987)). Both TNF-alpha and TNF-beta initiate their effects by binding to specific cell surface receptors. Some of the effects are likely to be beneficial to the organism: they may destroy, for example, tumor cells or virus infected cells and augment antibacterial activities of granulocytes. In this way, TNF contributes to the defense of the organism against tumors and infectious agents and contributes to the recovery from injury. Thus, TNF can be used as an anti-tumor agent in which application it binds to its receptors on the surface of tumor cells and thereby initiates the events leading to the death of the tumor cells. TNF can also be used as an anti-infectious agent.

However, both TNF-alpha and TNF-beta also have deleterious effects. There is evidence that overproduction of TNF-alpha may play a major pathogenic role in several diseases. For example, effects of TNF-alpha, primarily on the vasculature, are known to be a major cause for symptoms of septic shock (Tracey et al, 1986). In some diseases, TNF may cause excessive loss of weight (cachexia) by suppressing activities of adipocytes and by causing anorexia, and TNF-alpha was thus called cachectin. It was also described as a mediator of the damage to tissues in rheumatic diseases (Beutler and Cerami, 1987) and as a major mediator of the damage observed in graft-versus-host reactions (Piquet et al., 1987). In addition, TNF is known to be involved in the process of inflammation and in many other diseases.

Two distinct, independently expressed, receptors, the p55 (CD120a) and the p75 (CD120b) TNF-Rs, which bind both TNF-alpha and TNF-beta specifically, initiate and/or mediate the above noted biological effects of TNF. These two receptors have structurally dissimilar intracellular domains suggesting that they signal differently (See Hohmann et al., 1989; Engelmann et al., 1990; Brockhaus et al., 1990; Loetscher et al., 1990; Schall et al., 1990; Nophar et al., 1990; Smith et al., 1990; and Holler et al., 1990). However, the cellular mechanisms, for example, the various proteins and possibly other factors, which are involved in the intracellular signaling of the CD120a and CD120b have yet to be elucidated. It is intracellular signaling, which occurs usually after the binding of the ligand, i.e., TNF (alpha or beta), to the receptor, that is responsible for the commencement of the cascade of reactions that ultimately result in the observed response of the cell to TNF.

As regards the above-mentioned cytocidal effect of TNF, in most cells studied so far, this effect is triggered mainly by CD120a. Antibodies against the extracellular domain (ligand binding domain) of CD120a can themselves trigger the cytocidal effect (see EP 412486) which correlates with the effectiveness of receptor cross-linking by the antibodies, believed to be the first step in the generation of the intracellular signaling process. Further, mutational studies (Brakebusch et al., 1992; Tartaglia et al, 1993) have shown that the biological function of CD120a depends on the integrity of its intracellular domain, and accordingly it has been suggested that the initiation of intracellular signaling leading to the cytocidal effect of TNF occurs as a consequence of the association of two or more intracellular domains of CD120a. Moreover, TNF (alpha and beta) occurs as a homotrimer, and as such, has been suggested to induce intracellular signaling via CD120a by way of its ability to bind to and to cross-link the receptor molecules, i.e., cause receptor aggregation.

Another member of the TNF/NGF superfamily of receptors is the FAS/APO1 receptor (CD95), which has also been called the FAS antigen, a cell-surface protein expressed in various tissues and sharing homology with a number of cell-surface receptors including TNF-R and NGF-R. CD95 mediates cell death in the form of apoptosis (Itoh et al., 1991), and appears to serve as a negative selector of autoreactive T cells, i.e., during maturation of T cells, CD95 mediates the apoptotic death of T cells recognizing self-antigens. It has also been found that mutations in the CD95 gene (1pr) cause a lymphoproliferation disorder in mice that resembles the human autoimmune disease systemic lupus erythematosus (SLE) (Watanabe-Fukunaga et al., 1992). The ligand for CD95 appears to be a cell-surface associated molecule carried by, amongst others, killer T cells (or cytotoxic T lymphocytes-CTLs), and hence when such CTLs contact cells carrying CD95, they are capable of inducing apoptotic cell death of the CD95-carrying cells. Further, a monoclonal antibody has been prepared that is specific for CD95, this monoclonal antibody being capable of inducing apoptotic cell death in cells carrying CD95 including mouse cells transformed by cDNA encoding human CD95 (Itoh et al., 1991).

While some of the cytotoxic effects of lymphocytes are mediated by interaction of a lymphocyte-produced ligand with the widely occurring cell surface receptor CD95, which has the ability to trigger cell death, it has also been found that various other normal cells, besides T lymphocytes, express CD95 on their surface and can be killed by the triggering of this receptor. Uncontrolled induction of such a killing process is suspected to contribute to tissue damage in certain diseases, for example, the destruction of liver cells in acute hepatitis. Accordingly finding ways to restrain the cytotoxic activity of CD95 may have therapeutic potential.

Conversely, since it has also been found that certain malignant cells and HIV-infected cells carry CD95 on their surface, antibodies against CD95, or the CD95 ligand, may be used to trigger the CD95 mediated cytotoxic effects in these cells and thereby provide a means for combating such malignant cells or HIV-infected cells (see Itoh et al., 1991). Finding yet other ways for enhancing the cytotoxic activity of CD95 may therefore also have therapeutic potential.

It has been a long felt need to provide a way for modulating the cellular response to TNF (alpha or beta) and CD95 ligand. For example, in the pathological situations mentioned above, where TNF or CD95 ligand is overexpressed, it is desirable to inhibit the TNF- or CD95 ligand-induced cytocidal effects, while in other situations, e.g., wound healing applications, it is desirable to enhance the TNF effect, or in the case of CD95, in tumor cells or HIV-infected cells, it is desirable to enhance the CD95 mediated effect.

A number of approaches have been made by the applicants (see, for example, European Application Nos. EP 186833. EP 308378, EP 398327 and EP 412486) to regulate the deleterious effects of TNF by inhibiting the binding of TNF to its receptors using anti-TNF antibodies or by using soluble TNF receptors (being essentially the soluble extracellular domains of the receptors) to compete with the binding of TNF to the cell surface-bound TNF-Rs. Further, on the basis that TNF-binding to its receptors is required for the TNF-induced cellular effects, approaches by applicants (sec for example EP 568,925) have been made to modulate the TNF effect by modulating the activity of the TNF-Rs.

For example, EP 568925 relates to a method of modulating signal transduction and/or cleavage in TNF-Rs whereby peptides or other molecules may interact either with the receptor itself or with effector proteins interacting with the receptor, thus modulating the normal function of the TNF-Rs. In EP 568925, there is described the construction and characterization of various mutant forms of CD120a, having mutations in its extracellular, transmembrane, and intracellular domains. In this way, regions within the above domains of CD120a were identified as being essential to the functioning of the receptor, i.e., the binding of the ligand (TNF) and the subsequent signal transduction and intracellular signaling which ultimately results in the observed TNF-effect on the cells. Further, there is also described a number of approaches to isolate and identify proteins, peptides or other factors which are capable of binding to the various regions in the above domains of CD120a, which proteins, peptides and other factors may be involved in regulating or modulating the activity of TNF-Rs. A number of approaches for isolating and cloning the DNA sequences encoding such proteins and peptides; for constructing expression vectors for the production of these proteins and peptides; and for the preparation of antibodies or fragments thereof which interact with CD120a or with the above proteins and peptides that bind various regions of CD120a are also set forth in EPO 368925. However, EP 568925 does not specify the actual proteins and peptides which bind to the intracellular domains of the TNF-Rs (e.g., CD95), nor does it describe the yeast two-hybrid approach to isolate and identify such proteins or peptides which bind to the intracellular domains of TNF-Rs. Similarly, in EP 568925 there is no disclosure of proteins or peptides capable of binding the intracellular domain of CD95.

Thus, when it is desired to inhibit the effect of TNF, or of the CD95 ligand, it would be desirable to decrease the amount or the activity of TNF-Rs or CD95 at the cell surface, while an increase in the amount or the activity of TNF-Rs or CD95 would be desired when an enhanced TNF or CD95 ligand effect is sought. To this end the promoters of both the CD120a and the CD120b have been sequenced, analyzed and a number of key sequence motifs have been found that are specific to various transcription regulating factors, and as such the expression of these TNF-Rs can be controlled at their promoter level, i.e., inhibition of transcription from the promoters for a decrease in the number of receptors, and an enhancement of transcription from the promoters for an increase in the number of receptors (EP 606869 and WO 9531206).

While it is known that the tumor necrosis factor (TNF) receptors, and the structurally-related receptor CD95, trigger in cells, upon stimulation by leukocyte-produced ligands, destructive activities that lead to their own demise, the mechanisms of this triggering are still little understood. Mutational studies indicate that in CD95 and CD120a signaling for cytotoxicity involve distinct regions within their intracellular domains (Brakebusch et al., 1992; Tartaglia et al., 1993., Itoh and Nagata, 1993). These regions (the 'death domains') have sequence similarity. The 'death domains' of both CD95 and CD120a tend to self-associate. Their self-association apparently promotes the receptor aggregation which is necessary for initiation of signaling (see Song et al., 1994; Wallach et al., 1994; Boldin et al., 1995), and at high levels of receptor expression can result in triggering of ligand-independent signaling (Boldin et al., 1995).

Some of the cytotoxic effects of lymphocytes are mediated by interaction of a lymphocyte-produced ligand with CD95, a widely occurring cell surface receptor which has the ability to trigger cell death (see also Nagata and Goldstein, 1995); and that cell killing by mononuclear phagocytes involves a ligand-receptor couple, TNF and its receptor CD120a that is structurally related to CD95 and its ligand (see also Vandenabeele et al,. 1995). Like other receptor-induced effects, cell death induction by the TNF receptors and CD95 occurs via a series of protein-protein interactions, leading from ligand-receptor binding to the eventual activation of enzymatic effector functions, which in the case studies have elucidated non-enzymatic protein-protein interactions that initiate signaling for cell death: binding of trimeric TNF or the CD95 ligand molecules to the receptors, the resulting interactions of their intracellular domains (Brakebusch et al., 1992; Tartaglia et al., 1993; Itoh and Nagata, 1993) augmented by a propensity of the death-domain motifs to self-associate (Boldin et al., 1995a), and induced binding of two cytoplasmic proteins (which can also bind to each other) to the receptors' intracellular domains—MORT-1 (or FADD) to CD95 (Boldin et al., 1995b; Chinnaiyan et al., 1995; Kischkel et al., 1995) and TRADD to CD120a (Hsu et al., 1995; Hsu et al., 1996). Three proteins that bind to the intracellular domain of CD95 and CD120a at the 'death domain' region involved in cell-death induction by the receptors through hetero-association of homologous regions and that independently are also capable of triggering cell death were identified by the yeast two-hybrid screening procedure. One of these is the protein, MORT-1 (Boldin et al. 1995b), also known as FADD (Chinnaiyan et al., 1995) that binds specifically to CD95. The second one, TRADD (see also Hsu et al., 1995, 1996). binds to CD120a, and the third, RIP (see also Stanger et al., 1995), binds to both CD95 and CD120a. Besides their binding to CD95 and CD 120a, these proteins are also capable of binding to each other, which provides for a functional "cross-talk" between CD95 and CD120a. These bindings occur through a conserved sequence motif, the 'death domain module' common to the receptors and their associated proteins. Furthermore, although in the yeast two-hybrid test MORT-1 was shown to bind spontaneously to CD95, in mammalian cells, this binding takes place only after stimulation of the receptor, suggesting that MORT-1 participates in the initiating events of CD95 signaling. MORT-1 does not contain any sequence motif characteristic of enzymatic activity, and therefore, its ability to trigger cell death seems not to involve an intrinsic activity of MORT-1 itself, but rather, activation of some other protein(s) that bind MORT-1 and act further downstream in the signaling cascade. Cellular expression of MORT-1 mutants lacking the N-terminal part of the molecule have been shown to block cytotoxicity induction by CD95 or CD120a (Hsu et al., 1996; Chinnaiyan et al., 1996), indicating that this N-terminal region transmits the signaling for the cytocidal effect of both receptors through protein-protein interactions.

Recent studies have implicated a group of cytoplasmic thiol proteases which are structurally related to the *Caenorhabditis elegans* protease CED3 and to the mammalian interleukin-1 beta converting enzyme (ICE) in the onset of various physiological cell death processes (reviewed in Kumar, 1995 and Henkart, 1996). There have also been some indications that protease(s) of this family may take part in the cell-cytotoxicity induced by CD95 and TNF-Rs. Specific peptide inhibitors of the proteases and two virus-encoded proteins that block their function, the cowpox protein crmA and the Baculovirus p35 protein, were found to provide protection to cells against this cell-cytotoxicity (Enari et al., 1995; Los et al., 1995; Tewari et al., 1995; Xue et al., 1995; Beidler et al., 1995). Rapid cleavage of certain specific cellular proteins, apparently mediated by protease(s) of the CED3/ICE family, could be demonstrated in cells shortly after stimulation of CD95 or TNF-Rs.

One such protease and various isoforms thereof (including inhibitory ones), is known as MACH (now caspase-8) which is a MORT-1 binding protein and which serves to modulate the activity of MORT-1 and hence, of CD95 and CD120a, and which may also act independently of MORT-1, has been recently isolated, cloned, characterized, and its possible uses also described, as is set forth in detail and incorporated herein in their entirety by reference, in co-owned, copending Israel Patent Application Nos. IL 114615, 114986, 115319, 116588 and 117932, as well as their corresponding PCT counterpart No. PCT/US96/10521, and in a recent publication of the present inventors (Boldin et al., 1996). Another such protease and various isoforms thereof (including inhibitory ones), designated Mch4 (also called caspase-10) has also recently been isolated and characterized by the present inventors (unpublished) and others (Fernandes-Alnemri et al., 1996; Srinivasula et al., 1996). Caspase-10 is also a MORT-1 binding protein which serves to modulate the activity of MORT-1 and hence likely also of CD95 and CD120a, and which may also act independently of MORT-1. Thus, details concerning all aspects, features, characteristics and uses of caspase-10 are set forth in the above noted publications, all of which are incorporated herein in their entirety by reference.

It should also be noted that the caspases, caspase-8 and caspase-10, which have similar prodomains (see Boldin et al., 1996; Muzio et al., 1996; Fernandes-Alnemri et al., 1996; Vincent and Dixit, 1997) interact through their prodomains with MORT-1, this interaction being via the 'death domain motif' or 'death effector domain', DED, present in the N-terminal part of MORT-1 and present in duplicate in caspase-8 and caspase-10 (see Boldin et al., 1995b; Chinnalyan et al., 1995).

Such proteases, now known as caspases (cysteine aspartate-specific proteinases), are a growing family of cysteine proteases that share several common features. Most of the caspases have been found to participate in the initiation and execution of programmed cell death or apoptosis, while the others appear to be involved in the production of proinflammatory cytokines (Nicholson D W et al. 1997, Salvesen G S et al.1997, Cohen G M 1997). They are synthesized as catalytically inactive precursors and are generally activated by cleavage after specific internal aspartate residues present in interdomain linkers. The cleavage sites of caspases are defined by tetrapeptide sequences (X-X-X-D) and cleavage always occurs downstream of the aspartic acid. As a result certain mature active caspases can process and activate their own as well as other inactive precursors (Femandes-Alnemri T et al. 1996, Srinivasula S M et al. 1996).

Activation of the programmed cell death process is generally specific and involves sequential processing of downstream caspases named "execution" caspases by upstream caspases named "initiator" caspases. The functional characteristics of the two classes of caspases are also reflected by their structure. In fact the "initiator caspases" contain longer prodomain regions as compared to the "executioner" caspases (Salvesen G S et al. 1997, Cohen G M 1997). The long prodomain allows the initiator or "'apical" caspases to be activated by triggering of the death receptors of the TNF receptor family. Upon ligand-induced trimerization of the death receptors, the initiator caspases are recruited through their long N-terminal prodomain to interact with specific adapter molecules to form the death inducing signaling complex (Cohen G M 1997, Kischkel F C et al., 1995). For example, caspase-8/MACH and probably caspase-10, which contain two Death Effector Domains (DED) or FADD domains, are recruited to the receptor complex by the adapter molecules FADD/MORT-1, whereas caspase-2 is recruited by CRADD/RAIDD and RIP (Nagata S et al. 1997, MacFarlane M et al. 1997, Ahmad M et al. 1997, Duan H et al. 1997). Due to the trimeric nature of the activated receptor complex at least two caspase molecules are thought to be brought in close proximity to each other thus leading to their activation by autocatalytic processing (Yang et al. 1998, Muzio et al. 1998).

Caspases are synthesized as proenzymes consisting of three major subunits, the N-terminal prodomain, and two subunits, which are sometimes separated by a linker peptide. The two subunits have been termed "long" or subunit 1 containing the active enzymatic site, and "short" or subunit 2. For full activation of the enzyme, the prodomain and the two subdomains are cleaved. The two cleaved subunits form a heterodimer, whereby the long domain is derived from the N-terminus, and the short subunit is derived from the C-terminal region of the caspase precursor. Based on the deduced three dimensional structure of caspase-3, it appears that the C-terminal end of the long domain as well as the N-terminus of the short subdomain have to be freed and the C-terminus of the short subunit has to be brought into close proximity with the N-terminus of the long subunit in order to yield a correctly folded and active enzyme (Rotonda et al 1996, Mittl et al. 1997, Srinivasula et al. 1998).

N-acetylglucosamine-6-phosphate deacetylase is an intracellular enzyme known to be involved in the intracellular metabolism of glucosamine. A genomic DNA fragment containing N-acetylglucosamine-6-phosphate deacetylase was cloned from the chitinase-producing bacterium *Vibrio cholerae* (Yamano et al., Biosci Biotechnol Biochem. 61, p. 1349–53, 1997).

The nagA gene encoding *E. coli* N-acetylglucosamine-6-phosphate deacetylase is also known [see, e.g., Peri et al., January 1990, 68(1), pp. 123–137]. Human N-acetylglucosamine-6-phosphate deacetylase has so far not yet been reported as cloned and sequenced.

SUMMARY OF THE INVENTION

The invention provides a caspase-8 interacting protein, or an isoform, allelic variant, fragment, functional analog, mutant or derivative thereof, which is capable of interacting with subunit 1 and/or subunit 2 of caspase-8.

The invention further provides human N-acetylglucosamine-6-phosphate deacetylase, or an isoform, allelic variant, fragment, functional analog, mutant or derivative thereof.

Still further, the invention provides a protein which comprises the amino acid sequence of FIGS. 2, 3, 5B or 6.

The invention also provides a protein which comprises the amino acid sequence of the Tip-60 protein excluding amino acids 94 to 145.

Further encompassed in the scope of the invention is a protein which comprises the amino acid sequence encoded by the clones P27, P70, P79, L7, L12, M26, B4, B17, J40, B13, B37, B33 or P74, and its splice variants P16 and P43, as described hereinbelow.

The invention also provides a protein as defined above, which is cleaved in vitro or in vivo by caspase-8.

The invention also provides an isolated DNA sequence coding for a protein of the invention. Comprised within that scope is the DNA sequence of FIG. 2 and FIG. 3. Also comprised within the scope of the invention is an isolated DNA capable of hybridizing to said DNA sequence under moderately stringent conditions.

The invention also provides a vector comprising a DNA sequence as defined above.

The invention further provides an eukaryotic or prokaryotic host cell containing a vector of the invention.

The invention further provides a method of producing a protein, isoform, allelic variant, fragment, functional analog, mutant or derivative of a caspase-8 interacting protein of the invention, comprising growing a host cell of the invention under conditions that allow production of said protein, affecting post-translational modifications as necessary for obtaining said protein, isoform, allelic variant, fragment, functional analog, or mutant, or derivative, and isolating said protein, isoform, allelic variant, fragment, functional analog, or mutant, or derivative.

The invention also provides said method wherein the cell is a prokaryotic cell.

The invention further provides said method wherein the cell is an eukaryotic cell.

The invention also provides said method wherein the cell is a mammalian, insect, or yeast cell.

The invention also provides said method wherein the cell is a HeLa or 293 T HEK cell.

The invention further provides said method wherein as a promoter, the human CMV promoter is employed.

Still further, the invention provides a caspase-8 interacting peptide comprising at least 4 consecutive amino acids of a protein of the invention.

A derivative of said peptide is encompassed within the scope of the invention. Further encompassed within the scope of the invention is said peptide derivative, capable of forming a covalent bond with caspase-8 upon contacting said caspase-8.

The invention also provides a ribozyme specific for a nucleotide sequence corresponding to a DNA sequence of the invention.

The invention further provides an antisense oligonucleotide comprising at least 9 nucleotides of a sequence corresponding to a DNA sequence of the invention.

The invention also provides an antibody directed at an epitope of a protein of the invention.

The invention also provides an immunoassay for the detection of a caspase-8 interacting protein, comprising the antibody of the invention.

The invention further provides an immunoassay for the detection of caspase-8, comprising a peptide of the invention.

The invention also provides an immunoassay for the detection of caspase-8, comprising a protein of the invention.

The invention further provides a method of identifying caspase-8 interacting proteins, comprising the steps of
   a) providing a yeast cell having a reporter gene linked to a promoter comprising a DNA sequence motif;
   a) expressing in said yeast cell a p20 subunit of said caspase-8;
   b) expressing in said yeast cell a fusion protein of a DNA binding domain and the p10 and/or p20 subunit of said caspase-8, wherein said DNA binding domain is capable of binding to said DNA sequence motif;
   c) optionally, expressing in said yeast cell an unfused p10 or p20 subunit of said caspase-8;
   d) transforming a culture of said yeast cell with a library consisting of an expression vector driving expression of a fusion protein consisting of a cDNA library and a transcriptional activator;
   e) screening the culture of transformed yeast cells for yeast cells wherein the reporter gene is activated, and
   f) isolating a yeast cell from step e) and further isolating the caspase-8 interacting protein, which is expressed in its prey vector.

The invention also provides said caspase-8 interacting protein, isoform, allelic variant, fragment, functional analog, mutant, or derivative, said ribozyme, antisense oligonucleotide or antibody, for use in modulating caspase-8 activity.

The invention further provides said caspase-8 interacting protein, isoform, allelic variant, fragment, functional analog, mutant, or derivative, said ribozyme, antisense oligonucleotide or antibody, for use in modulating TNF-receptor or Fas-mediated effects.

Still further, the invention provides said caspase-8 interacting protein, isoform, allelic variant, fragment, functional analog, mutant, or derivative, said ribozyme, antisense oligonucleotide or antibody, for use in modulating apoptosis.

The invention also provides said caspase-8 interacting protein, isoform, allelic variant, fragment, functional analog, mutant, or derivative, said ribozyme, antisense oligonucleotide or antibody, for use as a medicament.

The invention further provides said caspase-8 interacting protein, isoform, allelic variant, fragment, functional analog, mutant, or derivative, said ribozyme, antisense oligonucleotide or antibody, for use as a medicament in the treatment of multiple sclerosis with primary oligodendrogliopathy, autoimmune uveoretinitis, diabetes, lupus, autoimmune myocarditis I, HCV mediated chronic hepatitis, chronic gastritis e.g., type A gastritis, mixed connective tissue disease, (MCTD), Crohn's disease, or ulcerative colitis.

The invention also provides a triplex-forming oligonucleotide capable of binding to a purine-rich sequence in the promoter region of a caspase-8 interacting gene. The triplex-forming oligonucleotide may contain chemical modifications, such as internucleoside phosphate linkages modified with the cation N,N-diethyl-ethylenediamine, Uridine, benzo[g]-quinazoline-2,4-dione-(1H,3H)-dione or benzo[f]quinazoline-2,4-dione-(1H,3H)-dione residues in place of Thymidine residues. The triplex-forming oligonucleotide may further be covalently linked to chemicals having affinity for DNA, preferably such agents as may intercalate into DNA, such as acridine and psoralene.

The term "interacting" in the context of this description, relating to interaction of a protein of the invention with caspase-8, is meant to include direct forms of interaction, such as binding, cleavage, and indirect interaction, e.g. through adapter proteins. The interaction may optionally result in modulation of the caspase-8 mediated signal.

The term "binding" in the context of this application, when referring to binding of caspase-8 interaction proteins, is meant to relate to physical association of the caspase-8 interacting protein with caspase-8. This physical association may be measured in immunoassays, such as ELISA or RIA assays, in the two-hybrid test, in immunoprecipitation assays, or in size separation-based assays, such as non-denaturing acrylamide gel electrophoresis or size exclusion gel chromatography of a mixture of caspase-8, or a subunit thereof, and a protein of the invention. When using the two-hybrid test, it is understood that the caspase-8 or subunit thereof is expressed as a DNA activation domain fusion, and the caspase-8 interacting protein is expressed as a DNA binding domain fusion, or vice versa.

The term "two-hybrid test" relates to the two-hybrid assay wherein protein-protein interactions can be measured by introducing into yeast cells a first expression vector coding for a fusion of a first protein and a DNA binding domain, and a second expression vector coding for a fusion of a second protein with a DNA activation domain. The yeast cells must contain at least one reporter gene driven by a promoter that contains a DNA sequence motif which is recognized by said DNA binding domain. Usually, two reporter genes, e.g., Histidine synthetase and beta-Galactosidase, are used. This enables the researcher to avoid false-positives that may result from mutation. This technique has been modified and refined by the present applicants for use in screening, isolating, and testing proteins that mediate TNF-R and Fas signals, see e.g., WO 97/03998 and references therein. The two-hybrid test relies on localization of both fusion proteins to the cell nucleus.

The term "two hybrid test" as used herein further comprises a modification of the two-hybrid technique wherein cell growth signaling proteins, such as ras and sos are used (Broder et al., Curr Biol 1998, 8, p. 1121–4, Aronheim et al., Nucleic Acids Res 1997 25, p. 3373–4, and references therein). In order to be functional, these proteins require relocalization to the cell membrane. This is achieved by expressing a cell growth signaling protein as a fusion with a first protein, and expressing a cell membrane localization signal, such as a myristilation signal sequence, as a fusion with a second protein. An interaction between the first and second proteins will re-localize the cell growth signaling protein to the cell membrane and thus trigger cell growth. Aggressively growing cells are then selected for further study. This system is different from the above-described two-hybrid system, because it does not rely on localization of both hybrids to the cell nucleus.

The term "bait" refers to the protein in the above-mentioned two-hybrid test, which is expressed as a fusion protein with a DNA binding domain.

The term "prey" refers to the protein in the above-mentioned two-hybrid test that is expressed as s fusion with a DNA activating domain.

BRIEF DESCRIPTION OF THE FIGURES

FIG. 2 is a preliminary partial nucleotide (SEQ ID NO:1) and deduced amino acid sequence (SEQ ID NO:2) of clone 32 encoding a caspase-8 interacting protein as obtained from a cDNA clone.

FIG. 3 shows the putative full length sequence of the human nucleotide (SEQ ID NO:3) and deduced amino acid sequence (SEQ ID NO:4) N-acetylglucosamine-6-phosphate deacetylase composed of the 5' extension of clone J2, the EST clone AA460869 and exon trap clone L48741.

FIG. 4A shows the functional activity of clone J2 expressed as the percentage of apoptotic cells, following transfection of HEK-293T cells either with the p55 TNF receptor alone (marked p55 TNFR) or with the p55TNF receptor together with p35, a baculovirus inhibitor of caspases (p55+p35) or with clone J2 (p55+J2), or with the p55 TNF receptor together with a non cleavable mutant of J2 (denoted J*) containing an Asp to Glu substitution at position 346 of FIG. 3 (p55+J2*). This mutant can be cleaved neither in vitro nor in vivo.

FIG. 4B shows the percentage of apoptotic HeLa cells alone, or following transfection with p35 or J2 or J2* treated with TNF and cycloheximide.

FIG. 5A shows the 1725 coding base pairs at the 5' end of clone P74 (SEQ ID NO:5).

FIG. 5B shows the 574 amino acid sequence deduced from the sequence of clone P74 of FIG. 5A (SEQ ID NO:6).

FIG. 6 shows 1428 amino acids (SEQ ID NO:7) of an open reading frame derived from a deduced amino acid sequence of PAC clone accession number RPCI5-1057I20.

FIG. 7 shows the alignment of the 574 amino acids of the open reading frame derived from the deduced amino acid sequence of clone p74 (denoted cloned) compared to the 1428 amino acids of the open reading frame derived from the deduced amino acid sequence of PAC clone RPCI5-1057I20 (denoted deduced).

FIG. 8 shows the alignment of the open reading frame of the deduced amino acid sequence of PAC clone RPCI5-1057I20 (top sequence) (SEQ ID NO:8) with the sequence of histone deacetylase A (lower sequence, GENBANK accession number NP-006028.1) (SEQ ID NO:9).

FIG. 9A shows an autoradiography of the Bid protein and the proteins encoded by the cDNA clones J2, or P16, or P43, or P70, or P74, or P79, produced in a reticulocyte lysate in the presence of $^{35}$S Methionine, separated on an SDS PAGE gel.

FIG. 9B shows an autoradiography of the Bid protein and the proteins encoded by the cDNA clones J2, or P16, or P43, or P70, or P74, or P79 produced as in FIG. 9A analyzed for binding to caspase-8 expressed in bacteria as a fusion protein of its two subunits, fused to GST. The position of the molecular weight markers is shown on the left of the gel.

DETAILED DESCRIPTION OF THE INVENTION

Figure 1:
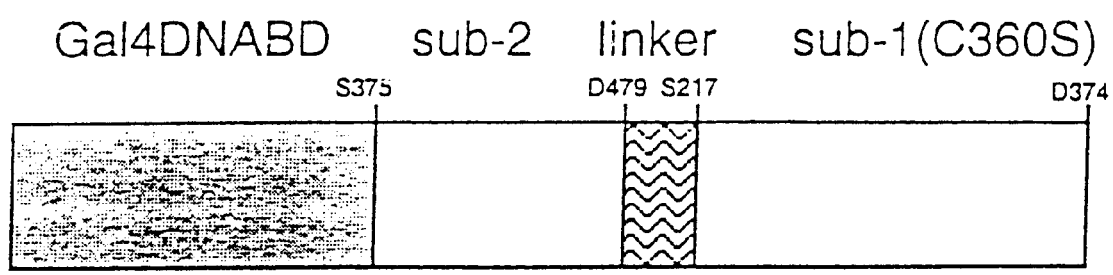
FIG. 1 shows the schematic representation of the single chain construct of caspase-8, used as bait in the two-hybrid screen described in Example 1B.

A number of methods of the art of molecular biology are not detailed herein, as they are well known to the person of skill in the art. Such methods include site-directed mutagenesis, PCR cloning, phage library screening using oligonucleotide or cDNA probes, expression of cDNAs, analysis of the recombinant proteins, transformation of bacterial and yeast cells, transfection of mammalian cells, and the like. Textbooks describing such methods are e.g., Sambrook et al., Molecular Cloning A Laboratory Manual, Cold Spring Harbor Laboratory; ISBN: 0879693096, 1989, Current Protocols in Molecular Biology ,by F. M. Ausubel, ISBN: 047150338X, 1988, and Short Protocols in Molecular Biology, by F. M. Ausubel et al. (eds.) 3rd ed. John Wiley & Sons; ISBN: 0471137812, 1995. These publications are incorporated herein in their entirety by reference.

In order to identify caspase-8 interacting proteins and potential substrates, by two hybrid screening method, the two hybrid or three-hybrid system may be used.

The two-hybrid system is used in the method of the invention essentially as described by Fields and Song (Nature 340, p. 245, 1989). Preferably, individual vectors, yeast strains, and libraries may be obtained from Clontech (Palo Alto, USA), as components of the MATCHMAKER two-hybrid system (#PT1265-1).

The preferred embodiment of the yeast two-hybrid system as used in the method of the invention has been described by Boldin et al., Cell. 85, p. 803–15, 1996. The yeast two-hybrid system has further been described in U.S. Pat. No. 5,580,736, Brent et al. These publications are therefore incorporated herein in their entirety by reference.

The three-hybrid system is used essentially as described by Tirode et al., J. Biol. Chem. 272, p. 22995–9, 1997. For detecting caspase-8 interacting proteins according to the invention, it is required that the two subunits of caspase-8 be expressed independently. For that purpose, the two caspase-8 subunits are preferably expressed separately under the control of different promoters. In a preferred embodiment, the caspase-8 p10 subunit (Serine 375 to Aspartic acid 479) is expressed under control of a weak promoter operable in yeast, in-frame with a DNA binding domain. Preferably, the weak promoter is the yeast ADH promoter and the DNA binding protein is the DNA binding domain of the yeast transcriptional activator Gal-4 or of the bacterial LexA protein. The ADH promoter and the Gal4 DNA binding domain are present e.g., in the pGBD commercially available by Clontech, Palo alto, USA. However, it will be apparent to a person skilled in the art that other promoters may be used, so long as the promoter is effective in yeast cells. By the same token, other DNA binding domains may be used, as long as these DNA binding domains do not have transcriptional activator function.

The long, active, caspase-8 p20 subunit (Serine 217 to Aspartic acid 374) is expressed as unfused protein under control of an inducible promoter operable in yeast cells. Preferably, the Met25 methionine repressible promoter as described in the above Tirode et al. may be used. The use of an inducible promoter simplifies the detection of the p10–p20 complex by immunoprecipitation and polyacrylamide gel electrophoresis. The inducible promoter has further advantages in that it enables the expression in yeast of protein that may be toxic to the yeast cells, because of the possibility to limit the period wherein the potentially toxic protein is expressed.

The proteins to be screened with the method of the invention are preferably provided in the form of a cDNA library. However, also genomic libraries or combinatorial libraries may be used. The library is cloned at the C-terminal end of a transcriptional activation domain operable in yeast. Preferably, the transcriptional activation domain of the yeast Gal-4 protein is used, however, a large number of other transcriptional activators may be used. Preferably, the pGAD GH vector available from Clontech is used for cloning of the library.

The yeast strain used for screening must contain a selection marker such as histidine synthetase, under the control of a promoter that comprises a DNA sequence to which the above-mentioned DNA binding domain binds specifically. Preferably, the yeast cell also contains a reporter gene under the control of a promoter that comprises a DNA sequence to which the above-mentioned DNA binding domain binds specifically. The yeast strain HF7c, available from Clontech, may be used for screening with Gal-4 binding domain hybrids; the strain L40 may be used when lexA is the DNA binding domain used.

After transformation, the yeast cells are placed in conditions selective for active plated onto media lacking certain amino acids, as required for the stability of the plasmids introduced thereinto.

The medium is selective for yeast cells in which the gene for the above-mentioned selection marker is activated. Preferably, the selection marker is the histidine synthetase gene. Yeast cells expressing this gene may be selected for by culturing in medium lacking histidine. Am advantage of this system is the possibility of adding the histidine synthetase inhibitor 3-aminotriazole to the growth medium. It is thus possible to inhibit growth of yeast cells in which a small amount of histidine synthetase is expressed, caused by leaking of the promoter containing the sequence to which the above-mentioned DNA binding domain specifically binds. In some clones, a weak, non-specific interaction between the caspase-8 p10 and/or p20 subunit and the said clone may cause spurious activation of said promoter. Thus, by raising the concentration of said inhibitor in the medium used for selection of interacting clones, it is possible to select only clones that interact with a certain minimal strength. The concentration of 3-aminotriazole is preferably 7.5 mM.

Clones identified by their ability to grow in medium lacking histidine are further analyzed by quantification of their reporter gene activity. Preferably, the lacZ gene is used a reporter gene. Quantification of lacZ activity is done preferably in liquid culture, as described in Boldin et al., J. Biol. Chem. 270, 7795–8, 1995.

The above-described screening method may be carried out similarly using the two-hybrid test. The essential difference is that the two subunits of the caspase-8 are expressed as a single peptide chain, which is a fusion protein with the above-noted DNA binding domain. The p20 subunit is mutated in its active site (cysteine 360-Serine 360) as described below.

Preferably, the p10 subunit is separated from the p20 subunit by a linker, which is preferably between 10 and 50 amino acids in length. Said linker comprises preferably small uncharged amino acids such as glycine, serine, threonine, Alanine and valine. More preferably, the linker is comprised of serine and glycine residues. Most preferably, the ration between glycine residues and serine residues in said linker is about 3:1 to 4:1.

The obtention of clones using the two-hybrid system with the above-described caspase-8 bait is similar to the above-described use of the three-hybrid system, with the exception of the fact that clones binding to only one of the subunits, cannot be readily distinguished from those that bind to both or that require the complex of both subunits for binding. However, any clone found in the two-hybrid method can be readily tested for binding to the two subunits by evaluation of the lacZ activity of double transformants, i.e., yeast cells that are transformed with the newly identified clone and either the p10 or the p20 caspase-8 subunit, wherein said subunit is fused to the DNA binding domain. Binding to the complex of p10 and p20 subunit can also be easily evaluated by determining the lacZ activity of triple transformants wherein one of the subunits of caspase-8 is expressed as a fusion protein with the DNA binding domain, and the other as unfused protein. It is evident that the above-noted three hybrid system is therefore also useful in determining the binding characteristics of clones found with the two-hybrid system, as the inducible promoter used therein enables the quick identification of clones interacting with the p10 subunit only, or with the p10–p20 complex of subunits.

Clones that are able to grow in medium lacking histidine and that express lacZ activity are then selected for further study. Firstly, the proteins encoded by the clones are tested for their ability to bind nonrelevant proteins, such as Lamin. In general, Lamin-binding clones were discarded.

Clones that are found to specifically interact with caspase-8 are then further analyzed. This is done as well with partial clones as obtained directly from the above-described screening methods, as well as with full-length clones that are obtained on the basis of the sequence of said partial clones. In order to obtain full-length clones, the sequence of the partial clone is obtained by extracting the DNA of said clone from the yeast cells by methods known to the person of skill in the art. The DNA is then transformed into bacteria in order to obtain large amounts of purified DNA, which may be used for sequencing. Alternatively, the insert in the vector, which is preferably the above-noted pGBD vector, may be excised using restriction enzymes and cloned into another vector, such as pBluescript available from Stratagene, for the purpose of sequencing. Sequencing is done y the chain-termination method, preferably using Sequenase2 enzyme as available in the sequencing kit of United States Biochemicals.

The so-obtained sequence may then be entered into a database search program and overlapping sequences are identified by computer search. The programs used are well known to all of skill in the art and comprise e.g., the GCG (genetics computer group) package. Preferably, a search utility such as Basic Local Alignment Search Tool (BLAST) is used. The Blastn command may be used for searching for nucleotide sequences that are overlapping or similar with the clone identified.

The protein identified by the method of the invention is provided as a fusion protein with a DNA binding domain. Therefore, the frame in which the nucleic acid sequence should be translated, is known, as it must be in-frame with the coding sequence of the DNA binding domain. The DNA sequence of the clone identified by the invention can therefore be unambiguously translated into amino acid sequence.

The Blastp program, available on the above-noted EMBL server, may then be used for identification of overlapping protein sequences or similar proteins.

Alternatively, or in addition to the above-noted methods of searching databases, a library, such as a genomic library or a cDNA library, may be screened in order to identify complete clones. Such screening methods are described in the above-noted Sambrook et al and Ausubel et al. Alternatively, or in addition, PCR-based cloning techniques may be used, such as rapid amplification of cDNA ends (5' and 3' RACE, Graham et al., Biochem Biophys Res Commun 177, p. 8–16, 1991, and references therein).

The partial clones identified in the screening assay of the invention, or the full-length clones obtained by any of the above methods, are then further investigated. This is done e.g., by testing the sensitivity of these clones to proteolytic digestion with active caspase-8. This assay may be carried out in vivo. To this end, a mammalian cell line is transfected with an expression vector that produces the protein encoded by the clone to be tested, and an expression vector encoding a second protein whose expression will induce caspase-8 activity. The expression vectors preferably comprise a strong promoter for expression of the clone and of the second protein, such as the Rous sarcoma virus (RSV, Yamamoto et al. Cell 22, p. 787–97, 1980), myeloproliferative sarcoma virus (MPSV, Artelt P et al., Gene 68 p. 213–9, 1988), Cytomegalovirus (CMV, Thomsen, et al. PNAS 81 p. 659–63, 1984), or similar promoters of viral or cellular origin.

The second protein whose expression induces caspase-8 activity is selected from Fas-intracellular domain, CD120a intracellular domain, Mort-1, caspase-8, or an equivalent protein capable of inducing caspase-8 activity. Alternatively, caspase-8 activity may be induced in the cells by treatment with TNF or CD95-ligand. Experiments detailing the possible mechanism and the further technical details of this type of assay are found in the above-noted Boldin et al., Cell 1996.

After introducing the above-noted expression vector coding for the second protein and the protein to be tested into the mammalian cell, the cell culture is cultured for a period of time sufficient to allow expression of the proteins, activation or expression of caspase-8, and cleavage of the protein to be tested to occur. The said time period is usually 4 to 72 hours, preferably 16 to 30 hours, most preferably 20 to 24 hours. In order to determine the extent of cleavage, a whole cell lysate is prepared. Alternatively, the tagged protein may be purified using anti-tag antibodies, or nickel-nitrilotriacetic acid chromatography, reagents and detailed protocols for which are available from Qiagen GmbH, Hilden, Germany. The technique of immunoprecipitation is described in the above Boldin et al. Cell, 1996.

Reagents and instructions for immunoprecipitation are further available from Boehringer Mannheim, Mannheim, Germany, in kit form.

The whole cell lysate of purified protein is now size-resolved by SDS polyacrylamide gel electrophoresis.

The protein to be tested or its tagged fragments may now be visualized by the western blot technique using anti-tag antibodies. A preferred tag is the histidine tag, in combination with an anti-polyhistidine antibody. However, other combinations of tag sequence and antibody specific thereto may be used, so long as the antibody remains specific for the tag sequence, i.e., does note recognize other proteins in the whole cell lysate. The specificity of the cleavage may be verified by running control reactions wherein a specific caspase inhibitor is added to the mammalian cell culture in the above-mentioned time period. A preferred inhibitor is an inhibitor selected from zVAD-fmk, zDEVD-fmk, zIETD-fmk (see Keppler-Hafkemeyer et al., Biochemistry 37, p. 16934–42, 1998). A more preferred inhibitor is zVAD-fmk. Other inhibitors that may be used are proteins such as Bclx or the p35 protein that act as cellular inhibitor of caspases. Inhibition of cleavage when such proteins are coexpressed in the assay indicates that the cleavage is specific for caspases.

A second assay for testing whether the protein to be tested is cleavable by caspase-8 is an in-vitro assay, whereby recombinantly produced caspase-8 is used in an enzymatic reaction together with labeled protein to the tested. The protein to be tested may be produced as described above by cloning the coding sequence thereof into an expression vector containing a strong promoter and transfection into a mammalian cell. Advantageously, the protein to be tested is tagged, as described above, so that it can be purified from the mammalian cell extract. by anti-tag antibodies or other agents capable of specifically binding the tag sequence. Alternatively, the protein to be tested may be produced in vitro using an in vitro translation system. The technique of in vitro translation is well known to the person of skill in the art, and reagents and detailed protocols therefor are available e.g., from Stratagene, La Jolla, USA.

Alternatively, the protein to be tested may be labeled, e.g. using a radioisotope. Advantageously, when using isotopic labeling, the protein to be tested is expressed in vitro and the isotopically labeled amino acid, together with unlabeled amino acid, is added during the in vitro translation reaction. Preferably, the isotope is $S^{35}$. Further preferably, the labeled amino acid is $S^{35}$-Methionine and the ration between labeled and unlabeled amino acid is 1:1 to about 1:1000.

The recombinantly produced protein to be tested and the recombinantly produced caspase-8 active enzyme are then combined in a suitable buffer and for a time period sufficient to allow cleavage to occur. The preferred buffer and other preferred parameters of the assay are described in the above Boldin et al., Cell 1996. The preferred time period is generally between 10 min and several hours, preferably between 30 min and one hour.

After allowing cleavage to occur, the reaction is size-separated by SDS polyacrylamide gel electrophoresis. If isotopic labeling has been used, the gel may be dried and the isotope detected by photographic film or by phosphoimaging (Fuji). The protein to be tested is tagged, and may be detected by using tag-specific antibodies in a western blot.

The appearance of additional low molecular weight bands in reactions in which caspase-8 protein was added, compared to control reactions without caspase-8 indicates cleavage of the protein to be tested by caspase-8. The size of the lower molecular weight band indicates in addition the approximate location of the cleavage site.

The present invention relates to a DNA sequence coding for a caspase-8 interacting proteins.

Moreover, the present invention further concerns the DNA sequences encoding a biologically active isoform, allelic variant, fragment, functional analog, mutant or derivative of the caspase-8 interacting protein, and the protein, isoform, allelic variant, fragment, functional analog, mutant or derivative encoded thereby. The preparation of such analogs, fragments, mutants and derivatives is by standard procedure (see for example, Sambrook et al., 1989) in which in the DNA sequences encoding the caspase-8 interacting protein, one or more codons may be deleted, added or substituted by another, to yield analogs having at least one amino acid residue change with respect to the native protein.

Of the above DNA sequences of the invention which encode a caspase-8 interacting protein, isoform, allelic variant, fragment, functional analog, mutant or derivative, there is also included, as an embodiment of the invention, DNA sequences capable of hybridizing with a cDNA sequence derived from the coding region of a native caspase-8 interacting protein, in which such hybridization is performed under moderately stringent conditions, and which hybridizable DNA sequences encode a biologically active caspase-8 interacting protein. These hybridizable DNA sequences therefore include DNA sequences which have a relatively high homology to the native caspase-8 interacting protein cDNA sequence and as such represent caspase-8 interacting protein-like sequences which may be, for example, naturally-derived sequences encoding the various caspase-8 interacting protein isoforms, or naturally-occurring sequences encoding proteins belonging to a group of caspase-8 interacting protein-like sequences encoding a protein having the activity of caspase-8 interacting protein. Further, these sequences may also, for example, include non-naturally occurring, synthetically produced sequences, that are similar to the native caspase-8 interacting protein cDNA sequence but incorporate a number of desired modifications. Such synthetic sequences therefore include all of the possible sequences encoding analogs, fragments and derivatives of caspase-8 interacting protein, all of which have the activity of caspase-8 interacting protein.

As used herein, stringency conditions are a function of the temperature used in the hybridization experiment, the molarity of the monovalent cations and the percentage of formamide in the hybridization solution. To determine the degree of stringency involved with any given set of conditions, one first uses the equation of Meinkoth et al. (1984) for determining the stability of hybrids of 100% identity expressed as melting temperature $T_m$ of the DNA-DNA hybrid $T_m$=81.5° C.+16.6 (LogM)+0.41 (%GC)−0.61 (% form)−500/L where M is the molarity of monovalent cations, %GC is the percentage of G and C nucleotides in the DNA, % form is the percentage of formamide in the hybridization solution, and L is the length of the hybrid in base pairs. For each 1° C. that the $T_m$ is reduced from that calculated for a 100% identity hybrid, the amount of mismatch permitted is increased by about 1%. Thus, if the $T_m$ used for any given hybridization experiment at the specified salt and formamide concentrations is 10° C. below the $T_m$ calculated for a 100% hybrid according to the equation of Meinkoth, hybridization will occur even if there is up to about 10% mismatch.

"Moderately stringent conditions" are those which provide a $T_m$ which is not more than 20° C. below the $T_m$ that would exist for a perfect duplex with the target sequence, either as calculated by the above formula or as actually measured. Without limitation, moderately stringent (15–20° C. below the calculated or measured $T_m$ of the hybrid) conditions use a wash solution of 2×SSC (standard saline citrate) and 0.5% SDS (sodium dodecyl sulfate) at the appropriate temperature below the calculated $T_m$ of the hybrid. The ultimate stringency of the conditions is primarily due to the washing conditions, particularly if the hybridization conditions used are those which allow less stable hybrids to form along with stable hybrids. The wash conditions at higher stringency then remove the less stable hybrids. A common hybridization condition that can be used with moderately stringent wash conditions described above is hybridization in a solution of 6×SSC (or 6×SSPE (standard saline-phosphate-EDTA)), 5×Denhardt's reagent, 0.5% SDS, 100 µg/ml denatures, fragmented salmon sperm DNA at a temperature approximately 20° to 25° C. below the $T_m$. If mixed probes are used, it is preferable to use tetramethyl ammonium chloride (TMAC) instead of SSC (Ausubel, 1987, 1999).

To obtain the various above noted naturally occurring caspase-8 interacting protein-like sequences, standard procedures of screening and isolation of naturally-derived DNA or RNA samples from various tissues may be employed using the natural caspase-8 interacting protein cDNA or portion thereof as probe (see for example standard procedures set forth in Sambrook et al., 1989).

The invention relates to a caspase-8 interacting protein as may be identified by the above screening assay. The invention also relates to a polypeptide or protein substantially corresponding to caspase-8 interacting protein. The term "substantially corresponding" includes not only caspase-8 interacting protein but also polypeptides or proteins that are analogs thereof.

Analogs that substantially correspond to caspase-8 interacting protein are those polypeptides in which one or more amino acid of the caspase-8 interacting protein's amino acid sequence has been replaced with another amino acid, deleted and/or inserted, provided that the resulting protein exhibits substantially the same or higher biological activity as the caspase-8 interacting protein to which it corresponds.

In order to substantially correspond to caspase-8 interacting protein, the changes in the sequence of caspase-8 interacting proteins, such as isoforms are generally relatively minor. Although the number of changes may be more than ten, preferably there are no more than ten changes, more preferably no more than five, and most preferably no more than three such changes. While any technique can be used to find potentially biologically active proteins which substantially correspond to caspase-8 interacting proteins, one such technique is the use of conventional mutagenesis techniques on the DNA encoding the protein, resulting in a few modifications. The proteins expressed by such clones can then be screened for their ability to bind to caspase-8 and to modulate caspase-8 activity in modulation/mediation of the intracellular pathways noted above.

"Conservative" changes are those changes which would not be expected to change the activity of the protein and are usually the first to be screened as these would not be expected to substantially change the size, charge or configuration of the protein and thus would not be expected to change the biological properties thereof. Conservative substitutions of caspase-8 interacting proteins include an analog wherein at least one amino acid residue in the polypeptide has been conservatively replaced by a different amino acid. Such substitutions preferably are made in accordance with the following list as presented in Table IA, which substitutions may be determined by routine experimentation to provide modified structural and functional properties of a synthesized polypeptide molecule while maintaining the biological activity characteristic of caspase-8 interacting protein.

TABLE IA

| Original Residue | Exemplary Substitution |
|---|---|
| Ala | Gly; Ser |
| Arg | Lys |
| Asn | Gln; His |
| Asp | Glu |
| Cys | Ser |
| Gln | Asn |

TABLE IA-continued

| Original Residue | Exemplary Substitution |
|---|---|
| Glu | Asp |
| Gly | Ala; Pro |
| His | Asn; Gln |
| Ile | Leu; Val |
| Leu | Ile; Val |
| Lys | Arg; Gln; Glu |
| Met | Leu; Tyr; Ile |
| Phe | Met; Leu; Tyr |
| Ser | Thr |
| Thr | Ser |
| Trp | Tyr |
| Tyr | Trp; Phe |
| Val | Ile; Leu |

Alternatively, another group of substitutions of caspase-8 interacting protein are those in which at least one amino acid residue in the polypeptide has been removed and a different residue inserted in its place according to the following Table IB. The types of substitutions which may be made in the polypeptide may be based on analysis of the frequencies of amino acid changes between a homologous protein of different species, such as those presented in Table 1-2 of Schulz et al., G. E., Principles of Protein Structure Springer-Verlag, New York, N.Y., 1798, and FIGS. 3–9 of Creighton, T E., Proteins: Structure and Molecular Properties, W. H. Freeman & Co., San Francisco, Calif. 1983. Based on such an analysis, alternative conservative substitutions are defined herein as exchanges within one of the following five groups:

TABLE IB

1. Small aliphatic, nonpolar or slightly polar residues: Ala, Ser, Thr (Pro, Gly);
2. Polar negatively charged residues and their amides: Asp, Asn, Glu, Gln;
3. Polar, positively charged residues:
His, Arg, Lys;
4. Large aliphatic nonpolar residues:
Met, Leu, Ile, Val (Cys); and
5. Large aromatic residues: Phe, Tyr, Trp.

The three amino acid residues in parentheses above have special roles in protein architecture. Gly is the only residue lacking any side chain and thus imparts flexibility to the chain. This however tends to promote the formation of secondary structure other than a-helical. Pro, because of its unusual geometry, tightly constrains the chain and generally tends to promote beta-turn-like structures, although in some cases Cys can be capable of participating in disulfide bond formation which is important in protein folding. Note that Schulz et al., supra, would merge Groups 1 and 2, above. Note also that Tyr, because of its hydrogen bonding potential, has significant kinship with Ser, and Thr, etc.

Conservative amino acid substitutions according to the present invention, e.g., as presented above, are known in the art and would be expected to maintain biological and structural properties of the polypeptide after amino acid substitution. Most deletions and substitutions according to the present invention are those which do not produce radical changes in the characteristics of the protein or polypeptide molecule. "Characteristics" is defined in a non-inclusive manner to define both changes in secondary structure, e.g. a-helix or beta-sheet, as well as changes in biological activity, e.g., binding to caspase-8 and/or mediation of the effect of caspase-8 on cell death.

Examples of production of amino acid substitutions in proteins which can be used for obtaining analogs of caspase-8 interacting proteins for use in the present invention include any known method steps, such as presented in U.S. Pat. Nos. RE 33,653, 4,959,314, 4,588,585 and 4,737,462, to Mark et al.; U.S. Pat. No. 5,116,943 to Koths et al., U.S. Pat. No. 4,965,195 to Namen et al.; U.S. Pat. No. 4,879,111 to Chong et al.; and U.S. Pat. No. 5,017,691 to Lee et al.; and lysine substituted proteins presented in U.S. Pat. No. 4,904,584 (Shaw et al.).

Besides conservative substitutions discussed above which would not significantly change the activity of caspase-8 interacting protein, either conservative substitutions or less conservative and more random changes, which lead to an increase in biological activity of the analogs of caspase-8 interacting proteins, are intended to be within the scope of the invention.

When the exact effect of the substitution or deletion is to be confirmed, one skilled in the art will appreciate that the effect of the substitution(s), deletion(s), etc., will be evaluated by routine binding and cell death assays. Screening using such a standard test does not involve undue experimentation.

Acceptable caspase-8 interacting analogs are those which retain at least the capability of interacting with caspase-8, and thereby, mediate the activity of caspase-8 in the intracellular pathways, or modulate the activity of caspase-8 itself. In such a way, analogs can be produced which have a so-called dominant-negative effect, namely, an analog which is defective either in binding to caspase-8, or in subsequent signaling or other activity following such binding. Such analogs can be used, for example, to inhibit the cytotoxic effect of caspase-8, or to increase it, depending on whether it is desired to increase cell death or cell survival and depending on which of these activities is the major one modulated by the interaction of caspase-8 interacting protein and caspase-8 (see above), and this by such analogs competing with the natural caspase-8 interacting protein for binding to or interacting with caspase-8.

At the genetic level, these analogs are generally prepared by site-directed mutagenesis of nucleotides in the DNA encoding the caspase-8 interacting protein, thereby producing DNA encoding the analog, and thereafter synthesizing the DNA and expressing the polypeptide in recombinant cell culture. The analogs typically exhibit the same or increased qualitative biological activity as the naturally occurring protein, Ausubel et al., Current Protocols in Molecular Biology, Greene Publications and *Wiley Interscience*, New York, N.Y., 1987–1995; Sambrook et al., Molecular Cloning: A Laboratory Manual, Cold Spring Harbor Laboratory, Cold Spring Harbor, N.Y., 1989.

Preparation of a caspase-8 interacting protein in accordance herewith, or an alternative nucleotide sequence encoding the same polypeptide but differing from the natural sequence due to changes permitted by the known degeneracy of the genetic code, can be achieved by site-specific mutagenesis of DNA that encodes an earlier prepared analog or a native version of a caspase-8 interacting protein. Site-specific mutagenesis allows the production of analogs through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 20 to 25 nucleotides in length is preferred, with about 5 to 10 complementing nucleotides on each side of the sequence being altered. In general, the technique of site-specific mutagenesis is well known in the art, as exemplified by publications such as Adelman et al., DNA 2:183 (1983), the disclosure of which is incorporated herein by reference.

As will be appreciated, the site-specific mutagenesis technique typically employs a phage vector that exists in both a single-stranded and double-stranded form. Typical vectors useful in site-directed mutagenesis include vectors such as the M13 phage, for example, as disclosed by Messing et al., *Third Cleveland Symposium on Macromolecules and Recombinant DNA*, Editor A. Walton, Elsevier, Amsterdam (1981), the disclosure of which is incorporated herein by reference. These phage are readily available commercially and their use is generally well known to those skilled in the art. Alternatively, plasmid vectors that contain a single-stranded phage origin of replication (Veira et al., *Meth. Enzymol.* 153:3, 1987) may be employed to obtain single-stranded DNA.

In general, site-directed mutagenesis in accordance herewith is performed by first obtaining a single-stranded vector that includes within its sequence a DNA sequence that encodes the relevant polypeptide. An oligonucleotide primer bearing the desired mutated sequence is prepared synthetically by automated DNA/oligonucleotide synthesis. This primer is then annealed with the single-stranded protein-sequence-containing vector, and subjected to DNA-polymerizing enzymes such as *E. coli* polymerase I Klenow fragment, to complete the synthesis of the mutation-bearing strand. Thus, a mutated sequence and the second strand bears the desired mutation. This heteroduplex vector is then used to transform appropriate cells, such as *E. coli* JM101 cells, and clones are selected that include recombinant vectors bearing the mutated sequence arrangement.

After such a clone is selected, the mutated caspase-8 interacting protein sequence may be removed and placed in an appropriate vector, generally a transfer or expression vector of the type that may be employed for transfection of an appropriate host.

Accordingly, gene or nucleic acid encoding for a caspase-8 interacting protein can also be detected, obtained and/or modified, in vitro, in situ and/or in vivo, by the use of known DNA or RNA amplification techniques, such as PCR and chemical oligonucleotide synthesis. PCR allows for the amplification (increase in number) of specific DNA sequences by repeated DNA polymerase reactions. This reaction can be used as a replacement for cloning; all that is required is a knowledge of the nucleic acid sequence. In order to carry out PCR, primers are designed which are complementary to the sequence of interest. The primers are then generated by automated DNA synthesis. Because primers can be designed to hybridize to any part of the gene, conditions can be created such that mismatches in complementary base pairing can be tolerated. Amplification of these mismatched regions can lead to the synthesis of a mutagenized product resulting in the generation of a peptide with new properties (i.e., site directed mutagenesis). See also, e.g., Ausubel, supra, Ch. 16. Also, by coupling complementary DNA (cDNA) synthesis, using reverse transcriptase, with PCR, RNA can be used as the starting material for the synthesis of the extracellular domain of a prolactin receptor without cloning.

Furthermore, PCR primers can be designed to incorporate new restriction sites or other features such as termination codons at the ends of the gene segment to be amplified. This placement of restriction sites at the 5' and 3' ends of the amplified gene sequence allows for gene segments encoding caspase-8 interacting protein or a fragment thereof to be custom designed for ligation other sequences and/or cloning sites in vectors.

PCR and other methods of amplification of RNA and/or DNA are well known in the art and can be used according to the present invention without undue experimentation, based on the teaching and guidance presented herein. Known methods of DNA or RNA amplification include, but are not limited to polymerase chain reaction (PCR) and related amplification processes (see, e.g., U.S. Pat. Nos. 4,683,195, 4,683,202, 4,800,159, 4,965,188, to Mullis et al.; U.S. Pat. Nos. 4,795,699 and 4,921,794 to Tabor et al.; U.S. Pat. No. 5,142,033 to Innis; U.S. Pat. No. 5,122,464 to Wilson et al.; U.S. Pat. No. 5,091,310 to Innis; U.S. Pat. No. 5,066,584 to Gyllensten et al.; U.S. Pat. No. 4,889,818 to Gelfand et al.; U.S. Pat. No. 4,994,370 to Silver et al.; U.S. Pat. No. 4,766,067 to Biswas; U.S. Pat. No. 4,656,134 to Ringold; and Innis et al., eds., *PCR Protocols: A Guide to Method and Applications*) and RNA mediated amplification which uses anti-sense RNA to the target sequence as a template for double stranded DNA synthesis (U.S. Pat. No. 5,130,238 to Malek et al., with the tradename NASBA); and immuno-PCR which combines the use of DNA amplification with antibody labeling (Ruzicka et al., *Science* 260:487 (1993); Sano et al., *Science* 258:120 (1992); Sano et al., *Biotechniques* 9:1378 (1991)), the entire contents of which patents and reference are entirely incorporated herein by reference.

In an analogous fashion, biologically active fragments of caspase-8 interacting proteins (e.g. those of any of the caspase-8 interacting proteins or its isoforms) may be prepared as noted above with respect to the analogs of caspase-8 interacting protein. Suitable fragments of caspase-8 interacting protein are those which retain the caspase-8 interacting protein capability and which can mediate the biological activity of caspase-8 or other proteins associated with caspase-8 directly or indirectly. Accordingly, caspase-8 interacting protein fragments can be prepared which have a dominant-negative or a dominant-positive effect as noted above with respect to the analogs. It should be noted that these fragments represent a special class of the analogs of the invention, namely, they are defined portions of caspase-8 interacting proteins derived from the full caspase-8 interacting protein sequence (e.g., from that of any one of the caspase-8 interacting protein or its isoforms), each such portion or fragment having any of the above-noted desired activities. Such fragment may be, e.g., a peptide.

Similarly, derivatives may be prepared by standard modifications of the side groups of one or more amino acid residues of the caspase-8 interacting protein, its analogs or fragments, or by conjugation of the caspase-8 interacting protein, its analogs or fragments, to another molecule e.g. an antibody, enzyme, receptor, etc., as are well known in the art. Accordingly, "derivatives" as used herein covers derivatives which may be prepared from the functional groups which occur as side chains on the residues or the N- or C-terminal groups, by means known in the art, and are included in the invention. Derivatives may have chemical moieties such as carbohydrate or phosphate residues, provided such a fraction has the same or higher biological activity as caspase-8 interacting proteins.

For example, derivatives may include aliphatic esters of the carboxyl groups, amides of the carboxyl groups by reaction with ammonia or with primary or secondary amines, N-acyl derivatives or free amino groups of the amino acid residues formed with acyl moieties (e.g., alkanoyl or carbocyclic aroyl groups) or O-acyl derivatives of free hydroxyl group (for example that of seryl or threonyl residues) formed with acyl moieties.

The term "derivatives" is intended to include only those derivatives that do not change one amino acid to another of the twenty commonly occurring natural amino acids.

As described above, the cleavage assays may be used to determine whether a caspase-8 interacting protein is cleaved by caspase-8. The size-separation of cleaved fragments gives an approximate indication of the location of the cleavage site.

The cleavage site may be further determined by preparing deletion mutants of the protein to be tested and testing each deletion mutant for its susceptibility to cleavage by caspase-8 as described above. Deletion mutants may be constructed by PCR cloning of desired fragments of the protein to be tested, using the DNA sequence of the clone coding for said protein to be tested as a template. The PCR amplified fragments may then be cloned into expression vectors, whereby a ATG start codon and preferably, a Kozak sequence (Kozak, M, Nucleic Acids Res. 12 p. 857–72, 1984) must be provided. Further details on expressing proteins may be found in the above-noted information of Qiagen, relating to his-tagged proteins, but also to protein expression in general. Another reference for protein expression of the further above-mentioned Current Protocols, and specifically chapter 16 therein.

The cleavage site of a protein to be tested may thus be defined by preparing various deletion mutants therefrom and determining the smallest such deletion mutant that is cleaved by caspase-8.

Another way of identifying the cleavage site uses peptides which are generated according to the predicted protein sequence of the clone to be tested. Peptides may be synthesized chemically, e.g., as detailed in Bodanszky and Bodanszky, The practice of peptide synthesis, Springer, New York, ISBN 0-387-13471-9, and Bodanszky, The principles of peptide synthesis, Springer, New York, ISBN 0-387-12359-4. Custom peptide synthesis is further available from several commercial companies, e.g., SynPep Corp., Dublin, Calif. USA, and California Peptide Research, Inc., Napa, Calif., USA. Peptides may also be produced, either as fusion with other proteins or unfused, by expressing recombinant DNA coding therefor, as detailed in the above chapter 16 of Current Protocols.

In order to use peptides for mapping the cleavage site of a protein to be tested, the predicted amino acid sequence of said protein is divided into areas and a peptide corresponding to each area is synthesized. In addition, peptides comprising about half of the amino acids of one area and contiguously comprising further about half of the amino acids of a directly neighboring area are synthesized, so as to be overlapping the border between the two areas. The areas comprise between 5 and 100 amino acids, preferably between 9 and 40 amino acids, and most preferably between 20 and 30 amino acids. The entire set of peptides is now tested as described above for susceptibility to cleavage by caspase-8. The peptides prepared may be provided pure and in large quantities. After the cleavage reaction, they may therefore be analyzed directly by SDS polyacrylamide gel electrophoresis and UV detection or visualization by staining, e.g., using Comassie blue. Alternatively, peptides may be labeled for easier detection, e.g., by isotopic end-labeling (see e.g., Shevchenko A, et al. Rapid Commun Mass Spectrom. 11, p. 1015–24, 1997).

After a peptide screen as described above has been completed, the peptide which is now known to comprise the cleavage site for caspase-8 can be further studied be repeating the same technique, but choosing smaller areas selected from the sequence of the peptide that has been identified.

The actual cleavage site of the peptides should conform to the caspase cleavage sequence XXXD (see Boldin et al., Cell 1996 and Nicholson et al., Killer caspases, Trends in Biochem Sci. 22, 299–306, 1997). The contribution of each amino acid in the peptide may be evaluated by preparing peptides that are mutated in one amino acid and testing these mutated peptides for susceptibility to cleavage with caspase-8. The amino acid to be mutated is preferably replaced by an amino acid selected from the group of charged nonpolar amino acids (see Lehninger, Biochemistry, Worth, N.Y., 1979, chapter 4), most preferably selected from glycine or alanine.

By mutating critical amino acids, it is possible to generate peptides that bind caspase-8, but are not susceptible to cleavage thereby. Binding may be tested by size separation of peptide-caspase-8 complexes under nondenaturing conditions using acrylamide gel electrophoresis.

It is further possible to construct modified peptides that are capable of reacting with the active cysteine of caspase-8, to thereby covalently bind to said cysteine. Reagents that react with thiol groups as known to the person of skill in the art of chemistry may be used for that purpose. Such reagents may bind in a reversible manner. For instance, thiol-group containing reagents may react with the SH group of the active cysteine of caspase-8. The covalent S—S bond formed may be cleaved by reduction, for instance, under physiological conditions in the cytosol or by using a reagent that reduces S—S groups such as Dithiothreitol (DTT). Reagents that react with thiol groups may also irreversibly bind to caspase-8. Such reagents may easily be found among cross-linkers capable of reacting with thiol groups as known in the art, such as disclosed at p. O-90 and following pages in the PIERCE Life Sciences catalog (PIERCE, Rockford, Ill., USA).

Suitable groups that react with thiol groups are for instance pyridyldithio, iodoacetamido, or maleimido groups. These groups may be linked to the peptide via linkers comprising optionally unsaturated aliphatic hydrocarbon chains, —O—, —S—, —NH—, or aromatic groups. The linkers may optionally be substituted.

The thiol-reactive groups may be linked to the peptide by chemical synthesis as known in the art; functional groups of the peptide may be reacted with suitable functional groups of the thiol-reacting group-linker molecule. For instance, a lysine residue present in the peptide sequence, or added thereto for the purpose of creating a suitable functional group, which in the case of lysine is an epsilon-amino group, may be reacted with a heterobifunctional cross-linker such as N-gamma-maleimidobutyryloxy-succinimide ester, to create a peptide wherein the said lysine epsilon-amino group is reacted with the N-hydroxysuccinimide group of the crosslinker, while the maleimido group of the crosslinker remains unreacted and may, upon contact with the caspase-8 cysteine which occurs when the said peptide specifically binds to said caspase-8, react with the thiol group of said cysteine and thereby inactivate said caspase-8.

The position within the peptide used for reacting thereto the thiol-reactive reagent, may be chosen so as to be close to the amino acid (usually aspartic acid) where cleavage by caspase-8 occurs. The linker by which the thiol-reactive group is bound to the peptide may be varied in its length, presence of polar groups, such as hydroxy, charged groups such as Nitro and sulfo-groups, and aromatic groups such as phenylene of phenyl residues. These variations in linker structure will allow the generation of reagent comprising a peptide and covalently bound thereto a thio-reactive reagent that will specifically bind caspase-8 and effectively react with the thiol group of its active cysteine.

The protein to be tested, or a peptide fragment thereof, may be further characterized by introducing said protein or peptide into a mammalian cell and measuring the effect of apoptosis-inducing reagents in said cell.

Expression of a protein or peptide in a mammalian cell may be done by inserting the DNA coding for the protein to be tested into a vector comprising a promoter, optionally an intron sequence and splicing donor/acceptor signals, and further optionally comprising a termination sequence. These techniques are in general described in the above-noted Current Protocols, chapter 16.

The above promoter, intron, and termination sequences are operable in mammalian cells. The promoter is preferably a strong promoter such as the above-noted RSV, CMV, or MPSV promoter. The promoter may also be the SV40 early promoter (Everett, et al. Nucleic Acids Res. 11 p. 2447–64, 1983, and references therein), or a cellular promoter, such as the beta-actin promoter or the ELF-1 promoter (Tokushige, et al., J Virol Methods. 64 p. 73–80, 1997). Also, a hybrid promoter may be used, such as the hybrid between the lac operator and the human ELF-1 alpha promoter as described by Edamatsu et al. (Gene 187,p. 289–94, 1997), the CMV-beta actin hybrid promoter described by Akagi et al., Kidney Int. 51, p. 1265–9, 1997), or the hybrid between tet operator sequences and the CMV promoter (Furth et al., PNAS 91, p. 9302–6, 1994, and references therein).

Intron sequences which may be inserted as complete sequences, i.e., including the splice donor and acceptor sites, may be inserted into the coding sequence of the protein which it is desired to express. Insertion if such intron sequences may enhance RNA stability and thus enhance production of the desired protein. While in principle, suitable intron sequences may be selected from any gene containing introns, preferred intron sequences are the beta-actin intron, the SV 40 intron, and the p55 TNF receptor intron.

The intron sequence may contain enhancer elements which may enhance transcription from the above-noted promoters.

Often, intron sequences also contain transcriptional or translational control sequences that confer tissue specific expression. Therefore, when it is desired to express a protein of the invention in a tissue-specific manner, such intron sequences may be advantageously employed. An example of an intron containing tissue-specific enhancer elements is the erythroid-specific enhancer located in intron 8 of the human 5-aminolevulinate synthase 2 gene (Surinya et al. J Biol Chem. 273, p. 16798–809, 1998), and a discussion of the principle of enhancing protein production using intron sequences, together with example intron sequences, is provided in Huang et al. Nucleic Acids Res. 18, p. 937–47, 1990).

Transcriptional termination sequences and polyadenylation signals may be added at the 3' end of the DNA coding for the protein that it is desired to express. Such sequences may be found in many or even most genes. Advantageously, the SV 40 polyadenylation signal is used (Schek et al., Mol Cell Biol., p. 5386–93, 1992, and references therein).

A preferred vector for expression of a protein in a mammalian cell is the pcDNAH is vector (Invitrogen) which contains the CMV promoter for driving expression of the gene encoding the desired protein. Other vectors that may be used include the pCDNA3 or pMPSVEH vectors. These vectors contain the CMV and the MPSV promoters, respectively.

Using recombinant expression of the protein to be tested, said protein can now be evaluated for its effect on the apoptotic signal which is mediated by caspase-8. To that end, apoptosis may be induced by either overexpression of an apoptosis-inducing protein, such as the CD120a intracellular domain, the CD95 intracellular domain, the Mort-1 protein, caspase-8, or an equivalent thereof; or activation of an apoptotic signal by triggering CD120a, CD95, TRAMP/DR3, or an equivalent receptor. Receptor activation may either be achieved by contacting the receptors with ligand or by cross-linking receptors with antibodies, preferably polyclonal antibodies (see Engelmann et al. J. Biol. Chem. 265, p. 14497–504, 1990).

While in general, triggering of a receptor like CD120a requires the addition of a protein synthesis inhibitor like cycloheximide in order to achieve a strong signal for apoptosis, the overexpression of receptor intracellular domains or of proteins involved in apoptosis signal transduction do not (see Boldin et al., Cell 85, p. 803, 1996). The detection of apoptosis, incubation times and other details and parameters for this assay have been described in the above Boldin et al.

Cell death in cells expressing the protein to be tested, versus cells that do not, may be evaluated by any number of methods, such as methods based upon DNA fragmentation or detection of apoptosis-specific antigens and epitopes, reagents and protocols for detection of apoptosis in kit form are available from the above-noted Boehringer Mannheim and other companies.

Cell death may also be determined by evaluating the morphological appearance of the cells. Apoptotic cell death is characterized by a wavy cell membrane and shrinking of the cells in the absence of cell lysis.

Advantageously, a reporter gene is expressed in the mammalian cell, in order to provide a marker for successful transfection. As the transfection procedure by itself results in some cell death, including cell death of cells that have not been transfected, it is of advantage to only evaluate cells that have been transfected. A preferred reporter gene for this purpose is the lacZ gene, which is easily detected by incubation of transfected cells with Xgal or a similar reagent indicative of active beta-galactosidase. However, any other known reporter gene may be used, preferably a gene whose products are easily detected using a simple color reaction the results of which may be evaluated by using a microscope. For instance, the green fluorescent protein may be used for direct detection without the need for a color reaction. This reporter gene necessitates the use of a fluorescent microscope.

Thus, by only considering cells that have been transfected, i.e., that express the reporter gene, and by counting the percentage of cells demonstrating an apoptotic morphology, it is possible to evaluate the effect of a particular transfected clone and the protein expressed therefrom on apoptosis.

The mammalian cells are preferably HeLa or human embryonic kidney (HEK) 293-T cells. The transfection is preferably done by the calcium phosphate method as described in the above Current Protocols. The morphology of the cells if evaluated one to 150 hours after transfection, preferably 4 to 35 hours and most preferably 20 hours after transfection.

Generation of Antibodies

Polyclonal antibodies may be generated in rabbits, chicken, mice, rats, sheep, or similar mammals. For generation of antibodies against a protein or peptide of the invention, the protein or peptide is produced, as described above, by recombinant DNA technology in mammalian cells. The protein may also be produced in bacterial or insect cells as detailed in the above-noted Current Protocols, chapter 16.

The protein or peptide is the purified from the cells in which it has bee produced. Protein purification methods are known to the person of skill in the art and are detailed e.g., in the above-noted Current Protocols in Molecular Biology, chapter 16, and in Current Protocols in Protein Science, Wiley and Sons Inc. chapters 5 and 6. Advantageously, the protein may be produced as a fusion with a second protein, such as Glutathione-S-transferase or the like, or a sequence tag, such as the histidine tag sequence. The use of fusion or tagged proteins simplifies the purification procedure, as detailed in the above-noted Current Protocols in Molecular Biology, chapter 16, and in the instructions for the above-noted Qiagen his-tag protein expression and purification kit.

If the protein or peptide has been expressed as a fusion protein, it is desirable to cleave the fusion partner before using the protein for the generation of antibodies, in order to avoid generation of antibodies against the fusion partner. The cleavage of fusion partners and the isolation of the desired protein is described in the above-noted Current Protocols in molecular Biology, chapter 16. Vectors, protocols and reagents for expressing and purifying maltose-binding protein fused recombinant proteins are also available commercially.

When producing a peptide of the invention, it may be desirable not to remove the fusion partner, as the fusion protein may stimulate the production of antibodies against the peptide generally this consideration will be relevant when generating antibodies from peptides that are less than 50 amino acids in length.

As noted further above, peptide may also be synthesized by chemical methods known, in the art of chemistry.

The generation of polyclonal antibodies against proteins is described chapter 2 of Current Protocols in Immunology, Wiley and Sons Inc. The generation of antibodies against peptides may necessitate some changes in protocol, because of the generally lower antigenicity of peptides when compared to proteins. The generation of polyclonal antibodies against peptides is described in the above-noted Current Protocols in Immunology, chapter 9.

Monoclonal antibodies may be prepared from B cells taken from the spleen or lymph nodes of immunized animals, in particular rats or mice, by fusion with immortalized B cells under conditions which favor the growth of hybrid cells. For fusion of murine B cells, the cell line Ag-8 is preferred.

The technique of generating monoclonal antibodies is described in many articles and textbooks, such as the above-noted chapter 2 of Current Protocols in Immunology. Chapter 9 therein describes the immunization, with peptides, of animals. Spleen or lymph node cells of these animals may be used in the same way as spleen or lymph node cells of protein-immunized animals, for the generation of monoclonal antibodies as described in chapter 2 therein.

The techniques used in generating monoclonal antibodies are further described in Kohler and Milstein, Nature 256, 495–497, and in U.S. Pat. No. 4,376,110.

The preparation of antibodies from a gene bank of human antibodies the hypervariable regions thereof are replaced by almost random sequences, is described in U.S. Pat. No. 5,840,479. Such antibodies are preferred if it is difficult to immunize an animal with a given peptide or protein. Some Structures are poorly immunogenic and may remain so despite of the addition of adjuvants and of linking to other proteins in fusion constructs. The antibodies described in U.S. Pat. No. 5,840,479 are further preferred if it is desired to use antibodies with a structure similar to human antibodies, for instance, when antibodies are desired that have a low immunogenicity in humans.

Once a suitable antibody has been identified, it may be desired to change the properties thereof. For instance, a chimeric antibody may achieve higher yields in production. Chimeric antibodies wherein the constant regions are replaced with constant regions of human antibodies are further desired when it is desired that the antibody be of low immunogenicity in humans. The generation of chimeric antibodies is described in a number of publications, such as Cabilly et al., PNAS 81, p. 3273, 1984, Morrison et al., PNAS 81, 6851, 1984, Boulianne et al, Nature 312, p. 643, 1984, EP 125023, EP 171496, EP 173494, EP 184187, WO 86/01533, WO 87/02671, and Harlow and Lane, Antibodies: A Laboratory Manual, Cold Spring harbor Laboratory, 1988.

Another type of antibody is an anti-idiotypic antibody. An anti-idiotypic (anti-Id) antibody is an antibody which recognizes unique determinants generally associated with the antigen-binding site of an antibody. An Id antibody can be prepared by immunizing an animal of the same species and genetic type (e.g. mouse strain) as the source of the mAb to which an anti-Id is being prepared. The immunized animal will recognize and respond to the idiotypic determinants of the immunizing antibody by producing an antibody to these idiotypic determinants (the anti-Id antibody). See, for example, U.S. Pat. No. 4,699,880, which is herein entirely incorporated by reference.

The anti-Id antibody may also be used as an "immunogen" to induce an immune response in yet another animal, producing a so-called anti-anti-Id antibody. The anti-anti-Id may be epitopically identical to the original mAb which induced the anti-Id. Thus, by using antibodies to the idiotypic determinants of a mAb, it is possible to identify other clones expressing antibodies of identical specificity.

Accordingly, mAbs generated against the caspase-8 interacting protein, analogs, fragments or derivatives thereof, of the present invention may be used to induce anti-Id antibodies in suitable animals, such as BALB/c mice. Spleen cells from such immunized mice are used to produce anti-Id hybridomas secreting anti-Id mAbs. Further, the anti-Id mAbs can be coupled to a carrier such as keyhole limpet hemocyanin (KLH) and used to immunize additional BALB/c mice. Sera from these mice will contain anti-anti-Id antibodies that have the binding properties of the original mAb specific for an epitope of the above caspase-8 interacting protein, or analogs, fragments and derivatives thereof.

The anti-Id mAbs thus have their own idiotypic epitopes, or "idiotopes" structurally similar to the epitope being evaluated.

The term "antibody" is also meant to include both intact molecules as well as fragments thereof, such as, for example, Fab and F(ab')2, which are capable of binding antigen. Fab and F(ab')2 fragments lack the Fc fragment of intact antibody, clear more rapidly from the circulation, and may have less non-specific tissue binding than an intact antibody (Wahl et al., *J. Nucl. Med.* 24:316–325 (1983)).

It will be appreciated that Fab and F(ab')2 and other fragments of the antibodies useful in the present invention may be used for the detection and quantitation of the caspase-8 interacting protein according to the methods disclosed herein for intact antibody molecules. Such fragments are typically produced by proteolytic cleavage, using enzymes such as papain (to produce Fab fragments) or pepsin (to produce F(ab')2 fragments).

An antibody is said to be "capable of binding" a molecule if it is capable of specifically reacting with the molecule to thereby bind the molecule to the antibody. The term "epitope" is meant to refer to that portion of any molecule capable of being bound by an antibody which can also be recognized by that antibody. Epitopes or "antigenic determinants" usually consist of chemically active surface groupings of molecules such as amino acids or sugar side chains and have specific three dimensional structural characteristics as well as specific charge characteristics.

An "antigen" is a molecule or a portion of a molecule capable of being bound by an antibody which is additionally capable of inducing an animal to produce antibody capable of binding to an epitope of that antigen. An antigen may have one or more than one epitope. The specific reaction referred to above is meant to indicate that the antigen will react, in a highly selective manner, with its corresponding antibody and not with the multitude of other antibodies which may be evoked by other antigens.

The antibodies, including fragments of antibodies, useful in the present invention may be used to quantitatively or qualitatively detect the caspase-8 interacting protein in a sample or to detect presence of cells which express the caspase-8 interacting protein of the present invention. This can be accomplished by immunofluorescence techniques employing a fluorescently labeled antibody (see below) coupled with light microscopic, flow cytometric, or fluorometric detection.

The antibodies (or fragments thereof) useful in the present invention may be employed histologically, as in immunofluorescence or immunoelectron microscopy, for in situ detection of the caspase-8 interacting protein of the present invention. In situ detection may be accomplished by removing a histological specimen from a patient, and providing the labeled antibody of the present invention to such a specimen. The antibody (or fragment) is preferably provided by applying or by overlaying the labeled antibody (or fragment) to a biological sample. Through the use of such a procedure, it is possible to determine not only the presence of the caspase-8 interacting protein, but also its distribution on the examined tissue. Using the present invention, those of ordinary skill will readily perceive that any of wide variety of histological methods (such as staining procedures) can be modified in order to achieve such in situ detection.

Such assays for the caspase-8 interacting protein of the present invention typically comprises incubating a biological sample, such as a biological fluid, a tissue extract, freshly harvested cells such as lymphocytes or leukocytes, or cells which have been incubated in tissue culture, in the presence of a detectably labeled antibody capable of identifying the caspase-8 interacting protein, and detecting the antibody by any of a number of techniques well known in the art.

The biological sample may be treated with a solid phase support or carrier such as nitrocellulose, or other solid support or carrier which is capable of immobilizing cells, cell particles or soluble proteins. The support or carrier may then be washed with suitable buffers followed by treatment with a detectably labeled antibody in accordance with the present invention, as noted above. The solid phase support or carrier may then be washed with the buffer a second time to remove unbound antibody. The amount of bound label on said solid support or carrier may then be detected by conventional means.

By "solid phase support", "solid phase carrier", "solid support", "solid carrier", "support" or "carrier" is intended any support or carrier capable of binding antigen or antibodies. Well-known supports or carriers, include glass, polystyrene, polypropylene, polyethylene, dextran, nylon amylases, natural and modified celluloses, polyacrylamides, gabbros and magnetite. The nature of the carrier can be either soluble to some extent or insoluble for the purposes of the present invention. The support material may have virtually any possible structural configuration so long as the coupled molecule is capable of binding to an antigen or antibody. Thus, the support or carrier configuration may be spherical, as in a bead, cylindrical, as in the inside surface of a test tube, or the external surface of a rod. Alternatively, the surface may be flat such as a sheet, test strip, etc. Preferred supports or carriers include polystyrene beads. Those skilled in the art will know may other suitable carriers for binding antibody or antigen, or will be able to ascertain the same by use of routine experimentation.

The binding activity of a given lot of antibody, of the invention as noted above, may be determined according to well known methods. Those skilled in the art will be able to determine operative and optimal assay conditions for each determination by employing routine experimentation.

Other such steps as washing, stirring, shaking, filtering and the like may be added to the assays as is customary or necessary for the particular situation.

One of the ways in which an antibody in accordance with the present invention can be detectably labeled is by linking the same to an enzyme and used in an enzyme immunoassay (EIA). This enzyme, in turn, when later exposed to an appropriate substrate, will react with the substrate in such a manner as to produce a chemical moiety which can be detected, for example, by spectrophotometric, fluorometric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholin-esterase. The detection can be accomplished by calorimetric methods which employ a chromogenic substrate for the enzyme. Detection may also be accomplished by visual comparison of the extent of enzymatic reaction of a substrate in comparison with similarly prepared standards.

Detection may be accomplished using any of a variety of other immunoassays. For example, by radioactive labeling the antibodies or antibody fragments, it is possible to detect R-PTPase through the use of a radioimmunoassay (RIA). A good description of RIA may be found in Laboratory Techniques and Biochemistry in Molecular Biology, by Work, T. S. et al., North Holland Publishing Company, NY (1978) with particular reference to the chapter entitled "An Introduction to Radioimmune Assay and Related Techniques" by Chard, T., incorporated by reference herein. The radioactive isotope can be detected by such means as the use of a g counter or a scintillation counter or by autoradiography.

It is also possible to label an antibody in accordance with the present invention with a fluorescent compound. When the fluorescently labeled antibody is exposed to light of the proper wavelength, its presence can be then detected due to fluorescence. Among the most commonly used fluorescent labeling compounds are fluorescein isothiocyanate, rhodamine, phycoerythrine, pycocyanin, allophycocyanin, o-phthaldehyde and fluorescamine.

The antibody can also be detectably labeled using fluorescence emitting metals such as $^{152}$E, or others of the lanthanide series. These metals can be attached to the antibody using such metal chelating groups as diethylenetriamine pentaacetic acid (ETPA).

The antibody can also be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

An antibody molecule of the present invention may be adapted for utilization in an immunometric assay, also known as a "two-site" or "sandwich" assay. In a typical immunometric assay, a quantity of unlabeled antibody (or fragment of antibody) is bound to a solid support or carrier and a quantity of detectably labeled soluble antibody is added to permit detection and/or quantitation of the ternary complex formed between solid-phase antibody, antigen, and labeled antibody.

Typical, and preferred, immunometric assays include "forward" assays in which the antibody bound to the solid phase is first contacted with the sample being tested to extract the antigen from the sample by formation of a binary solid phase antibody-antigen complex. After a suitable incubation period, the solid support or carrier is washed to remove the residue of the fluid sample, including unreacted antigen, if any, and then contacted with the solution containing an unknown quantity of labeled antibody (which functions as a "reporter molecule"). After a second incubation period to permit the labeled antibody to complex with the antigen bound to the solid support or carrier through the unlabeled antibody, the solid support or carrier is washed a second time to remove the unreacted labeled antibody.

In another type of "sandwich" assay, which may also be useful with the antigens of the present invention, the so-called "simultaneous" and "reverse" assays are used. A simultaneous assay involves a single incubation step as the antibody bound to the solid support or carrier and labeled antibody are both added to the sample being tested at the same time. After the incubation is completed, the solid support or carrier is washed to remove the residue of fluid sample and uncomplexed labeled antibody. The presence of labeled antibody associated with the solid support or carrier is then determined as it would be in a conventional "forward" sandwich assay.

In the "reverse" assay, stepwise addition first of a solution of labeled antibody to the fluid sample followed by the addition of unlabeled antibody bound to a solid support or carrier after a suitable incubation period is utilized. After a second incubation, the solid phase is washed in conventional fashion to free it of the residue of the sample being tested and the solution of unreacted labeled antibody. The determination of labeled antibody associated with a solid support or carrier is then determined as in the "simultaneous" and "forward" assays.

Immunoassays

The creation of immunoassays, such as RIA or ELISA, has been described in many articles, textbooks, and other publications. Reference is made to WO 97/03998, p. 48, line 4 to p. 52, line 27. Immunoassays of the invention may be if two general types: Firstly, immunoassays using immobilized caspase-8 interacting protein, or an equivalent peptide, may be used in the quantification of caspase-8. Secondly, immunoassays using immobilized antibodies directed against an epitope of a caspase-8 interacting protein may be used to quantify caspase-8 interacting proteins.

Such assays may find use in diagnostics, as the level of caspase-8 and of other proteins involved in apoptotic pathways may need to be evaluated in a number of disorders or syndromes where involvement of such pathways is a possibility.

Nucleic Acids

The clones obtained in the screening of the invention are expected to be partial clones. The obtention of complete clones, if necessary, has been described further above. The DNA sequence of a complete clone and of the partial clone initially found in the screening of the invention may find a variety of uses.

For example, in order to manipulate the expression of a caspase-8 interacting protein, it may be desirable to produce antisense RNA in a cell. To this end, the complete or partial cDNA coding for the caspase-8 interacting protein is inserted into an expression vector comprising a promoter, as noted further above. The 3' end of the cDNA is thereby inserted adjacent to the 3' end of the promoter, with the 5' end of the cDNA being separated from the 3' end of the promoter by said cDNA. Upon expression of the cDNA in a cell, an antisense RNA is therefore produced which is incapable of coding for the protein. the presence of antisense RNA in the cell reduces the expression of the cellular (genomic) copy of the caspase-8 interacting gene.

For the production of antisense RNA, the complete cDNA may be used. Alternatively, a fragment thereof may be used, which is preferably between about 9 and 2,000 nucleotides in length, more preferably between 15 and 500 nucleotides, and most preferably between 30 and 150 nucleotides.

The fragment is preferably corresponding to a region within the 5' half of the cDNA, more. preferably the 5' region comprising the 5' untranslated region and/o the first exon region, and most preferably comprising the ATG translation start site. Alternatively, the fragment may correspond to DNA sequence of the 5' untranslated region only.

A synthetic oligonucleotide may be used as antisense oligonucleotide. The oligonucleotide is preferably a DNA oligonucleotide. The length of the antisense oligonucleotide is preferably between 9 and 150, more preferably between 12 and 60, and most preferably between 15 and 50 nucleotides. the region covered by the antisense oligonucleotide comprises preferably the 3' untranslated region of the cDNA, more preferably it comprises the polyadenylation signal or the translation stop codon, or both.

The mechanism of action of antisense RNA and the current sate of the art of use of antisense tools is reviewed in Kumar et al. Microbiol Mol Biol Rev. 62, p. 1415–1434, 1998. The use of antisense oligonucleotides in inhibition of BMP receptor synthesis has been described by Yeh et al. J Bone Miner Res. 13,. p. 1870–9, 1998. The use of antisense oligonucleotides for inhibiting the synthesis of the voltage-dependent potassium channel gene Kv1.4 has been described by Meiri et al. PNAS 95, p. 15037–15042, 1998. The use of antisense oligonucleotides for inhibition of the synthesis of Bcl-x has been described by Kondo et al., Oncogene 17, p. 2585–91, 1998.

The therapeutic use of antisense drugs is discussed by Stix in Sci Am. 279, p. 46, 50, 1998, Flanagan, Cancer Metastasis Rev 17, p. 169–76, 1998, Guinot and Temsamani, Pathol Biol (Paris) 46, p. 347–54, 1998, and references therein.

Modifications of oligonucleotides that enhance desired properties are generally used when designing antisense oligonucleotides. For instance, phosphorothioate bonds are used instead of the phosphoester bonds naturally occurring in DNA, mainly because such phosphorothioate oligonucleotides are less prone to degradation by cellular enzymes. Peng et al. teach that undesired in vivo side effects of phosphorothioate oligonucleotides may be reduced when using a mixed phosphodiester-phosphorothioate backbone. Preferably, 2'-methoxyribonucleotide modifications in 60% of the oligonucleotide is used. Such modified oligonucleotides are capable of eliciting an antisense effect comparable to the effect observed with phosphorothioate oligonucleotides. Peng et al. teach further that oligonucleotide analogs incapable of supporting ribonuclease H activity are inactive.

Therefore, the preferred antisense oligonucleotide of the invention has a mixed phosphodiester-phosphorothioate backbone. Most preferably, 2'-methoxyribonucleotide modifications in about 30% to 80%, most preferably about 60% of the oligonucleotide are used.

Further modification may be introduced to an antisense oligonucleotide. For instance, the oligonucleotide molecule may be linked to a group comprising optionally partially unsaturated aliphatic hydrocarbon chain and one or more polar or charged groups such as carboxylic acid groups, ester groups, and alcohol groups. Alternatively, oligonucleotides may be linked to peptide structures, which are preferably membranotropic peptides. Such modified oligonucleotide penetrate membranes more easily, which is critical for their function and may therefore significantly enhance their activity. Membrane permeability is especially desirable for antisense drugs that are desired to reach the brain. Palmityl-linked oligonucleotides have been described by Gerster et al. Anal Biochem. 262, p. 177–84, 1998. Geraniol-linked oligonucleotides have been described by Shoji et al., J Drug Target 5, p. 261–73, 1998. Oligonucleotides linked to peptides, e.g., membranotropic peptides, and their preparation have been described by Soukchareun et al., Bioconjug Chem 9, p. 466–75, 1998. Modifications of antisense molecules or other drugs that target the molecule to certain cells and enhance uptake of the oligonucleotide by said cells are described by Wang, J Controlled Release 53, p. 39–48, 1998.

Ribozymes

Given the known mRNA sequence of a gene, ribozymes may be designed, which are RNA molecule that specifically bind and cleave said mRNA sequence (see e.g., Chen et al., Ann. NY Acad. Sci. 660, 271–3, 1992, Zhao and Pick, Nature 365, p. 448, 1993, Shore et al., Oncogene 8, 3183, 1993, Joseph and Burke, J. Biol. Chem. 268, 24515, 1993, Shimayama et al., Nucleic Acids Symp Ser 29, p. 177, 1993, Cantor et al., PNAS 90, p. 10932, 1993).

Accordingly, ribozyme-encoding RNA sequence may be designed that cleave the mRNA of a caspase-8 interacting protein of the invention. The point of cleavage is preferably located in the coding region or in the 5' nontranslated region, more preferably, in the 5' part of the coding region close to the AUG translation start codon.

A DNA encoding a ribozyme according to the invention may be introduced into cells by way of DNA uptake, uptake of modified DNA (see modifications for oligonucleotides and proteins that result in enhanced membrane permeability, as described hereinbelow), or viral vector-mediated gene transfer as detailed hereinbelow.

Introduction of Caspase-8 Interacting Proteins, Peptides, and DNA into Cells

The present invention provides caspase-8 interacting proteins, peptides derived therefrom, antisense DNA molecules, and oligonucleotides. A therapeutic or research-associated use of these tools necessitates their introduction into cells of a living organism. For this purpose, it is desired to improve membrane permeability of peptides, proteins and oligonucleotides. Ways to improve membrane permeability of oligonucleotides have been discussed above. The same principle, namely, derivatization with lipophilic structures, may also be used in creating peptides and proteins with enhanced membrane permeability. For instance, the sequence of a known membranotropic peptide as noted above may be added to the sequence of the peptide or protein. Further, the peptide or protein may be derivatized by partly lipophilic structures such as the above-noted hydrocarbon chains, which are substituted with at least one polar or charged group. For example, lauroyl derivatives of peptides have been described by Muranishi et al., Pharm Research 8:649 (1991). Further modifications of peptides and proteins comprise the oxidation of methionine residues to thereby create sulfoxide groups, as described by Zacharia et al., Eur J Pharmacol 203:353 (1991). Zacharia and coworkers also describe peptide or derivatives wherein the relatively hydrophobic peptide bond is replaced by its ketomethylene isoester ($COCH_2$). These and other modifications known to the person of skill in the art of protein and peptide chemistry enhance membrane permeability.

Another way of enhancing membrane permeability is the use receptors, such as virus receptors, on cell surfaces in order to induce cellular uptake of the peptide or protein. This mechanism is used frequently by viruses, which bind specifically to certain cell surface molecules. Upon binding, the cell takes the virus up into its interior. The cell surface molecule is called a virus receptor. For instance, the integrin molecules CAR and AdV have been described as virus receptors for Adenovirus, see Hemmi et al., Hum Gene Ther 9, p. 2363–73, 1998, and references therein. The CD4, GPR1, GPR15, and STRL33 molecules have been identified as receptors/coreceptors for HIV, see Edinger et al. Virology. 249, p. 367–78, 1998 and references therein.

Thus, conjugating peptides, proteins or oligonucleotides to molecules that are known to bind to cell surface receptors will enhance membrane permeability of said peptides, proteins or oligonucleotides. Examples for suitable groups for forming conjugates are sugars, vitamins, hormones, cytokines, transferrin, asialoglycoprotein, and the like molecules. Low et al., U.S. Pat. No. 5,108,921, describes the use of these molecules for the purpose of enhancing membrane permeability of peptides, proteins and oligonucleotides, and the preparation of said conjugates.

Low and coworkers further teach that molecules such as folate or biotin may be used to target the conjugate to a multitude of cells in an organism, because of the abundant and unspecific expression of the receptors for these molecules.

The above use of cell surface proteins for enhancing membrane permeability of a peptide, protein or oligonucleotide of the invention may also be used in targeting said peptide, protein or oligonucleotide of the invention to certain cell types or tissues. For instance, if it is desired to target cancer cells, it is preferable to use a cell surface protein that is expressed more abundantly on the surface of those cells. Examples are the folate receptor, the mucin antigens MUC1, MUC2, MUC3, MUC4, MUC5AC, MUC5B, and MUC7, the glycoprotein antigens KSA, carcinoembryonic antigen, prostate-specific membrane antigen (PSMA), HER-2/neu, and human chorionic gonadotropin-beta. The above-noted Wang et al., 1998, teaches the use of folate to target cancer cells, and Zhang et al. Clin Cancer Res 4, p. 2669–76 1998, teaches the relative abundance of each of the other antigens noted above in various types of cancer and in normal cells.

The protein, peptide or oligonucleotide of the invention may therefore, using the above-described conjugation techniques, be targeted to certain cell type as desired. For instance, if it is desired to enhance apoptosis in cells of the lymphocytic lineage, a caspase-8 positive modulating protein or peptide of the invention may be targeted at such cells, for instance, by using the MHC class II molecules that are expressed on these cells. This may be achieved by coupling an antibody, or the antigen-binding site thereof, directed against the constant region of said MHC class II molecule to the protein or peptide of the invention. Further, numerous cell surface receptors for various cytokines and other cell communication molecules have been described, and many of these molecules are expressed with in more or less tissue- or cell-type restricted fashion. Thus, when it is desired to target a subgroup of T cells, the CD4 T cell surface molecule may be used for producing the conjugate of the invention. CD4-binding molecules are provided by the HIV virus, whose surface antigen gp42 is capable of specifically binding to the CD4 molecule. An apoptosis-enhancing caspase-8 interacting protein or peptide of the invention may be advantageously targeted to T cells in the treatment of patient who suffer from autoimmune reactions based upon T cells, such as lupus erythematodes patients.

Virus-mediated Cellular Targeting

The proteins, peptides and antisense sequences of the invention may be introduced into cells by the use of a viral vector. The use of vaccinia vector for this purpose is detailed in the above-noted chapter 16 of Current Protocols in Molecular Biology. The use of adenovirus vectors has been described e.g. by Teoh et al., Blood 92, p. 4591–4601, 1998, Narumi et al., Am J Respir Cell Mol Biol 19, p. 936–941, 1998, Pederson et al, J Gastrointest Surg 2, p. 283–91, 1998, Guarg-Lin et al., Transplant Proc 30, p. 2923–4, 1998, and references therein, Nishida et al., Spine 23, p. 2437–42, 1998, Schwarzenberger et al., J Immunol 161, p. 6383–9, 1998, and Cao et al., J Immunol 161, p. 6238–44, 1998. Retroviral transfer of antisense sequences has been described by Daniel et al. J Biomed Sci. 5, p. 383–94, 1998.

When using viruses as vectors, the viral surface proteins are generally used to target the virus. As many viruses, such as the above adenovirus, are rather unspecific in their cellular tropism, it may be desirable to impart further specificity by using a cell-type or tissue-specific promoter. Griscelli et al., Hum Gene Ther. 9, p. 1919–28, 1998 teach the use of the ventricle-specific cardiac myosin light chain 2 promoter for heart-specific targeting of a gene whose transfer is mediated by adenovirus.

Alternatively, the viral vector may be engineered to express an additional protein on its surface, or the surface protein of the viral vector may be changed to incorporate a desired peptide sequence. The viral vector may thus be engineered to express one or more additional epitopes which may be used to target said viral vector. For instance, cytokine epitopes, MHC class II-binding peptides, or epitopes derived from homing molecules may be used to target the viral vector in accordance with the teaching of the invention.

Applications of the Above-described Tools

The caspase-8 interacting proteins of the invention are interacting specifically with caspase-8 subunits involved in the proteolytic activity of caspase-8. Although not wishing to be bound by theory, it is the inventors' belief that the caspase-8 interacting proteins of the invention are "downstream" elements in the signaling pathway involving caspase-8. The upstream agents appear to bind through the caspase-8 prodomain, which mediates protein-protein interaction domain. It appears that an extensive cross-talk with numerous agents orchestrating the apoptotic response may be mediated by protein-protein interactions involving death effector domain (DED) and related domains, such as the domains located in the prodomain of caspase-8. In contrast to these proteins, the caspase-8 interacting proteins of the present invention may be among the direct executioners of the cell death process. For instance, Tip-60, one of the caspase-8 interacting proteins of the invention, is a histone deacetylase enzyme. The protein may therefore be directly involved in changing chromatin structure.

The interaction of the proteins of the invention with caspase-8 has several possible consequences: firstly, modulation of caspase-8 activity. This is demonstrated herein in an in vivo assay wherein the J2 clone of the invention inhibits caspase-8 mediated apoptosis.

Secondly, a caspase-8 interacting protein may increase caspase-8 activity by preventing degradation of caspase-8, or decrease its activity by acting as an inhibitor.

Thirdly, the activity of the caspase-8 interacting protein may be modulated. This is demonstrated herein by the ability of caspase-8 to cleave caspase-8 interacting proteins. It is likely that some of these proteins are inactivated by the cleavage. However, it is also possible that the activity of the proteins is changed, that novel activities are induced, or that the caspase-8 interacting protein is activated by cleavage, just as the caspases themselves.

Consequently, the caspase-8 interacting proteins, the peptides, oligonucleotides and antibodies of the invention are useful in modulating the activity of caspase-8. Downmodulation of caspase-8 is desirable in situations where excessive cell death by apoptosis occurs. For instance, in multiple sclerosis with primary oligodendrogliopathy, autoimmune uveoretinitis, diabetes, lupus, autoimmune myocarditis I, acute liver failure regardless of etiology, HCV-mediated chronic hepatitis, chronic gastritis e.g., type A gastritis, mixed connective tissue disease, (MCTD), Crohn's disease, and ulcerative colitis, it has been suggested that destruction of body tissue is caused by apoptotic signals. Therefore, it may be beneficial to patients suffering from these diseases to dowveinodulate caspase-8 activity in those cells that are destroyed by apoptotic cell death.

For instance, in the above oiligodendropathy, it is desired to inhibit caspase-8 activity, in oligodendrocytes. The cell surface G-protein-coupled phospholipid lysophosphatidic acid receptor is expressed in oligodendrocytes and in various other brain cells, bit not in other tissues of the body. Therefore, a peptide or protein of the invention is targeted to the se cells. This may be achieved by either coupling said peptide or protein to phospholipid lysophosphatidic acid, or by introducing the sequence of an antibody that specifically recognizes said phospholipid lysophosphatidic acid receptor into a viral vector, so that said viral vector specifically binds to said phospholipid lysophosphatidic acid receptor.

Similarly, the peptides or proteins of the invention may be targeted to other cell type involved in other diseases listed above and other diseases where an excess of apoptotic cell death has been shown to mediate the damage in body tissue observed.

Also, the antisense RNA, antisense oligonucleotide, and ribozyme of the invention may be targeted similarly to the above oligodendrocytes, or corresponding cells in other diseases. In that case, the expression of caspase-8 interacting proteins is inhibited, rather than the expression of caspase-8 itself. Inhibiting the expression of a number of caspase-8 interacting proteins may decrease the apoptotic effect of caspase-8. However, decreasing the expression of certain caspase-8 interacting proteins may actually increase the effect of caspase-8, as certain caspase-8 interacting proteins are capable of acting as a negative regulator of caspase-8 activity. The effect of using antisense oligonucleotides and antisense RNA, and of ribozymes must therefore be first tested, e.g., in the above-described in vivo assay, before such agents are considered for treatment.

On the other hand, there are certain situations where it may be desired to increase caspase-8 activity. This may be the case in the same disease as noted above, e.g., in systemic lupus erythematodes. However, the cell types that are to be targeted are different. For instance, in Lupus, the T cell population may contain autoreactive cells that are not destroyed in the thymus. Therefore, the caspase-8 upmodulating agent of the invention should be targeted to T cells. It is preferable to target the caspase-8 upmodulating agent to autoreactive cells. In some diseases, such as multiple sclerosis, certain T cell clones are presumed to play a critical role in development of the disease. The caspase-8 upmodulating agent according to the invention may therefore be targeted to such cells, by using one or more antibodies specifically directed at the variable region of the T cell receptor of the autoreactive T cell clones, for targeting the caspase-8 upmodulating agent of the invention, which may be a caspase-8 interacting protein or a peptide according to the invention.

In view of the above, the present invention encompasses pharmaceutical preparations that comprise a active substance comprising one or more of a caspase-8 interacting protein, a peptide, an antibody, a ribozyme, antisense RNA, or antisense oligonucleotide according to the invention.

The invention further encompasses a pharmaceutical composition comprising a viral vector capable of infecting mammalian cells wherein said vector comprises an operably linked promoter and a DNA sequence of the invention coding for a caspase-8 interacting protein or peptide, a ribozyme, an antisense RNA, an antisense oligonucleotide, or an antibody according to the invention. The viral vector may optionally comprise a coding sequence operably linked to a promoter which encodes an peptide or protein located on the virus surface and which is capable of binding a surface protein of a mammalian cell. The surface protein is preferably a protein that enables uptake of the viral vector, and is preferably expressed in a tissue- or cell-type specific manner, so as to enable targeting of the viral vector.

The caspase-8 interacting protein, its analogs, fragments or derivatives may also be used to isolate, identify and clone other proteins of the same class, i.e., those binding to caspase-8 or to functionally related proteases or proteins, involved in the intracellular signaling process. In this application the above noted yeast two-hybrid system may be used, or there may be used a recently developed system employing non-stringent Southern hybridization followed by PCR cloning (Wilks et al., 1989). In the Wilks et al. publication, there is described the identification and cloning of two putative protein-tyrosine kinases by application of non-stringent southern hybridization followed by cloning by PCR based on the known sequence of the kinase motif, a conceived kinase sequence. This approach may be used, in accordance with the present invention using the sequence of the caspase-8 interacting protein to identify and clone those of related caspase-8 interacting proteins.

Another approach to utilizing the caspase-8 interacting protein, or its analogs, fragments or derivatives thereof, of the invention is to use them in methods of affinity chromatography to isolate and identify other proteins or factors to which they are capable of binding, e.g., other proteins or factors involved in the intracellular signaling process. In this application, the caspase-8 interacting protein, its analogs, fragments or derivatives thereof, of the present invention, may be individually attached to affinity chromatography matrices and then brought into contact with cell extracts or isolated proteins or factors suspected of being involved in the intracellular signaling process. Following the affinity chromatography procedure, the other proteins or factors which bind to the caspase-8 interacting protein, or its analogs, fragments or derivatives thereof of the invention, can be eluted, isolated and characterized.

As noted above, the caspase-8 interacting protein, or its analogs, fragments or derivatives thereof, of the invention may also be used as immunogens (antigens) to produce specific antibodies thereto. These antibodies may also be used for the purposes of purification of the caspase-8 interacting protein (e.g., human N-acetyl-glucosamine-6-phosphate deacetylase or any of its isoforms) either from cell extracts or from transformed cell lines producing caspase-8 interacting protein, or its analogs or fragments. Further, these antibodies may be used for diagnostic purposes for identifying disorders related to abnormal functioning of the caspase-8 mediated FAS-R ligand or TNF system. Thus, should such disorders be related to a malfunctioning intracellular signaling system involving the caspase-8 protein, or a caspase-8 interacting protein, such antibodies would serve as an important diagnostic tool.

It should also be noted that the isolation, identification and characterization of the caspase-8 interacting protein of the invention may be performed using any of the well known standard screening procedures. For example, one of these screening procedures, the yeast two-hybrid procedure as is set forth herein below, was used to identify the caspase-8 protein (see Stanger et al., 1995) and subsequently the various caspase-8 interacting proteins of the invention (besides various other new proteins of the above and below noted co-owned co-pending patent applications). Likewise as noted above and below, other procedures may be employed such as affinity chromatography, DNA hybridization procedures, etc. as are well known in the art, to isolate, identify and characterize the caspase-8 interacting protein of the invention or to isolate, identify and characterize additional proteins, factors, receptors, etc. which are capable of binding to the caspase-8 interacting proteins of the invention.

EXAMPLE IA
Two-hybrid Screen for the Identification of Caspase-8 Interacting Proteins A modified yeast two hybrid system described as "Yeast-three Hybrid system" (Tirode F. et al. 1997) was used to screen for caspase-8 interacting proteins and its potential substrates. The individual vectors, yeast strains, and libraries used were obtained from Clontech (Palo Alto, USA), as components of the MATCHMAKER two-hybrid system (#PT1265-1).

The two caspase-8 subunits were expressed separately under the control of different promoters. The short p10 subunit (Serine 375 to Aspartic acid 479) was cloned into the vector pGBT9 (Clontech) in-frame with the DNA binding domain of the yeast Gal4 protein (amino acids 1–147, sequence numbers according to Laughon et al., Molecular and Cellular Biology, 4, 260–267, 1984). The long, active, p20 subunit (Serine 217 to Aspartic acid 374), was mutated at position 360, i.e., the cysteine present in that position was changed to a serine (C360S), rendering the protease activity of the enzyme inactive. The mutated C360S p20 subunit was expressed as unfused protein under control of the Met25 promoter which is positively regulated in medium lacking methionine (Sangsoda, Mol Gen Genet. 200, p. 407–14, 1985). The possibility to control the activity of the promoter driving expression of the p20 subunit, by adjusting the concentration of methionine in the yeast cell growth medium, makes it possible to (1) use toxic protein subunits as bait, and (2) control the dependence of the protein-protein interaction on the third partner, i.e., the p20 subunit. The p10 and p20 expressing units may be located in different vectors. They may also be located in the same vector. In the presently described example, the modified pGBT9 vector pGBT9-3H (see the above Tirode et al.) was used. The p20 subunit is preferably expressed as a fusion with a nuclear localization signal.

Upon expression, in the absence of methionine, the two subunits associate with each other in the yeast cell. Association of the two subunits was demonstrated by co-immunoprecipitation and Western Blot experiments.

A B cell cDNA library cloned into the pGAD GH vector (Durfee et al., Genes Dev 7, 555–569) was a gift from Dr. S. Elledge. The vector contains the Gal4 activation domain (amino acids 768–881). This GAL4 activation domain is sufficient when fused to the GAL4 DNA-binding domain to induce substantial transcriptional activity of the GAL4 gene, see Ma and Ptashne, Cell, 48, 847–853 (1987).

The GAL upstream activation site ($UAS_G$), as described by Keegan et al. (1986), supra, is present in the upstream region of a reporter gene (lacZ) and of a gene allowing selection (His) in the yeast strain HF7c, obtained from Clontech.

A culture of HF7c was transformed by the above caspase-8 containing plasmids and transformant yeast cells selected by growth in selection medium as described in Clontech yeast protocols, i.e., lacking tryptophane, leucine, methionine, tyrosine. Homoserine was optionally added at 80 mg/l.

A culture of said transformants was then further transformed with the B cell library containing vector, followed by plating on the above medium lacking histidine (selection medium).

Optionally, the selection medium was supplemented with 3-aminotriazole, which is an inhibitor of the enzyme histamine synthetase. The addition of the inhibitor serves to control leaking from the promoter driving the his gene in yeast cells that do not contain caspase-8 interacting proteins. In some cases, weak, non-specific interaction may lead to spurious transcription from the Gal4-UAG-his promoter, leading to yeast clones that grow in selection medium.

Transformants growing in selection medium were selected and the DNA plasmids therein extracted. The DNA was then transformed into HB101 bacteria that allow for selection in medium lacking Leucine.

After growing the bacteria and extracting and purifying plasmid DNA therefrom, the plasmid DNA was then transformed into SFY526 yeast cells. The lacZ activity of SFY526 transformants was then tested by plating on selection medium including histidine and containing Xgal. The yeast colonies were then lifted using a WHATMAN 3MM No. 50 filter paper (for a description of colony lifting, see the above Sambrook et al.), then placed for about 20 sec on aluminum foil, transferred for about 25 sec to liquid nitrogen in order to freeze the yeast cells, exposed for about 1 min. to room temperature in order to thaw the yeast cells, placed in a Petri dish on a WHATMAN 3MM No. 1 filter paper which was previously soaked in Z buffer (beta-galactosidase reaction buffer, see e.g., Clontech protocols, the above Sambrook et al., or the above Current Protocols in Molecular Biology) containing Xgal and beta-mercaptoethanol. The appearance of blue color in the colonies is an indication of active beta-galactosidase. Caspase-8 interacting proteins usually develop blue color in this assay within minutes to overnight, preferably within 5 min. to 3 hours, and most preferably within 5 min. and one hour. Alternatively, beta-galactosidase activity was quantified, by liquid culture in Xgal-containing medium, removing the cells by centrifugation, and measuring the absorbance of the medium using a spectrophotometer.

Clones of cDNA identified in the above screening procedure were then tested further for interaction with other proteins. This was done by transforming clones to be tested together with a non-relevant protein expressed as a fusion with a DNA activation domain in the pGAD GH vector.

Double transformants that are able to grow in medium lacking histidine or show lacZ activity indicated that the library clone bound unspecifically.

As non-relevant proteins, proteins known to be "sticky", i.e., to interact non-specifically with other proteins, were used, as well as other unrelated proteins. For instance, proteins were tested for binding to Lamin, RIP, RAIDD, TRAF2, and MORT1. In general, Lamin-binding proteins were discarded.

The above three-hybrid test was also carried out with the caspase-8 subunit p10 fused to the lexA DNA binding domain. A preferred vector is the pLexA vector available from Clontech. When using lexA as a DNA binding domain, the yeast L40 strain or equivalent should be used.

Caspase-8 interacting proteins were identified in the above-described screening method and further analyzed using in-vivo and in-vitro cleavage assays and signal transduction assays as described further below.

EXAMPLE 2B
A Modified Bait for Two Hybrid Screening for the Identification of Caspase-8 Interacting Proteins A modified caspase-8 bait was used to further screen for caspase-8 interacting proteins with the yeast two-hybrid system (Fields and Song, 1989). Caspase-8 was expressed from the bait vector pGBT9 (Clontech) as a single chain protein. In order to create a bait protein which would resemble the conformation of the active caspase, the pro-domain was removed and the small subunit 2 (starting from serine 375 and ending at aspartic acid 479) was fused to the Gal4 DNA binding domain. The C-terminus of the small subunit was separated from the N-terminus of the large subunit 1 (starting from serine 217 and ending at aspartic acid 374) by a 16 amino-acid Glycine-Serine-linker (GGGGSGGGGSGGGGSG (SEQ ID NO:10)). The two subunits of the active caspase are thus derived from the spontaneous folding of one molecule. The cysteine of the active site in subunit 1 was mutated to serine (sub 1 C360S). Overexpression of this single chain caspase-8 was shown to be functionally similar to overexpression of the wild type caspase-8 as determined by its ability to induce apoptosis in HEK 293-T cells when overexpressed from the pcDNAHis vector like caspase-8. The activity of single chain caspase-8 can be blocked by coexpression of p35, which is a caspase inhibitor.

The two-hybrid screen was carried out as describe further above, except that the single chain caspase-8 as described above expressed from the pGBT9 vector (Clontech).

EXAMPLE 2
Identification of Caspase-8 Interacting Proteins

Using the modified two hybrid screen described in Example IA, several clones encoding specific caspase-8 binding proteins were identified. Specificity of binding of the clones was confirmed in the two hybrid test in yeast, while no binding to control proteins was detected. The selected cDNA clones were isolated and sequenced and the nucleotide sequence compared to those found in the GEN-BANK as described hereinbelow.

EXAMPLE 2.1

Clone L1 was found to contain a partial cDNA sequence identical to amino acids 690–750 of Stat 1. Stat 1 was identified as transcription factor that binds to the interferon-stimulated response element (ISRE) and to the gamma activated sequence (GAS) element (for review see Iffic SN, 1998). Stat 1 has recently been shown to be involved in the regulation of constitutive caspase levels (Kuiner et al. 1997) and to serve as an in-vitro substrate for caspase-3 (King P. et al 1998). It was suggested that the cleavage of Stat 1 may play a role in regulating the apoptotic response itself.

EXAMPLE 2.2

Clone L7 was found to encode a partial cDNA which almost completely matches the C terminal part of an EST clone found in the GENBANK to which no function was attributed (accession number AA608733).

EXAMPLE 2.3

Clone L20 was found to be identical to amino acids 104–420 of NEFA (accession number 462693). NEFA is a novel protein that contains a basic amino acid putative DNA binding domain with a potential nuclear targeting signal, two helix-loop-helix (HLH) motif regions, concurrently EF-hand motifs, an acidic amino acid rich region between the EF-hands, and a leucine zipper motif (Bamikol-Watanabe et al. 1994). NEFA was also found to be a calcium binding protein, and was found to be localized both within the cytoplasm, and on the cell surface and can be also detected in the culture medium. NEFA belongs to the nucleobindin subfamily. The biological role of NEFA however has not yet been clarified. Clone L20 is cleaved by caspase 8 both in-vitro and in-vivo.

EXAMPLE 2.4

Clone L12 was found to encode a partial cDNA which almost completely matches a human EST clone found in the database (accession number M62097). Clone L12 is cleaved in-vitro by caspase-8 as shown by an in-vitro protease assay. Briefly, in-vitro synthesized $^{35}$S labeled protein was incubated for 30–60 min. in protease buffer in the presence of bacterially produced caspase-8. Proteins and their fragments were separated on SDS-PAGE and the results were visualized by autoradiography or phosphoimaging. The protease activity could be blocked by the specific pancaspase inhibitor z-VAD-fluoromethylketone.

EXAMPLE 2.5

Clone L5 was found to encode a cDNA identical to the Tip60 protein (accession number 3024755). Tip60 (Tat interacting protein 60 kDa) was first described as a cellular HIV-Tat transactivator interacting protein (Kamine et al., Virology 216, 357–366, 1996) and was later shown to have histone acetyltransferase activity (Yamamoto and Horikoshi, 1997). Beyond its ability to enhance Tat mediated activation of the HIV promoter, the biological role of Tip60 remains to be defined.

In the 2-hybrid test in yeast, clone L5 was found to bind the caspase-8 subunit 2 alone, as well as the p10–p20 complex. Clone L5 was cleaved in-vitro by caspase-8 in the in-vitro protease assay described in Example 2.4. Tip60 was also cleaved in a caspase-dependent manner upon co-overexpression together with the p55 TNF-receptor in HeLa and HEK 293-T cells. It was also cleaved in HeLa cells upon TNF treatment even in the absence of protein synthesis inhibitors. Briefly, the protein was cloned into the pcDNAHis vector (Invitrogen) and expressed in HEK 293-T or HeLa cells together with an apoptosis inducing protein (e.g., p55TNF-R or caspase-8). Twenty hours after transfection cells were harvested and full cell lysates of 0.5–1×10$^6$ cells were applied to SDS-PAGE and subsequent Western Blot with anti poly-His antibodies (Sigma). Results were visualised by ECL. Several cDNA clones encoding inserts matching the Tip60 protein were isolated. All the clones including the "wild-type full length" clone of Tip60 were found to lack a segment extending from amino acid 94 (Proline) to 145 (Threonine). This section of the protein is not part of the acetylase active site and is not considered essential for the function of the protein. A mutant of Tip-60 wherein aspartic acid residues at position 200 and 203 were replaced by Alanine residues was found to be noncleavable.

EXAMPLE 2.6

Clone M26 was found to encode a partial cDNA which almost completely matched a human EST clone found in the GENBANK (accession number C18037). In the 2 hybrid test in yeast, clone M26 was found to bind the caspase-8 subunit 2 alone.

EXAMPLE 3
Isolation of Caspase-8 Interacting Proteins

Using the two hybrid screen described in EXAMPLE 1B several additional clones encoding specific caspase-8 binding proteins were identified. The selected cDNA clones were isolated and sequenced and the nucleotide sequence compared to those found in the GENBANK as described hereinbelow.

A B-cell library (Durfee T et al., 1993) and a Jurkat T-cell library were screened. Table 2 depicts the initial characterization of the fist group of clones.

TABLE 2

| clone(s) | part of/homologo to | source | lacZ (SFY) | insert length | cleaved |
|---|---|---|---|---|---|
| several | NEFA | ALL-cells | + | 650 . 1100 | in vivo/ in vitro |
| B33 | Nucleobindin | lpr-cells | + | 2000 | in vivo/ in vitro |
| B4.2 | K1AA0615 | male brain | +++ | 3000 | in vitro |
| B8.1 | EST00156 | | +++ | 1500 | in vivo/ in vitro |
| B 11 | Phosphoethanolamine cytidylyl transferase | | +++ | | in vitro |
| B17.1 | H23509 | infant brain | ++ | 1200 | |
| B13.1 | Ribonucleoside diphosphate reductase | EBV | +++ | 700 | in vitro |
| B22 | Cyclophilin A | | + | 700 | |
| B27 | gbAA936350 | | + | 2700 | in vivo/ in vitro |
| B37.1 | EBV | EBV | ++++ | 1400 | |
| J2 | AA746639 | human | ++++ | 600 | in vitro/ in vitro |
| J40 | K1AA0419 | male brain | ++ | 2300 | in vitro | in vivo: 293-T and/or HeLa cells

The partial clones coding for parts of NEFA as well as clone B8.1 were also isolated with the yeast-two-hybrid method described in Example 1A.

EXAMPLE 3.1

Clones B4 (accession number 3327044), B17 (accession number H23509), B27 (accession number AA936350) and J40 (accession number 2887413) encoding cDNA inserts hornologous to the terminal end of the respective ESTs.

EXAMPLE 3.2

Clone B11 encoding a cDNA insert homologous to the C-terminal end of CTP-Phosphoenolamine cytidylyltransferase (ET, accession number D84307). ET is an enzyme involved in metabolism of phospholipids and it catalyses the conversion of phosphoethanolamine into CDP-ethanolamine (Nakashima et al. 1997). Clone B11 was cleaved in-vitro by caspase-8 as demonstrated in the assay described in the above-mentioned Example 2.4.

EXAMPLE 3.3

Clones B13 and B37 encoding a cDNA insert homologous to the C-terminal end of a clone which encodes a part of the EBV genome (accession number V01555).

EXAMPLE 3.4

Clone B22 encoding a cDNA insert homologous to the C-terminal end of T-cell Cyclophilin (accession number Y00052). T-cell Cyclophilin was identified as an intracellular receptor for cyclosporin A and FK506 and to possess intrinsic peptidylprolyl cis-trans-isomerase activity (Haendler B. et al., 1987).

EXAMPLE 3.5

Clone B33 encoding a cDNA insert homologous to C-terminus Nucleobindin (accession number 2506255). Nucleobindin is a secreted protein with DNA and Ca2+ binding property, which is very similar to the NEFA protein described in Example 3.3.

Nucleobindin was originally described as 55 kDa protein that enhanced anti DNA antibody production in cultures of autoimmune 1pr mouse spleen cells (Miura K. et al., 1992). Clone B33 was cleaved by caspase-8 both in-vitro and in-vivo as demonstrated in the above-mentioned assays of Examples 2.4 and 2.5.

EXAMPLE 3.6

Clone J2 contains an insert of 600 bp encoding a partial protein sequence which gives rise to a ~20 kDa polypeptide when expressed in vitro in a cell free system as well as in cells. The polypeptide encoded by Clone J2 is cleaved in-vitro by caspase-8 and in-vivo in HEK 293-T and HeLa cells upon co-expression with p55TNF-R or caspase-8 in the above-mentioned assays of Examples 2.4 and 2.5.

The nucleotide and deduced amino acid sequence of clone J2 are provided in FIG. 2.

Comparison and alignment of the 5' extension of clone J2 by PCR to the sequences published in the database revealed homology of clone J2 to a human EST (accession number AA460869), corresponding to a putative human N-Acetylglucosamine-6-Phosphate Deacetylase as well as to an additional clone (L48741), and allowed the composition of the putative full length human N-Acetylglucosamine-6-Phosphate Deacetylase, provided in FIG. 3.

EXAMPLE 4
Functional Characterization of Clone J2

The initial functional characterization of clone J2 revealed that it has an inhibitory activity on caspase-8 and human p55TNF-R induced apoptosis in HEK 293-T and HeLa cells.

Expression of J2 suppressed/delayed apoptosis of the HEK 293-T cells cotransfected with the p55 TNF receptor, or of the HeLa cells treated with TNF and cycloheximide to 25–50% as illustrated in FIG. 4. The quantification of apoptotic cell death was performed by determination of the portion of beta-galactosidase-expressing cells exhibiting apoptotic morphology 20 hrs after transfection of the indicated constructs. Data are expressed as the mean percentage of blue cells exhibiting signs of apoptosis as a fraction of the total number of blue cells counted (about 500 cells per sample). Alternatively, green fluorescent protein was used as a marker and detected by fluorescent confocal microscopy.

EXAMPLE 5

Cloning of Caspase-8 Interacting Proteins

A human placenta cDNA library expressed from the pACT2 vector (available from Clontech, Palo Alto, USA) was screened by the two hybrid screening method using the bait described in Example 1B above. Using this screening procedure several clones encoding specific caspase-8 binding proteins were identified. Clones P16, P27, P43, P70, P74 and P79 were further studied.

Sequencing of the cDNA inserts of cDNA clones P43, P16 and P74 indicated they share some homologous sequences. Clone P74 had the longest cDNA insert, of about 3000 bp, and appeared to encode a protein with a deduced open reading frame of 574 amino acids and with an expected molecular weight of about 68–70 kDa. The sequences of the three abovementioned cDNA inserts were compared to sequences found in public databases. The cDNA inserts of clones P43, P16 and P74 were found to have some homology to the sequence of two EST clones found in the GENBANK (W04418 and N64095). The sequence of all three cDNA inserts appeared to constitute the 3' ends of different splice isoforms of the same protein. Alignment of the sequences of the three cDNA inserts confirmed the open reading frame of 574 amino acids within the sequence of P74 (shown in FIG. 5). A similar sequence was also found within a genomic clone identified in another public database (RPCI5-1057I20; Roswell Park Cancer Institute Human PAC library) which localizes to human chromosome 12q31. The open reading frame deduced from the sequence of this PAC clone was 1428 amino acids (shown in FIG. 6) and comprises the above open reading frame having 574 amino acids. FIG. 7 shows an alignment of the sequence of the open reading frame of the deduced amino acid sequence of the cDNA insert of clone P74 (denoted 'Cloned'), with the open reading frame deduced from the sequence of the PAC clone (denoted 'Deduced').

From comparison of the deduced amino acid sequence of clone P74 and the sequence deduced from the full length PAC clone it appears that the full length protein corresponding to P74 is longer at the 5' end and may possibly start with the first or one of the first methionines of the sequence of PAC shown in FIG. 6.

The sequence of clone P74 was also found to display significant homology to a highly homologous region of mouse and human histone deacetylases, a region which could be the domain containing the histone deacetylase enzymatic active site, suggesting the protein encoded by P74 may share the function of these proteins. The sequence in the region between 163–1716 bp of the partial cDNA of clone P74 displays approximately 80% homology to histone deacetylase A (GENBANK accession number NP_006028). The sequence, in the region between 385–1707 bp of the partial cDNA of clone P74 displays homology to the sequence of histone deacetylase 5 (GENBANK accession number NP_005465). The sequence in the region between 418–1629 bp of the partial cDNA of clone P74 displays homology to the sequence of histone deacetylase mHDA1 (GENBANK accession number AAD09834) and the sequence in the region between 424–1551 bp of the partial cDNA of clone P74 displays homology to the sequence of histone deacetylase 6 (GENBANK accession number NP_006035). An alignment of the amino acid sequence of the full length protein deduced from the PAC sequence with that of histone deacetylase A (GENBANK accession number NP-006028.1) is shown in FIG. 8.

EXAMPLE 6

Functional Characterization of Caspase-8 Interacting Proteins

A) Proteins encoded by cDNA clones J2, or P16, or P43, or P70, or P74, or P79, identified in the two hybrid screening were expressed in reticulocyte lysates in the presence of 35S Methionine in the TNT® T7 Coupled Retyculocyte Lysate System (available from Promega, cat. #L4610), and separated on an SDS-PAGE gel (see FIG. 9A). The same amounts of reticulocyte lysates expressed proteins were analysed for binding to the fusion protein of the two subunits of caspase-8 GST-S2-S1 (C360S) of above example 1B, fused to GST and expressed in bacteria. After preclearing by a 1 hour incubation at 4° C. with GST beads alone, the TNT® produced proteins were precipitated with caspase-8 GST-S2-S1 fusion protein coupled to GST beads by 1 hr incubation at 4° C. with the GST beads, GST precipitates were washed and proteins binding to caspase-8 were separated from the beads by boiling in SDS-containing sample buffer and resolved by SDS-PAGE. The proteins capable of binding to the caspase-8 construct could thus be visualised by autoradiography. The protein encoded by clone P74 appeared to specifically bind in vitro to caspase-8 (see FIG. 9B) as compared to the binding of GST-S2-S1 (C360S) to Bid, a known proximal substrate of caspase-8 in the Fas apoptotic signalling pathway. Full size proteins produced in the reticulocyte lysate are marked in the figure by asterisks.

In the two hybrid tests described in the above example 1A the protein encoded by P74 was found to bind to the fusion protein encoded by the two subunits of caspase 8 but not to the small subunit of caspase-8 expressed alone. In comparison, other proteins mentioned in the above examples, such as Tip60, do bind to the small S2 subunit of caspase-8 when it is expressed alone (data not shown).

Figure 10:
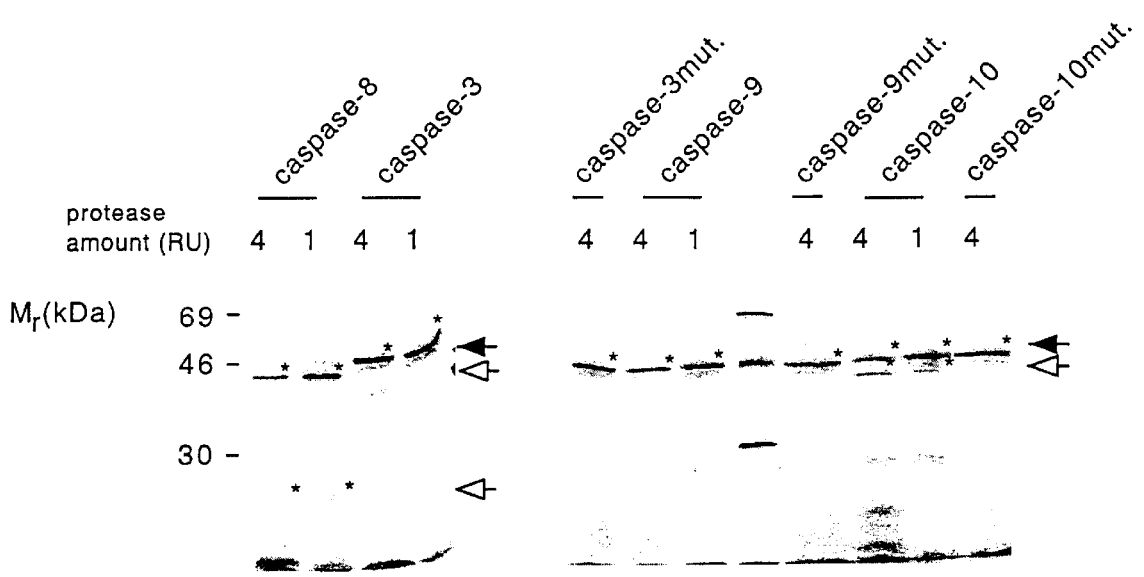
FIG. 10 shows the results of cleavage of the protein encoded by the partial P43 cDNA clone by Caspase-8 or by Caspase-10 or by Caspase-3 or by Caspase-9 or by mutants of Caspase 3 or of Caspase-9 or of Caspase-10. The volumes of the total bacterial lysate of the recombinant caspases expressed in *E. Coli* that were used, are indicated in relative units (RU). The position of the molecular weight markers is shown on the left of the gel. The proteins of interest are marked by an asterisk: the full head arrows show the full size P43 protein the open head arrows show the cleavage products.

B) The protein encoded by the P43 cDNA was expressed in vitro in reticulocyte lysates in the presence of 35S Methionine using the TNT® T7 Coupled Reticulocyte Lysate System, and subjected to cleavage by recombinant wild type or mutant caspase 3 or caspase 9 or caspase 10 expressed in E. coli as Histidine tagged subunit 2-subunit 1 (S2-S1) fusion proteins. Caspase-8 was expressed as a subunit 1-subunit 2 (S1-S2)-Histidine tagged fusion protein. 1 and 4 volumes of the total bacterial lysate, defined as 1 or 4 relative units (RU), were used in a protease assay (FIG. 10). Briefly, in-vitro synthesized 35S labelled proteins were incubated for 30 min. in protease buffer at 37° C. in the presence of bacterially produced caspase-8. Proteins and their fragments were separated on SDS-PAGE and the results were visualised by autoradiography or by phosphoimaging. The results indicated that the protein encoded by the P43 cDNA used as substrate, was effectively cleaved by caspase-8, was weakly cleaved by Caspase-10, and it was not cleaved by caspase-3 nor by caspase-9 (FIG. 10). The protein thus appears to be a specific substrate of caspase-8.

C) To analyse the effect of the newly cloned proteins on apoptotic cell death induced by the TNF receptor signaling pathway, the selected cDNAs were cloned into pcDNA 3.1/His C expression vectors (available from Invitrogen) and transiently cotransfected with p55 TNFR receptor expressed in the pcDNA3 vector (Invitrogen) and with the green fluorescence protein (GFP) expressed from the pEGFPC1 expression vector (Clontech), into HEK-293-T cells. The Tip60 cDNA and the Δ32-Tip60 lacking the first 32 N-terminal amino acids were cloned into the pCGN vector (described in M. Tanaka and W. Herr, Cell 60, 375–386, 1990) in which a hemagglutinin (HA) tag was fused to the N terminal end of the cDNA, and used in the same experimental setting.

Figure 11:
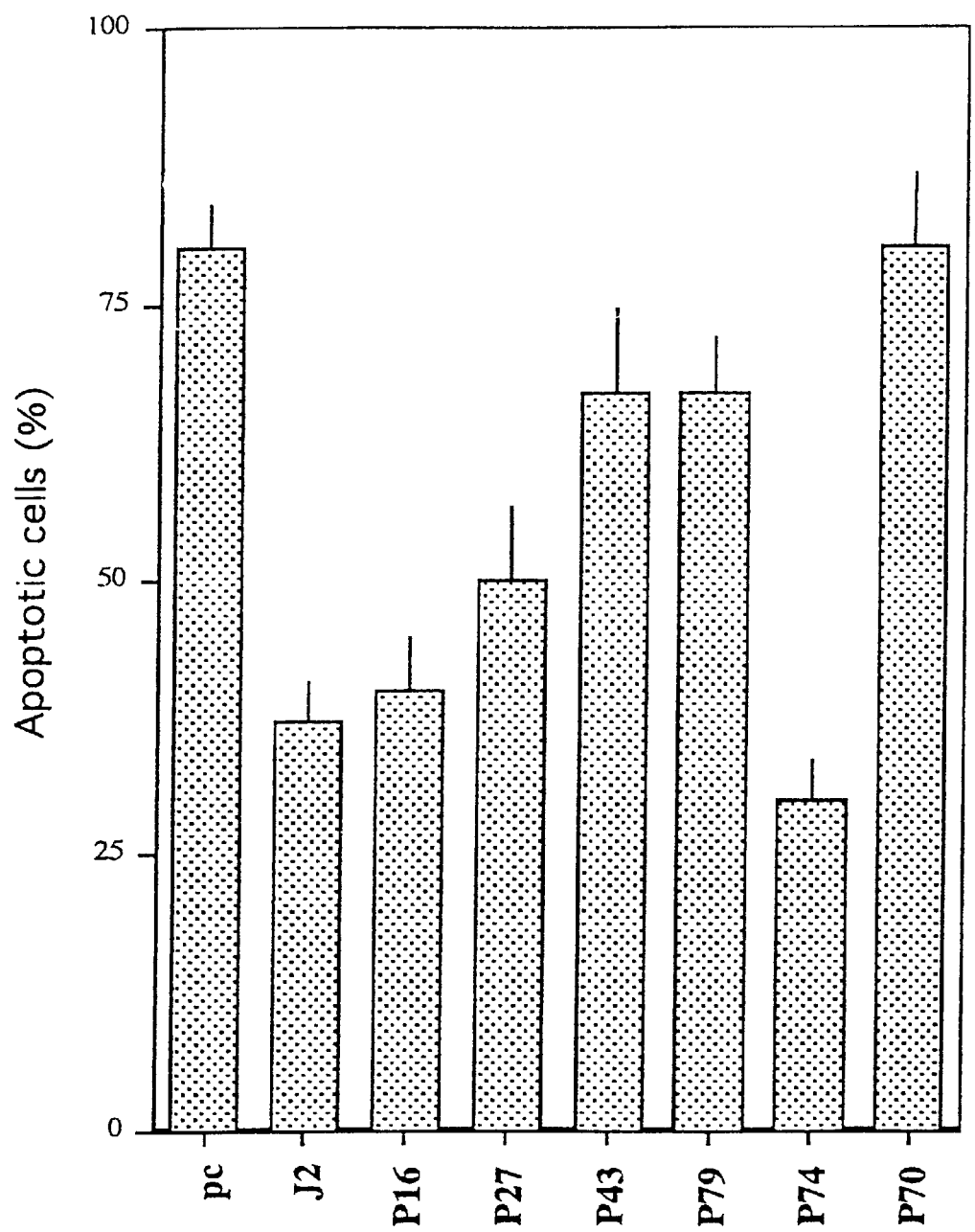
FIG. 11 shows the functional activity of the proteins encoded by cDNA clones identified by two hybrid screening expressed as the percentage of cells undergoing apoptosis, following cotransfection of HEK-293T cells with the p55 TNF receptor and with the Green Fluorescence Protein (denoted PC) without or with the cDNA inserts of clones J2 or P16 or P27 or P43 or P79 or P74 or P70.
Figure 12:
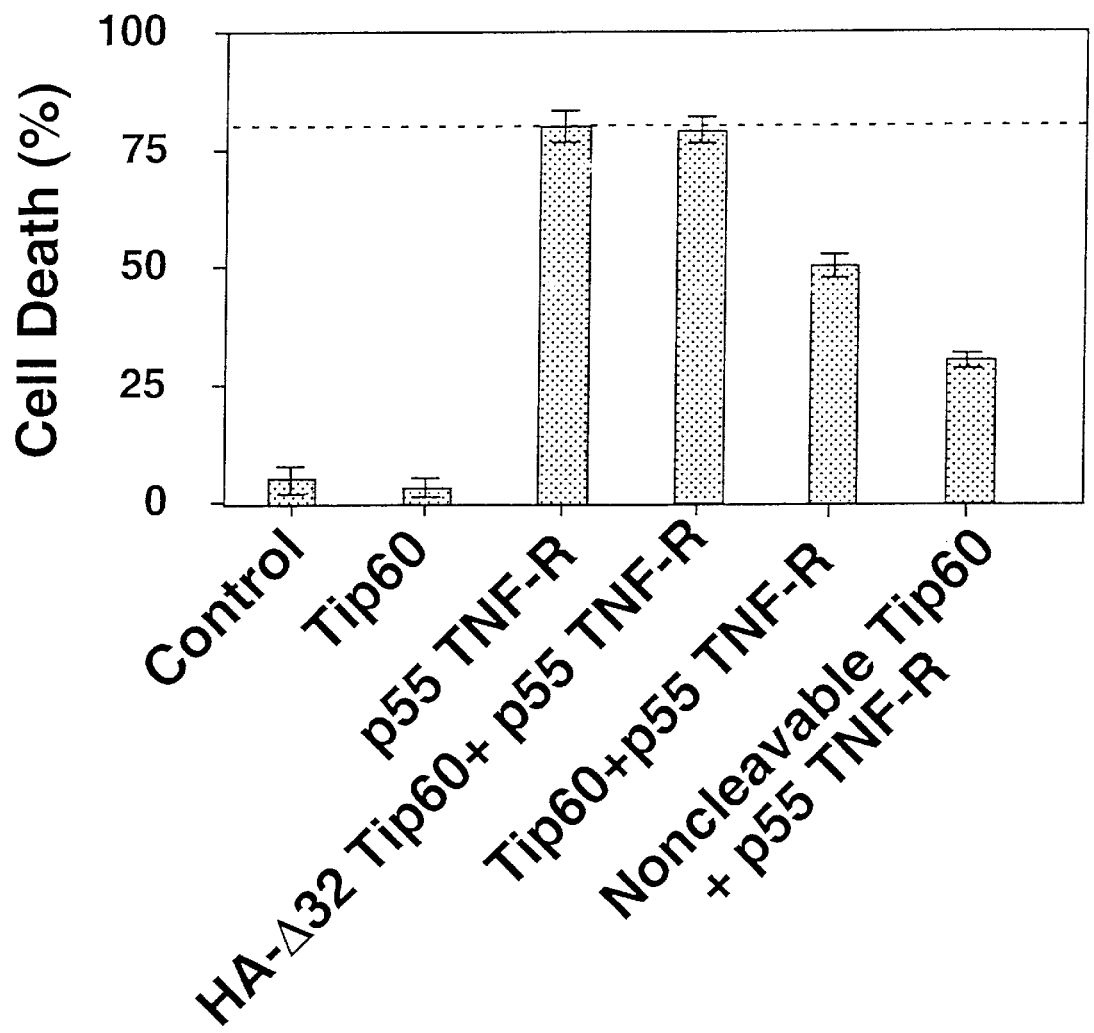
FIG. 12 shows the cell death inhibiting activity of wild type and of the noncleavable mutant of Tip60 in HEK-293T cells cotransfected with the p55 TNF receptor and with the Green Fluorescence Protein as well as the effect of the Δ32-Tip60 lacking the first 32 N-terminal amino acids. Control cells were transfected with the pCGN vector alone.

After 24 hours the transfected cells were examined under a fluorescent microscope and cell death was scored by determining the number of cells displaying an apoptotic morphology out of the total population of fluorescent cells. The P74 protein overexpressed from the partial cDNA cloned into the pcDNA-His vector was found to protect HEK-293-T and HeLa cells from death induced by overexpression of the p55 TNF receptor (FIG. 11) or overexpression of the fused two subunits of caspase-8 (not shown). The wild type Tip60 and the noncleavable Tip60 mutant, wherein aspartic acid residues at position 200 and 203 were replaced by Alanine residues, were found to protect HEK-293-T cells from death induced by overexpression of the p55 TNF receptor (FIG. 12) while the Δ32-Tip60 lacking the first 32 N-terminal amino acids did not show this protective effect.

Having now fully described this invention, it will be appreciated by those skilled in the art that the same can be performed within a wide range of equivalent parameters, concentrations and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, am entirely incorporated by reference herein, including all data, tables, figures, and text presented in the cited references. Additionally, the entire contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications arc intended to be within the meaning and range of equivalents of the disclosed embodiments, based on the teaching and guidance presented herein.

It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

References

Ahmad M et al. *Cancer Res* 1997; 57(4):615–9
Bamikol-Watanabe S. et al. *Biol Chom Hoppe Seyler* 1994;375(8):497–512
Cohen O M *Biochem J* 1997;326 (Pt 1). 1–16
Duan H et al. *Nature* 1997;385(6611):86–9
Durfee T et al. *Genes Dev* 1993;7(4).SSS-69
Femandes-Alnemri T et al. *Proc Natl Acad Sci* 1996; 193 (15):7464–9
Fields S, Song O *Nature* 1989;340(6230):245–6
Haendler B. et al, *EMBO J* 1987;6(4):947–50
Ihle *JN Cell* 1996;84(3).331–4
Kamine J. et al. *Virol@* 1996;216(2):357–66
King P et al. *J Biol Chem* 1998;273(15).8699–704
Kischkel F C et al. *EMBO J* 1995; 14(22);5579–88
Kumar A et al. *Science* 1997;278(5343):1630–2
Quelle F W et al. *J Biol Chem* 1995;270(35):20775–80
MacFarlane M et al. *JBiol Chem* 1997;272(41):25417–20
Mittl P R et al *JBiol Chem* 1997;272(10):6539–47
Miura K et al. *Biochem Biophys Res Commun* 1992; 187 (1),375–80
Muzio M et al *JBiol Chem* 1998.,273(5):2926–30
Nagata S et al. *Cell* 1997;88(3):355–65
Nakashima A et al. *JBiol Chem* 1997;272(14):9567–72
Nicholson D W et al. *Tren& Biochem Sci* 1997;22(8) :299–306
Rotonda J et al *Nat Struct Biol* 1996;3(7):619–25
Salvesen G S et al. *Cell* 1997;91(4):443–6
Srinivasula S M et al. *ProcNatlAcadSciUSA* 1996;93(25) :14486–91
Srinivasula S M et al. *JBiot Chem* 1998;273(17).10107–11
Thornberry N A et al. *JBiol Chem* 1997;272(29):17907–11
Tirode F et al. *JBiol Chem* 1997;272(37):22995–9
Yamamoto T et al. *JBiol Chem* 1997;272(49):30595–8
Yang X et al. *Mol Cell* 1998; 1(2).319–25

What is claimed is:

1. A purified polypeptide that binds to caspase-8, said polypeptide comprising:

(a) the amino acid sequence of SEQ ID NO:6;

(b) the amino acid sequence of an analog of (a), having no more than ten changes in the amino acid sequence of (a), each said change being a substitution, deletion or insertion of an amino acid, which analog binds to caspase-8;

(c) the amino acid sequence of a polypeptide encoded by a DNA sequence capable of hybridizing with the DNA sequence of SEQ ID NO:5, under moderately stringent conditions, which polypeptide binds to caspase-8;

(d) a derivative of (a), (b), or (c), which binds to caspase-8.

2. The polypeptide in accordance with claim 1, wherein said polypeptide consists of the polypeptide of (a) or (b) or derivative of (a) or (b) which binds to caspase-8.

3. The polypeptide in accordance with claim 1, wherein said polypeptide comprises the polypeptide of (a) or a derivative of (a) which binds to caspase-8.

4. A polypeptide in accordance with claim 1, which consists of the amino acid sequence of SEQ ID NO:6.

5. A composition comprising a polypeptide according to claim 1, and a pharmaceutically acceptable excipient.

6. A purified polypeptide that binds to caspase-8, said polypeptide consisting of the amino acid sequence of a fragment of SEQ ID NO: 6, which fragment binds to caspase-8, or a derivative thereof which binds to caspase-8.

7. A caspase-8 interacting peptide in accordance with claim 6, consisting of a derivative of said fragment, which derivative binds to caspase-8.

* * * * *